(12) United States Patent
Roche et al.

(10) Patent No.: US 7,064,823 B2
(45) Date of Patent: Jun. 20, 2006

(54) CONSUMABLE TUBE FOR USE WITH A FLOW CYTOMETRY-BASED HEMATOLOGY SYSTEM

(75) Inventors: John W. Roche, Scarborough, ME (US); W. Peter Hansen, Canaan, NY (US); Michelle L. Coleman, Yarmouth, ME (US); Harold R. Crews, Coral Springs, FL (US)

(73) Assignee: IDEXX Laboratories, Inc., Westbrook, ME (US)

( * ) Notice: Subject to any disclaimer, the term of this patent is extended or adjusted under 35 U.S.C. 154(b) by 158 days.

(21) Appl. No.: 10/159,944

(22) Filed: May 31, 2002

(65) Prior Publication Data
US 2003/0030783 A1    Feb. 13, 2003

Related U.S. Application Data

(62) Division of application No. 09/715,593, filed on Nov. 17, 2000, now Pat. No. 6,784,981.

(60) Provisional application No. 60/208,849, filed on Jun. 2, 2000.

(51) Int. Cl.
G01N 1/10 (2006.01)
G01N 21/00 (2006.01)

(52) U.S. Cl. .................... 356/246; 356/436

(58) Field of Classification Search .............. 356/246, 356/436, 440, 337–339, 437; 422/102, 82.05, 422/82.09, 82.11; 436/165, 168, 169
See application file for complete search history.

(56) References Cited

U.S. PATENT DOCUMENTS

| | | | |
|---|---|---|---|
| 3,925,018 A | * 12/1975 | Saunders | 435/10 |
| 4,013,368 A | * 3/1977 | Acker et al. | 356/246 |
| 4,043,669 A | * 8/1977 | Gehatia et al. | 356/340 |
| 4,250,394 A | * 2/1981 | O'Connor | 250/574 |
| 4,665,553 A | * 5/1987 | Gershman et al. | 382/133 |
| 5,125,737 A | 6/1992 | Rodriguez et al. | 356/39 |
| 5,155,044 A | 10/1992 | Ledis et al. | 436/17 |
| 5,284,771 A | 2/1994 | Fan et al. | 436/10 |
| 5,350,695 A | 9/1994 | Colella et al. | 436/63 |
| 5,360,739 A | 11/1994 | Fan et al. | 436/63 |
| 5,386,287 A | 1/1995 | Berssen et al. | 356/326 |
| 5,411,891 A | 5/1995 | Fan et al. | 436/63 |
| 5,438,003 A | 8/1995 | Colella et al. | 436/63 |
| 5,451,525 A | 9/1995 | Shenkin et al. | 436/63 |

(Continued)

*Primary Examiner*—Layla G. Lauchman
(74) *Attorney, Agent, or Firm*—Carter DeLuca Farrell & Schmidt, LLP

(57) ABSTRACT

The present invention is a flow cytometry-based hematology system useful in the analysis of biological samples, particularly whole blood or blood-derived samples. The system is capable of determining at least a complete blood count (CBC), a five-part white blood cell differential, and a reticulocyte count from a whole blood sample. The system preferably uses a laser diode that emits a thin beam to illuminate cells in a flow cell and a lensless optical detection system to measure one or more of axial light loss, low-angle forward scattered light, high-angle forward scattered light, right angle scattered light, and time-of-flight measurements produced by the cells. The lensless optical detection system contains no optical components, other than photoreactive elements, and does not include any moving parts. Finally, the system uses a unique system of consumable reagent tubes that act as reaction chambers, mixing chambers, and waste chambers for the blood sample analyses. The consumable tubes incorporate reference particles, which act as internal standards to ensure that the dilutions made during processing of the samples have been carried out correctly, and to ensure that the instrument is working properly. The present invention also relates to methods for using the system.

72 Claims, 29 Drawing Sheets

U.S. PATENT DOCUMENTS

| | | |
|---|---|---|
| 5,475,487 A | 12/1995 | Mariella, Jr. et al. ....... 356/336 |
| 5,492,833 A | 2/1996 | Rodriguez et al. ............ 436/63 |
| 5,510,267 A | 4/1996 | Marshall ...................... 436/63 |
| 5,585,246 A * | 12/1996 | Dubrow et al. ............ 435/7.24 |
| 5,616,501 A | 4/1997 | Rodriguez et al. ............ 436/63 |
| 5,627,037 A * | 5/1997 | Ward et al. ................ 435/7.21 |
| 5,691,204 A | 11/1997 | Kim et al. ..................... 436/8 |
| 5,728,582 A * | 3/1998 | Taki et al. .................... 436/10 |
| 5,733,784 A | 3/1998 | Studholme et al. ........... 436/63 |
| 5,737,078 A | 4/1998 | Takarada et al. ............ 356/338 |
| 5,753,186 A * | 5/1998 | Hanley et al. .............. 422/101 |
| 5,858,667 A | 1/1999 | Dertinger et al. .............. 435/6 |
| 5,872,627 A | 2/1999 | Miers ......................... 356/338 |
| 5,917,584 A | 6/1999 | Li et al. ....................... 356/39 |
| 5,939,326 A * | 8/1999 | Chupp et al. ................. 436/43 |
| 6,074,879 A | 6/2000 | Zelmanovic et al. ......... 436/10 |
| 6,228,652 B1 | 5/2001 | Rodriguez et al. ............ 436/63 |
| 6,232,125 B1 | 5/2001 | Deka et al. .................... 436/63 |
| 6,261,519 B1 * | 7/2001 | Harding et al. ............... 422/58 |
| 6,271,035 B1 | 8/2001 | Deka et al. .................... 436/10 |
| 6,365,106 B1 * | 4/2002 | Nagai .......................... 422/73 |
| 6,410,337 B1 * | 6/2002 | Brady et al. .................. 436/69 |
| 6,612,719 B1 | 9/2003 | Richardson et al. |

* cited by examiner

SPECTRUM WITH SINGLE MODE OPERATION

SPECTRUM WITH HFM OPERATION

CONSUMABLE TUBE FOR USE WITH A FLOW CYTOMETRY-BASED HEMATOLOGY SYSTEM

The present application is a divisional application of copending U.S. patent application Ser. No. 09/715,593, filed Nov. 17, 2000, now U.S. Pat. No. 6,784,981, which claimed the benefit of U.S. Provisional patent application Ser. No. 60/208,849, filed on Jun. 2, 2000.

FIELD OF THE INVENTION

This invention relates in general to bioparticle analysis, and more specifically to flow-cytometry-based methods and devices for performing automated blood cell analysis.

BACKGROUND OF THE INVENTION

Mammalian peripheral blood usually contains three major classifications of blood cells—red blood cells ("RBCs"), white blood cells ("WBCs"), and platelets ("PLTs"). These cells are suspended in a solution referred to as plasma, which contains many different proteins, enzymes, and ions. The functions of the plasma components include blood coagulation, osmolality maintenance, immune surveillance, and a multitude of other functions.

Mammals usually have anywhere from $2-10 \times 10^{12}$ RBCs per liter. RBCs are responsible for oxygen and carbon dioxide transport within the circulatory system. In many mammals, including humans, normal mature red cells have a bi-concave cross-sectional shape and lack nuclei. RBCs can range in diameter between 4 and 9 microns, depending on the species, and have a thickness that is generally less than 2 microns. The RBCs contain high concentrations of hemoglobin, a heme-containing protein which performs the dual roles of oxygen and carbon dioxide transport. Hemoglobin is responsible for the overall red color of blood, due to the presence of iron in the heme molecule. In the present application, the terms "erythrocytes", "red blood cells", "red cells", and "RBCs" are used interchangeably to refer to the hemoglobin-containing blood cells present in the circulation as described above.

In addition to mature RBCs, immature forms of red blood cells can often be found in peripheral blood samples. A slightly immature RBC is referred to as a reticulocyte, and the very immature forms of RBCs are broadly classified as nucleated red blood cells (NRBCs). Higher level non-mammalian animals, such as birds, reptiles, and amphibians, have exclusively nucleated RBCs in their blood.

Reticulocytes are red blood cell precursors that have completed most of the normal red cell development stages in bone marrow, and have expelled their nuclei. The last portion remaining to leave the reticulocyte before it becomes a truly mature RBC is transfer RNA. Detection of reticulocytes is important in clinical evaluation of a patient's ability to produce new red blood cells. The reticulocyte count also can be used to distinguish among different types of anemia. In anemia, red cell production may be diminished to the point where it can no longer keep up with red cell removal, and as a result the overall red blood cell count and hematocrit are low. The presence of an increased number of reticulocytes in anemic patients provides evidence that their bone marrow is functioning, and attempting to make up for the red blood cell deficit. If few or no reticulocytes are detectable in these patients, the bone marrow is not adequately responding to the red blood cell deficit.

White blood cells (also called "leukocytes") are the blood-borne immune system cells that destroy foreign agents, such as bacteria, viruses, and other pathogens that cause infection. WBCs exist in peripheral blood in very low concentrations as compared to red blood cells. Normal concentrations of these cells range from $5-15 \times 10^9$ per liter, which about is three orders of magnitude less than red blood cells. These cells are generally larger than RBCs, having diameters between 6 to 13 microns, depending on the type of white cell and the species. Unlike RBCs, there are a variety of white blood cell types that perform different functions within the body. In this application, the terms "white blood cells", "white cells", "leukocytes", and "WBCs" are used interchangeably to refer to the non-hemoglobin-containing nucleated blood cells present in the circulation as described above.

Measurements of the numbers of white cells in blood is important in the detection and monitoring of a variety of physiological disorders. For example, elevated numbers of abnormal white blood cells may indicate leukemia, which is an uncontrolled proliferation of a myelogenous or a lymphogenous cell. Neutrophilia, or an abnormally high concentration of neutrophils, is an indication of inflammation or tissue destruction in the body, by whatever cause.

White blood cells may be broadly classified as either granular or agranular. Granular cells, or granulocytes, are further subdivided into neutrophils, eosinophils, and basophils. Agranular white cells are sometimes referred to as mononuclear cells, and are further sub-classified as either lymphocytes or monocytes. Measurements of the percentages in the blood of the two major WBC classifications (granulocytes and mononuclear cells) comprise a two-part WBC differential count (or two-part differential). Measurements of the components of these subclassifications (neutrophils, eosinophils, basophils, lymphocytes, and monocytes), produce a five-part WBC differential count (or five-part differential).

Neutrophils are the most prevalent of the granulocytes and of the five major subclasses of white cells, usually making up a little over half of the total number of white blood cells. Neutrophils are so named because they contain granules within their cytoplasm which can be stained at a neutral pH. These cells have a relatively short life span, on the order of a day or less. Neutrophils attack and destroy invading bacteria and other foreign agents in the tissues or circulating blood as part of the body's immune response mechanisms.

Eosinophils are the second most prevalent of the granulocytes, behind the neutrophils, but generally account for less than five percent of the total number of white blood cells. Eosinophils also contain granules within their cytoplasm which can be stained with an eosin stain. Like neutrophils, these cells are short-lived in the peripheral blood. Eosinophils play a part in the body's immune response mechanisms that are usually associated with allergies or parasitic infections.

Basophils are the least common of the granulocytes, and the least common of all the five classifications of WBCs. As they are granulocytes, they contain granules within their cytoplasm which can be stained, in this case using a basic (high pH) stain. These cells also are known to play a role in the body's immune response mechanisms, but the specifics are not certain.

Lymphocytes are the most prevalent of the mononuclear cell types, and generally make up between 20 and 30 percent of the total number of white blood cells. Lymphocytes specifically recognize foreign antigens and in response divide and differentiate to form effector cells. The effector cells may be B lymphocytes or T lymphocytes. B lymphocytes secrete large amounts of antibodies in response to foreign antigens. T lymphocytes exist in two main forms—cytotoxic T cells, which destroy host cells infected by infectious agents, such as viruses, and helper T cells, which stimulate antibody synthesis and macrophage activation by releasing cytokines. Lymphocytes have no granules in their cytoplasm, and their nucleus occupies a large majority of the cell volume. The thin area of cytoplasm outside the nucleus of lymphocytes can be stained with a nucleic acid stain, since it contains RNA. Many lymphocytes differentiate into memory B or T cells, which are relatively long-lived and respond more quickly to foreign antigen than naïve B or T cells.

Monocytes are immature forms of macrophages that, in themselves, have little ability to fight infectious agents in the circulating blood. However, when there is an infection in the tissues surrounding a blood vessel, these cells leave the circulating blood and enter the surrounding tissues. The monocytes then undergo a dramatic morphological transformation to form macrophages, increasing their diameter as much as fivefold and developing large numbers of mitochondria and lysosomes in their cytoplasm. The macrophages then attack the invading foreign objects by phagocytosis and activation of other immune system cells, such as T cells. Increased numbers of macrophages are a signal that inflammation is occurring in the body.

Platelets are found in all mammalian species, and are involved in blood clotting. Normal animals will generally have between $1-5 \times 10^{11}$ platelets per liter. These cellular particles are usually much smaller than RBCs, having a diameter between 1 and 3 μm. Platelets are formed as buds from the surfaces of megakarocytes, which are very large cells found in the bone marrow. The megakaryocytes do not themselves leave the marrow to enter the blood circulation; rather, buds form on the surface, pinch off and enter the circulation as platelets. Like RBCs, platelets lack nuclei and thus cannot reproduce. Functionally, platelets aggregate so as to plug or repair small holes in blood vessels. In the case of larger holes, platelet aggregation acts as an early step in clot formation. As a result, platelet count and function are clinically very important. For example, abnormally low platelet counts may be the cause of a clotting disorder.

Collectively, the counting and sizing of RBCs, the counting of WBCs, and the counting of platelets is referred to as a complete blood count ("CBC"). The separation of white blood cells into the five major classifications (i.e., neutrophils, eosinophils, basophils, lymphocytes, and monocytes) and their quantification on a percent basis is referred to as a five-part differential. The separation of white blood cells into two major classifications, granular and agranular leukocytes, and their quantification on a percent basis is referred to as a two-part differential. The categorizing of red blood cells into two classifications, mature red blood cells and reticulated red blood cells, on a percent basis is referred to as a reticulocyte count.

The determination of a CBC, with a five-part differential and a reticulocyte count, is a common diagnostic procedure performed to diagnose, track and treat an abundance of ailments. These tests make up the great majority of hematology analyses that are performed in medical and veterinary clinical laboratories around the world. These three tests have for many years been performed using a microscope, centrifuge, counting chamber, slide, and appropriate reagents. However, the skills necessary to perform these test manually are rare and require years of training. Furthermore, the time required to perform each of these tests manually is very high. As a result, significant automation via instrumentation has been pursued in this field since the early 1950's, when the first impedance particle counters appeared.

An impedance particle counter counts individual cells or cell clumps, based on a change in impedance across a narrow orifice as a cell passes through. Conventionally, an impedance counter consists of two chambers, each filled with a saline solution and connected via a small orifice. The sample containing cells is introduced into one chamber and passed to the second chamber through the orifice. In the presence of a constant voltage across the orifice, a cell passing individually through the orifice displaces a volume of saline solution and thereby alter the impedance across the orifice. The size of the cell may be related to the voltage pulse generated by passage of the cell through the orifice. As a result, when a cell passes through the orifice, its presence and size can be determined from the resulting voltage pulse.

As impedance technology evolved, automated cell counters were developed that were able to count RBCs, WBCs, and platelets simultaneously on the same instrument. This automation proved to be a great labor savings for clinical laboratories. However, these systems were unable to distinguish among all the different types of white blood cells, and thus were unable to provide a five-part differential count. Furthermore, these instruments were also unable to distinguish between reticulocytes and normal red blood cells, and thus could also not provide a reticulocyte count.

Flow cytometry is a powerful method of analysis that is able to determine the cellular content of various types of samples, and in particular samples that contain living cells. In clinical applications, flow cytometers are useful for lymphocyte counting and classification, for immunological characterization of leukemias and lymphomas, and for cross-matching tissues for transplants. In most flow cytometry techniques, cells in a fluid solution are caused to flow individually through a light beam, usually produced by a laser light source. As light strikes each cell, the light is scattered and the resulting scattered light is analyzed to determine the type of cell. Different types of cells produce different types of scattered light. The type of scattered light produced may depend on the degree of granularity, the size of the cell, etc. Cells in a fluid solution may also be labeled with a marker linked to a fluorescent molecule, which fluoresces when light strikes it and thereby reveals the presence of the marker on the cell. In this fashion, information about the surface components of the cell can be obtained. Examples of such fluorescent molecules include FITC (fluorescein isothiocyanate), TRITC (tetramethyl rhodamine isothiocyanate), Cy3, Texas Red (sulforhodamine 101), and PE (phycoerythrin). In addition, intracellular components of the cell, such as nucleic acids, may be stained by fluorescent compounds, and subsequently detected by fluorescence. Examples of such compounds include ethidium bromide, propidium iodide, YOYO-1, YOYO-3, TOTO-1, TOTO-3, BO-PRO-1, YO-PRO-1, and TO-PRO-1. Cells may also be stained with dyes that label particular cellular components, and the absorbance of the dye bound to the cells measured.

Blood cell measurements made using flow cytometry often require two separate measurements—one to measure the RBCs and platelets, and the other to measure WBCs. The reason for separate measurements is that the RBCs are present in the blood at a much higher concentration than other blood cell types, and thus detection of other cell types in the presence of RBCs requires that the RBCs either be removed or large volumes of sample be measured. Alternatively, these cells may be distinguished on the basis of immunochemical staining of particular cell surface antigens and/or differential cell type staining. Thus, U.S. Pat. No. 5,047,321 (Loken et al.) describes a single step method for the analysis of blood cells that uses at least two fluorescent dyes and a labeled cell marker to differentiate the cell types. However, unless two separate dilutions of the same sample are performed, the method requires large volumes of sample to provide sufficient statistical data with regard to the less common blood components.

Light scattering measurements are widely used in flow cytometry to measure cell sizes and to distinguish among several different types of cells. It is known that incident light is scattered by cells at small angles (approximately 0.5–20°) from the line traveled by the incident light that interrogates the cells, and that the intensity of the scattered light is proportional to the cell volume. The light scattered at small angles is referred to forward scattered light. Forward scattered light (also called forward light scatter, or small-angle scatter for angles of scatter between 0.5–2.0°) is useful in determining cell size. The ability to measure cell size depends on the wavelength employed and the precise range of angles over which light is collected. For example, material within cells having a strong absorption at the illuminating wavelength may interfere with size determination because cells containing this material produce smaller forward scatter signals than would otherwise be expected, leading to an underestimate of cell size. In addition, differences in refractive index between the cells and the surrounding medium may also influence the small-angle scatter measurements.

In addition to forward scattered light, cells having a high degree of granularity, such as granulocytes, scatter incident light at high angles to a much greater degree than cells with low granularity, such as lymphocytes. Different cell types may be distinguished on the basis of the amount of orthogonal light scatter (also referred to herein as right angle side scatter) they produce. As a result, forward and right angle side scatter measurements are commonly used to distinguish among different types of blood cells, such as red blood cells, lymphocytes, monocytes, and granulocytes.

Additionally, eosinophils may be distinguished from other granulocytes and lymphocytes on the basis of polarization measurements of right angle side scatter. Normally, incident polarized light is scattered orthogonally and remains polarized. However, eosinophils cause incident polarized light scattered orthogonally to become depolarized to a greater degree than other cells. This higher degree of depolarization permits the specific identification of eosinophil populations in blood samples. Copending U.S. patent application Ser. No. 09/507,515, filed Feb. 18, 2000, and incorporated herein in its entirety, discloses an improved high numerical aperture flow cytometer that employs a high angle side scatter light detector to detect eosinophils in a blood sample. However, the use of a high angle side scatter light detector (at angles of about 130°) enables greater discrimination of eosinophils in blood cell populations. In contrast to conventional systems, the system described in copending U.S. patent application Ser. No. 09/507,515 does not require the incident light to be unpolarized.

U.S. Pat. No. 5,492,833 (Rodriguez et al.) discloses a method for distinguishing erythrocytes from reticulocytes by treating the cells with a ghosting reagent, then measuring light scatter. U.S. Pat. No. 5,559,037 (Kim et al.) discloses a method for counting nucleated red blood cells (NRBCs) by first lysing red blood cells, then exposing the NRBCs to a nuclear stain and measuring fluorescence and light scatter. U.S. Pat. No. 5,733,784 (Studholme et al.) teaches a method for measuring the reticulocyte concentration in a blood sample that uses a reticulocyte staining reagent that is incubated for a period between 15 minutes and 4 hours before light scatter measurements are taken. U.S. Pat. No. 5,879,900 (Kim et al.) discloses a method for simultaneous and quantitative analysis of damaged WBCs, NRBCs, and WBC subpopulations that employs multi-dimensional light scatter and fluorescence measurements. U.S. Pat. No. 5,891,734 (Gill et al.) discloses a system for differentiating blood cells in a blood sample that aspirates a portion of blood and mixes it with a fluorescent reagent, then automatically runs the stained sample through a flow cytometer and measures multi-angle light scatter and fluorescence.

Hemoglobin (HGB) concentration is a common hematology parameter that is generally measured by light absorption at 540 nm. To accomplish this measurement, red blood cells are generally lysed in a solution containing 1 part whole blood to 250 parts lyse solution. This solution may also contain a low level of a cyanide salt (i.e., KCN). The cyanide reduces the hemoglobin in the blood (oxyhemoglobin and deoxyhemoglobin) to hemoglobincyanide, which absorbs maximally at 540 nm. This absorption measurement is conventionally made in a 1.0 cm square cuvette (NCCLS Standard No. H9-A), but other variants from the standard also work with high correlation to the reference method.

In conventional hematology instruments, the hemoglobin concentration is generally measured in an otherwise clear solution, and is referenced to a clear fluid. Lysis of red cells allow the hemoglobin to be measured in the same fluidic channel as the white blood cells. Alternatively, on some systems, the hemoglobin content may be measured in a separate channel.

To obtain meaningful information about the numbers and types of cells in a biological sample, or of the concentration of markers on cell surfaces, the samples must be standardized with respect to the amount of light scatter, fluorescence or impedance associated with standardized populations of the cells. In addition, the flow cytometry instrument itself must be calibrated to ensure proper performance. Calibration of the instrument is typically accomplished by passing standard particles through the instrument, and measuring the resulting scatter, fluorescence, or impedance. Flow cytometers may be calibrated with either synthetic standard materials (e.g., polystyrene latex beads) or with cells or other biological material (e.g., pollen, fixed cells, or stained nuclei). These standardization materials are desirably extremely uniform in size, and contain precise amounts of fluorescent molecules to serve in calibrating the photomultiplier tubes used in detection of fluorescent probes. However, the calibration procedures are lengthy and complicated, and require extensive training to perform properly. Consequently, these calibration procedures are typically performed only once at the beginning of the analysis. Changes in the instrument or in the sample may alter the performance of the instrument.

U.S. Pat. No. 5,627,037 (Ward et al.) discloses a one-step method for determining absolute numbers of one or more populations of reticulocytes and/or leukocytes in a whole blood sample, using flow cytometry. The method comprises mixing a blood sample with a diluent containing a fixative, one or more fluorescent cell markers and a known number of fluorescent microparticles per unit volume, and thereafter analyzing the sample by flow cytometry. The number of cells and the number of microparticles provide a ratio that can be used, knowing the number of microparticles per unit volume and the total sample volume, to calculate the absolute number of cells in the whole blood sample.

U.S. Pat. No. 5,380,663 (Schwartz et al.) discloses a method for calibrating a flow cytometer which employs combined populations of fluorescent microbeads and a software program matched to each combined population of microbeads. U.S. Pat. No. 5,451,525 (Shenkin et al.) discloses a method for determining the total number of cells in a sample that does not require a known sample volume. The method employs a known number of discrete particles which are added to a blood specimen before the specimen is assayed in a flow cytometer.

Flow cytometry techniques that took advantage of the light scattering characteristics of cells were applied beginning in the early 1970's to perform white cell differential analysis, in combination with CBC determination. Automated reticulocyte analysis was developed in the 1980's. However, these early systems did not perform a CBC or white blood cell differential. Eventually, manufacturers like Technicon (Bayer), Coulter (Beckman-Coulter) and Abbott incorporated reticulocyte counting with their automated CBC/white cell differential systems, in such high-end hematology systems as the Technicon (Bayer) H*3, Bayer Advia 120®, Coulter STKS®, Coulter GenS™, and Abbott Cell-Dyn 3500 and CellDyn 4000. These high-end instrument systems are capable of measuring all of the parameters for a complete hematology analysis that are clinically important for patient assessment, namely, CBC, five-part WBC differential and reticulocyte count.

However, these instruments require complex and expensive optical systems to make such measurements. Furthermore, to reduce the effects of their high initial costs, these hematology instruments are designed to be high-throughput machines. Consequently, multiple different specimen samples are often processed simultaneously, and these samples require different combinations of treatments and analyses. For example, analysis of red blood cells and white blood cells require different reagent systems, and are usually optimized in such instruments by using completely different hydraulic paths for each type of analysis. As a result, to simultaneously perform both red blood cell and white blood cell analyses for a given sample, completely separate and distinct hydraulic paths are created for each type of sample. This combination of multiple sample hydraulic paths creates an undesirably high level of complexity, due to the requirement for large numbers of valves, vacuum lines, reaction chambers, syringes, vacuum pumps, miniature orifices, and the like.

In addition, a significant amount of training is required to learn how to use these instruments properly. Furthermore, these instrument systems require service several times a year, at a minimum. As a result, the high costs associated with purchasing, operating and maintaining these high-end instruments make them financially inaccessible to small clinics and doctor's offices. Doctors can obtain limited access to these instruments by contracting with commercial laboratories that will pick up blood samples from the clinic or doctor's office and transport the samples back to the laboratory for analysis on these high-end hematology systems. The results are then sent to the doctor. This process is very time-consuming, and usually the doctor will not have the results until the following day, at the earliest.

Thus, if a doctor desires a complete hematology assessment (CBC, five-part WBC differential, and reticulocyte count) quickly, the in-office laboratory must perform some combination of manual methods. Instrumentation, such as impedance counters that perform CBC with limited WBC differentials, are available for these in-clinic laboratories, but systems that can produce five-part differentials and reticulocyte counts are not. Thus, to obtain values for these parameters, manual methods are employed. These manual methods, however, are slow, labor-intensive, and prone to operator error.

The low-end impedance counters available to the clinics and doctor's offices includes such systems as the Abbott 1200, ABX Micros, and the Sysmex K-21. While the high-end hematology systems advanced by incorporating flow cytometric techniques and other improvements, the technology used in the low-end systems has changed very little. These low-end instruments have become much more compact and efficient through incorporation of semiconductor microelectronics where applicable; however, in the end, these systems are functionally no different from the impedance counters used by clinical laboratories in the late 1970's and early 1980's. In particular, these instruments still cannot perform a five-part WBC differential, nor can they produce a reticulocyte count.

Low-end impedance instruments used in small clinics and doctor's offices generally use bulk reagent packs that are intended for larger laboratories. Since the number of samples run on these instruments is low compared to their laboratory counterparts, significant volumes of reagents are wasted in performing startup and shutdown cycles, as well as in system cleanings between samples. Thus, it is impossible to predict how many patient samples a user will get from a reagent pack. As a result, the user must maintain an excess amount of reagents on hand, leading inevitably to a substantial degree of reagent waste. In addition, the hydraulics of these instruments, though generally less complex than the high-end laboratory systems, are still prone to the same reliability issues associated with the use of high numbers of vacuum lines, valves, and vacuum pumps, as well as with the small dimensions of the apertures used to count cells. Thus, for in-clinic and in-office applications, such low-end impedance instruments are severely deficient in producing the results needed for complete hematology analyses, are inefficient in their use of reagents, and have the same inherent reliability problems that are associated with high-end biological fluid analysis systems.

Some attempts have been made to address the clinical blood sample analysis needs of small laboratories and doctor's offices, but these efforts have met with only limited success. For example, the QBC® technology, developed by Becton-Dickinson, does not require flow cytometry or other expensive technology. The major moving part required is a centrifuge that forces the cellular components of blood to layer in an oversized, precisely bored capillary tube. Inside the capillary tube, a plastic "float" that is precisely manufactured for size and density characteristics establishes density equilibrium within the white blood cell and platelet layers, thereby expanding the height of the layers by about ten fold. This system provides fairly accurate estimates of platelet count, WBC count, and a two-part WBC differential (granular and agranular leukocytes), as well as a very accurate measurement of hematocrit. The QBC® system does not utilize any liquid reagents, and is therefore very reliable. This method is also a unit dose method, in that a single capillary tube and float are used for each analysis. As a result, there is no wasted reagent.

While the QBC® technology addresses concerns of reliability and reagent waste for the in-clinic user, it falls well short of delivering the required parameters for a CBC, produces an incomplete differential, and does not quantify reticulocytes. Additionally, the precision and accuracy of the parameters produced by the QBC® system, except for hematocrit, are worse than those of the low-end impedance systems. Consequently, there remains a great need for an inexpensive and reliable biological fluid analysis system that is capable of producing the parameters that are relied upon by clinicians and doctors in making decisions that affect the treatment of a large percentage of their patients.

To address the need for such an instrument capable of providing hematology parameters that cannot be provided by low-end impedance instruments in an in-clinic setting, several major factors have to be considered. The size, cost and complexity of subsystems associated with high-end hematology systems must be reduced, while retaining the ability of the system to perform high-throughput blood analyses.

The major sub-systems that contribute to the cost and complexity of the high-end flow cytometry-based hematology systems are the light source, the optics system, and the fluid handling system. The gas lasers conventionally employed in flow cytometer-based hematology systems produce strong light signals, but high levels of noise associated with these lasers have minimized their utility for use in flow cytometry-based hematology systems. This can be offset by utilizing longer plasma tubes, as the longer the plasma tube the lower the noise level, and thus the greater the S/N ratio. However, this results in greater cost for the system. Incorporation of a laser diode in place of a conventional gas laser significantly reduces the total package size and cost. Diode lasers have inherently lower noise levels than gas lasers. However, the optical characteristics of laser diodes are not as desirable as those of gas lasers. Laser diodes are astigmatic, and have temperature-dependent and current-dependent noise regions, which causes a phenomenon referred to as "mode-hopping". Subtle temperature or electrical current changes cause the laser diode to abruptly change from one single mode state to another single mode state. When mode hops are occurring, the S/N ratio of the light measurement is very low, making it useless for measuring small particles (i.e., platelets), or to distinguish subtle difference in larger ones.

Precise temperature control and current control may be implemented to reduce mode hopping. However, this process requires that each laser diode be individually characterized to find a quiet temperature/current area where mode-hopping does not occur. Laborious effort is required to characterize each individual laser diode to find the ideal temperature and current settings. In addition, as the laser ages, the quiet temperature/current area changes, and resetting the temperature and current controls is required. Furthermore, even if the ideal external temperature is determined, maintaining a constant temperature is complicated by the significant amount of heat produced when the diode laser is first turned on. As a result, temperature equilibrium of the diode laser can take up to 30 minutes to establish, even if the diode laser and temperature control system are working properly. This equilibration time decreases the useful life of the laser. Lastly, the implementation of temperature control severely limits the operating temperatures at which a unit can be used, and adds significant cost and size to a relatively inexpensive and small laser diode.

Significant costs and complexity in the optics system of flow cytometry-based hematology instruments are associated with the light beam shaping optics and the light collection optics. Beam shaping optics are used to alter the power distribution of a laser beam from a circular gaussian distribution to an ellipsoid distribution, where the power distribution is both more intense and more evenly distributed over the area of interest. Many hematology instruments use a collimated approach, where the "tails" of the gaussian power distribution curve are blocked, e.g., by an aperture. This creates a top hat effect, which provides uniformity over the region of interest and laser pointing stability while reducing the need for fluidic control. However, this approach reduces power density at the interrogation point in the flow cell.

Light beam shaping optics are also involved in the creation of a very thin light beam, sub-cellular in size (i.e., <4 microns), which is useful for time-of-flight (TOF) measurements and for maximizing power density at the point of cell interrogation. TOF measurements can be useful to distinguish bioparticles based on their sizes. Conventionally, the initial laser beam is first expanded, then focused to a small spot size. Both the expansion step and the focusing step are conventionally accomplished by using various optical elements, such as lenses, beamsplitters, apertures, and mirrors. Significant costs are incurred by the need to incorporate many expensive optical components. In addition to the high cost of each of these components, each optical component also must be held securely in space, and carefully aligned in three-dimensional space with the other components of the optic system. These steps add additional complexity and cost to the overall design.

Light collection optic systems in flow cytometry-based hematology systems are even more complex than the light beam shaping optics. This is because in almost all applications, more than one measurement of light is made. To accomplish this, two or more detection sources are needed. Each detector requires several optic components that collect and steer scattered light to the detector. As in the beam shaping case, significant costs are incurred by the requirement for numerous optical components, each of which needs to be held in space and carefully aligned.

Conventional hematology systems that automatically create a dilution of a whole blood sample generally do so in at least two separate steps. These two steps may be performed either serially or in parallel. Whether performed serially or in parallel, a minimum of two reaction chambers are utilized. One chamber may be used for counting and sizing of RBCs, while the other chamber may be used for counting and classifying WBCs. In some instruments, an additional chamber is added, for example to perform analyses of hemoglobin concentration. The reaction chambers used in conventional hematology systems are usually contained within the instrument, and must be rinsed between samples to prevent sample carryover.

In order to perform these tasks in the reaction chambers, a multitude of fluid handling components are required. These components include, for example, pressure pumps, to move diluent or cleaning solution around the system; vacuum pumps, to remove fluid from the reaction chambers; valves, to control the movement of fluids; metering devices, to precisely aliquot sample and reagents to the reaction chambers; and tubing to connect all the fluid handling components. The sheer number of components involved in the conventional hematology systems add greatly to the cost, and reduce the reliability, of such devices.

SUMMARY OF THE INVENTION

The device of the present invention is a flow-cytometry based bioparticle analysis system that combines unconventional flow cytometry light scatter measurement techniques with a unique approach to reagent delivery and sample processing that minimizes reagent waste and reduces systems and operational costs. More particularly, the present invention is directed to a flow cytometry-based hematology system that employs a set of selected features which, in combination, provide at least a complete blood count, a five-part differential white blood cell count, and a reticulocyte count in a system that is small, reliable, and inexpensive enough to be well suited for use in small clinical laboratories, doctor's offices, veterinarian offices, and the like. The system may be used in the analysis of whole blood samples, or in blood-derived samples, such as, for example, platelet-rich plasma, packed red blood cells, and the like. The system may also be used in the analysis of any biological sample other than blood or blood-derived products (e.g., urine) that is amenable to analysis by standard flow cytometry techniques. The present invention also relates to methods for use of the flow cytometry-based blood sample analysis system.

This present invention is a flow cytometry-based hematology system that includes a lensless optical detection system for collection of light emitted from a laser light source, after interacting with a cell or particle. The use of a photodetector array that collects multiple light measurements without the need for any moving parts, lenses or other types of optical components greatly increases the reliability of the system. The photodetector array is preferably such that various types of scattered light are detectable, and the data collected provides a complete hematological analysis when used in combination with a high numerical aperture technique for right angle scatter. The laser light source may be a standard diode laser light source that is shaped to produce a thin line, as disclosed in U.S. Pat. No. 6,612,719. The diode laser reduces the size and complexity of the system. Mode-hopping, a problem that occurs with diode lasers, may be reduced significantly by the application of a high-frequency modulation technique. Finally, the system preferably uses a unique system of consumable reagent tubes that act as disposable reaction chambers, mixing chambers, and waste chambers for the blood sample analyses. The consumable tubes incorporate polystyrene latex particles or the like (i.e., fixed cells), which act as internal standards to ensure that the dilutions made during processing of the samples have been carried out correctly. The use of these consumable tubes results in less waste, greater reliability, and greatly improved accuracy and validation of the results.

Accordingly, one object of the present invention is to provide a lensless light detection system for a flow cytometer.

It is another object of the present invention to provide a lensless light detection system that comprises a photodetector array on an integrated circuit chip which is effective to measure at least one of axial light loss, low-angle forward scattered light, and high-angle forward scattered light.

It is another object of the present invention to provide a lensless light detection system that comprises a photodetector array, arranged on a plurality of electrically distinct integrated circuit chips, which is effective to measure at least one of axial light loss, low-angle forward scattered light, and high-angle forward scattered light.

It is another object of the present invention to provide a disposable vessel for use in a flow cytometry-based hematology system that comprises a tube; a known number of reference particles in the tube, each of the reference particles having a predetermined diameter such that, when the reference particles are illuminated by light, the light is scattered by the reference particles such that the scattered light falls into at least one of a plurality of predetermined light scatter channels; and at least one reagent.

It is another object of the present invention to provide a disposable vessel for use in a flow cytometry-based hematology system that comprises a tube; a known number of reference particles in the tube, each of the reference particles having one of several diameters such that, when the reference particles are illuminated by light from a laser, the light is scattered by the reference particles such that the scattered light falls into one of a plurality of predetermined light scatter channels; and at least one reagent.

It is another object of the present invention to provide a method for analyzing a blood sample or a blood-derived sample using a flow cytometry-based hematology system that comprises mixing the blood sample or blood-derived sample with a reagent in a disposable vessel containing a known number of reference particles, the reference particles having one of several diameters such that when the reference particles are illuminated by light, the light is scattered such that the scattered light falls into one of a plurality of predetermined light scatter channels; standardizing the sample using the reference particles in the disposable vessel containing the portion by measuring at least one of axial light loss, low-angle forward scattered light, high-angle forward scattered light, right angle scattered light, and time-of-flight for each of the reference particles, and comparing the measurements to predetermined values obtained for the reference particles; counting cells from the sample; measuring at least one parameter from the group consisting of axial light loss, low-angle forward scattered light, high-angle forward scattered light, right angle scattered light, and time-of-flight for each cell in the sample, to produce a measurement value for each parameter; and analyzing the measurement values to classify each cell.

It is another object of the present invention to provide a method for analyzing a blood sample or a blood-derived sample using a flow cytometry-based hematology system that comprises mixing a first portion of the blood sample or blood-derived sample with a reagent in a disposable vessel containing a known number of reference particles to form a red cell solution, the reference particles having one of several diameters such that when the reference particles are illuminated by light, the light is scattered such that the scattered light falls into one of a plurality of predetermined light scatter channels; standardizing the red cell solution and the flow cytometry-based hematology system using the reference particles in the disposable vessel containing the portion by measuring at least one of axial light loss, low-angle forward scattered light, high-angle forward scattered light, right angle scattered light, and time-of-flight for each of the reference particles, and comparing the measurements to predetermined values obtained for the reference particles; counting red blood cells, reticulocytes, and platelets from the red cell solution; measuring at least one parameter from the group consisting of axial light loss, low-angle forward scattered light, high-angle forward scattered light, right angle scattered light, and time-of-flight for each cell in the red cell solution, to produce a red cell solution measurement value for each parameter for each of the red blood cells, reticulocytes, and platelets from the sample; mixing a second portion of the blood sample or blood-derived sample with a lyse solution in the disposable vessel containing a known number of reference particles to form a white cell solution; counting white blood cells from the white cell solution; measuring at least one parameter from the group consisting of axial light loss, low-angle forward scattered light, high-angle forward scattered light, right angle scattered light, and time-of-flight for each cell in the white cell solution, to produce a white cell solution measurement value for each parameter for the white blood cells; analyzing the red cell solution measurement values and the white cell solution measurement values to classify each cell.

It is another object of the present invention to provide a method for analyzing a blood sample or a blood-derived sample using a flow cytometry-based hematology system that comprises mixing the blood sample or blood-derived sample with a reagent in a disposable vessel containing a known number of reference particles, the reference particles having one of several diameters such that when the reference particles are illuminated by light, the light is scattered such that the scattered light falls into one of a plurality of predetermined light scatter channels; standardizing the sample using the reference particles in the disposable vessel containing the portion by measuring at least one of axial light loss, low-angle forward scattered light, high-angle forward scattered light, right angle scattered light, and time-of-flight for each of the reference particles, and comparing the measurements to predetermined values obtained for the reference particles; counting cells from the sample; measuring at least one parameter for the sample by using one of a platelet aggregation assay and a clottable assay, to produce a measurement value for each parameter; and analyzing the measurement values.

It is another object of the present invention to provide a flow cytometry-based hematology system for classifying and counting biological cells in a blood sample or blood-derived sample that comprises a disposable vessel, the disposable vessel containing a known number of reference particles and at least one reagent, the reference particles having one of several diameters such that when the reference particles are illuminated by light, the light is scattered such that the scattered light falls into at least one of a plurality of known light scatter channels; a lyse tube, the lyse tube containing at least one lyse reagent capable of lysing red blood cells that may be present in the blood sample or blood-derived sample while leaving white blood cells in the blood sample or blood-derived sample substantially intact for a period of at least one minute; a sheath tube, the sheath tube containing a sheath solution capable of acting as a sample dilution reagent, a sheath reagent, and a washing reagent for a hydraulic path of the flow cytometry-based hematology system; a flow cell; a hydraulic system, the hydraulic system being capable of mixing the blood sample or blood-derived sample with one or more of the contents of the disposable vessel, the lyse tube and the sheath tube, and being capable of moving one or more of the disposable vessel, the lyse tube, the sheath tube, or a mixture of the blood sample or the blood-derived sample with one or more of the contents of the disposable vessel, the lyse tube and the sheath tube through the flow cell; a diode laser, the diode laser emitting light to irradiate cells derived from the blood sample or the blood-derived sample in the flow cell; a lensless light detection system, the lensless light detection system having a first portion capable of collecting one or more of axial light loss, low-angle scattered light and high-angle scattered light scattered by the cells in the flow cell when the cells in the flow cell are irradiated by the laser, and a second portion capable of collecting right angle scattered light scattered at a high numerical aperture, the second portion being physically distinct from the first portion, the first portion and the second portion converting the axial light loss, the low-angle scattered light, the high-angle scattered light, and the right angle scattered light into electrical signals; and a signal processor, the signal processor being capable of analyzing the electrical signals generated from the first portion and the second portion of the lensless optical module, and generating data therefrom.

It is another object of the present invention to provide a flow cytometry-based hematology system for classifying and counting biological cells in a blood sample or blood-derived sample that comprises a disposable vessel, the disposable vessel containing a known number of reference particles and at least one reagent, the reference particles having one of several diameters such that when the reference particles are illuminated by light, the light is scattered such that the scattered light falls into one of a plurality of predetermined light scatter channels; a lyse tube, the lyse tube containing at least one lyse reagent capable of lysing red blood cells that may be present in the blood sample and blood-derived sample while leaving white blood cells in the sample substantially intact for a period of at least one minute; a sheath tube, the sheath tube containing a solution capable of acting as a sample dilution reagent, a sheath reagent, and a washing reagent for a hydraulic path of the flow cytometry-based hematology system; a flow cell; a hydraulic system, the hydraulic system being capable of mixing the blood sample or blood-derived sample with one or more of the contents of the disposable vessel, the lyse tube, and the sheath tube, and being capable of moving one or more of the contents of the disposable vessel, the lyse tube, the sheath tube, or a mixture of the blood sample of the blood-derived sample with one or more of the contents of the disposable vessel, the lyse tube, and the sheath tube through the flow cell; a diode laser, the diode laser emitting light to irradiate cells from the blood or blood-derived sample in the flow cell; a lensless light detection system, the lensless light detection system having a first portion capable of collecting axial light loss, low-angle forward scattered light, and high-angle forward scattered light, and a second portion capable of collecting right angle scattered light scattered at a high numerical aperture; and a signal processor, the signal processor being capable of analyzing one or more signals generated from the first portion and the second portion of the lensless light detection system, and generating data therefrom.

The above and other objects, features and advantages of the present invention will become apparent from the following description read in conjunction with the accompanying drawings.

BRIEF DESCRIPTION OF THE DRAWINGS

FIG. 10B depicts the extinction or axial light loss channel (EXT) data on the x-axis.

FIG. 10C depicts the right angle scatter channel (RAS) data on the x-axis.

FIG. 10C depicts the time-of-flight (TOF) or pulse width measurement on the x-axis. Pulse width measurements can be obtained from any of the channels that utilize a photodetector, but it is preferred to use either the EXT channel or the FSL channel.

FIG. 15 shows the separation of reticulocyte population from the main population of mature red blood cells. The calculated value of 1.72% reticulocytes is in excellent agreement with the value of 1.60% obtained using a manual reference method.

DETAILED DESCRIPTION OF THE PREFERRED EMBODIMENTS

Figure 1:
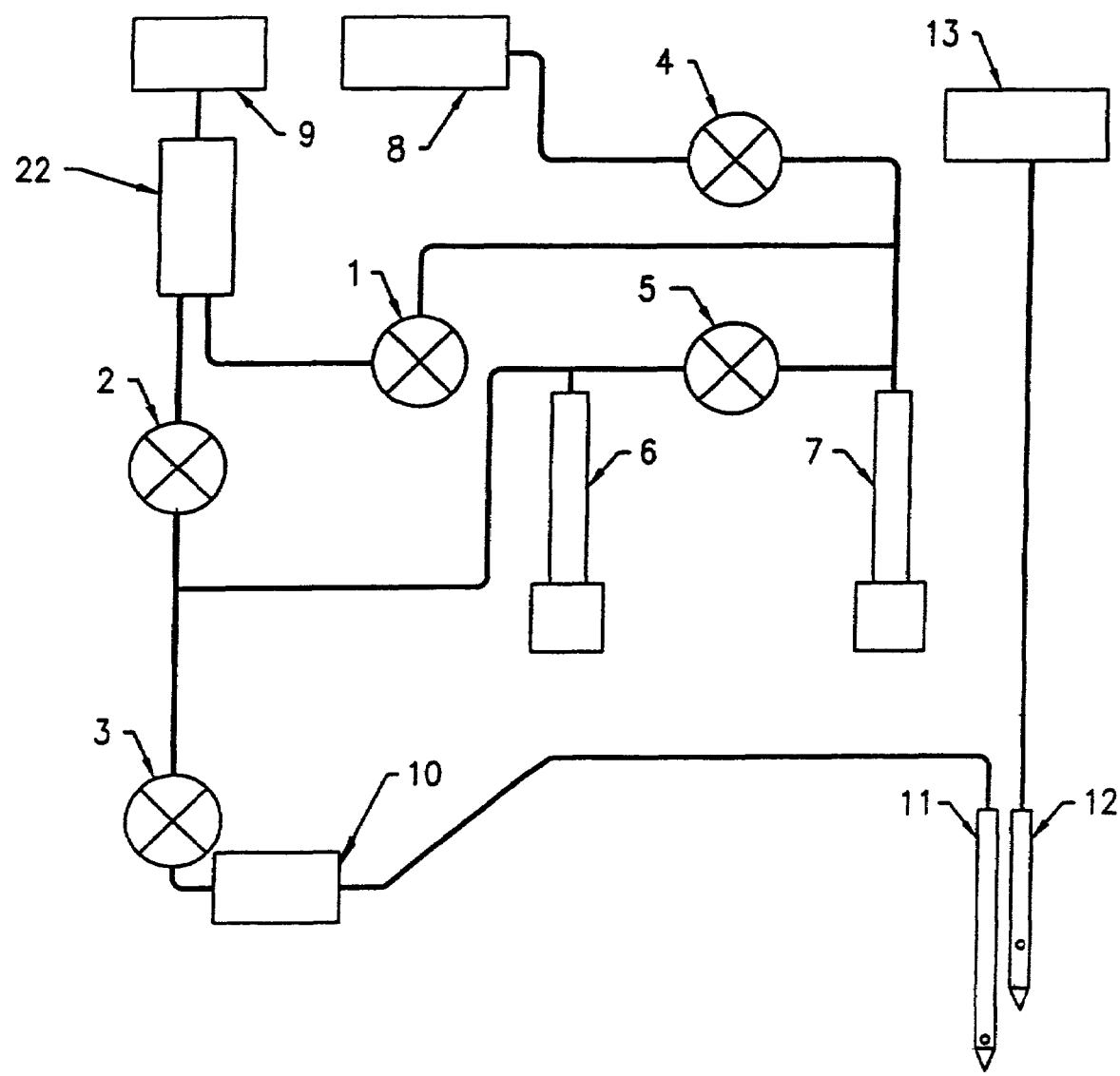
FIG. 1 is a schematic representation of the system hydraulics of a preferred embodiment of the present invention.

The present invention discloses a flow cytometry-based hematology system that is capable of determining at least a complete blood count (CBC), a five-part white blood cell differential, and a reticulocyte count. The system has a high level of reliability, is inexpensive to manufacture and operate, and utilizes very low volumes of method reagents. The system also does not require significant levels of operator training. The system is particularly well suited for use in environments where there is a need for an instrument that can analyze blood samples quickly and inexpensively and provide a complete blood analysis for each sample within minutes of blood draw. Such environments would include, for example, medical clinics, doctor's offices, and veterinary offices.

The flow cytometry-based hematology system of the present invention combines a unique lensless optical detection system with the use of consumable tubes containing reference particles that are used for optical standardization and to check if the instrument is performing dilutions correctly. The system also employs a diode laser having a defined beam shape. The use of a diode laser for small bioparticle analysis, such as platelets, in flow cytometry-based systems has heretofore largely been avoided, due to the propensity of these systems to exhibit periodic noise phenomena. This problem has been overcome through the use of a high frequency modulation technique, discussed in greater detail below. In addition, the flow cytometry-based hematology system of the present invention uses a unique, simplified hydraulics system that does not rely on vacuum pumps or pressure pumps to move fluids in the system. Rather, the system uses motor-driven syringes to move fluids and sample portions within the various elements of the system. Consequently, the number of fluid handling components used in the system is far lower than in conventional systems, and results in a system having increased reliability and reduced cost.

In isolation, each of these component systems, where previously known, has not been thought to confer any advantage or to advance the art of flow cytometry-based hematology systems, because those in the art were focused on increasing sample throughput rates or the number of different types of samples that could be analyzed, to provide a system that could service as many different types of consumers as possible. The system of the present invention, in contrast, differs dramatically from these prior art instruments in that it was conceived and reduced to practice to solve an entirely different problem—how to provide a flow cytometry-based system for analyzing biological fluid samples that was inexpensive enough to manufacture, operate and maintain that medical clinics, doctor's offices and veterinary offices could afford it. The combination of these elements creates a system that can measure at least a complete blood count (CBC), a five-part differential white blood cell count, and a reticulocyte count without the need for fluorescence measurements, and which is much lower in cost and higher in reliability that existing flow-cytometry-based hematology systems. However, the system of the present invention is not precluded from incorporating fluorescence to measure one or more desired parameters, as described herein.

In a preferred embodiment, the flow cytometry-based hematology system first dilutes an aliquot of whole blood into a consumable tube containing an assay reagent and reference particles. The consumable tube may also be referred to herein as a "disposable vessel". The sample is mixed in the consumable tube, and a portion is drawn into the instrument for determination of RBC, platelet, and reticulocyte counts. After the portion is discarded and the system washed, another aliquot of whole blood and an aliquot of a lyse reagent are added to the consumable tube. The RBCs are lysed in this solution, while leaving the WBCs substantially intact for a period of at least one minute. By "substantially intact" in this context it is meant that the WBCs are in their near native state where no structural damage to the outside membrane, or internal structures of the cell are observable. After mixing, a portion of the lysed sample is drawn into the machine for determination of white blood cell content. The lysed sample portion is then discarded into a waste container, and the system washed for the next sample.

The system is able to provide a CBC, a five-part WBC differential and a reticulocyte count. While not being as rapid as the conventional high-throughput flow cytometry-based hematology systems, the system of the present invention is far less expensive to produce, maintain and operate than these devices. The system of the present invention also provides a means to minimize the amount of waste generated, by using a consumable tube that acts as a reagent tube at the start of the assay, a reaction tube during the assay, and a waste tube after the assay is completed. As a result, the amount of reagent wasted is minimized, further enhancing the economy of the system.

Consumable Tube

The first item to be considered as part of the flow cytometry-based hematology system of the present invention is the consumable tube. The consumable tube acts as a disposable mixing and reaction chamber during the assay. The consumable tube may be open or closed, but is preferably a closed tube, and more preferably is a blood sample tube closed by a standard rubber septum, or a septum made from a similar material. The consumable tube contains assay reagents, preferably in an aqueous solution, and preferably also contains reference particles for internal calibration. The assay reagents may be divided among more than one tube, where, for example, the assay requires temporal or physical separation of the reagents. Assay reagents would include, for example, buffers, salts, substrates or indicators necessary or preferred to the assay. Assay reagents would also include reagents that would be specific for a particular assay, such as, for example, antibodies for immunoassays, receptor bodies, enzyme substrates to measure or detect enzyme activities, or ligands to measure receptor binding activities. By "antibodies", it is not meant to limit to any particular form. Rather, such forms could include, without limitation, monoclonal antibodies, polyclonal antibodies, and active fragments, such as F(ab), F(ab')$_2$, scFV, and Fv.

As noted above, the consumable tube acts as an assay reagent tube, a reaction tube, and a waste tube. Each consumable tube has a unique coded label affixed to the outside surface of the tube, as does every other tube placed in the instrument. Preferably, the coded label is a bar-coded label. The consumable tube contains one or more distinct types of particles that are used for count quantification checks, as well as for optical standardization. Each lot of reagents is aliquoted into consumable tubes, along with a defined number of reference particles. These reference particles are capable of scattering incident light into one or more scattered light channels. Such reference particles are known to those in the art and may be, for example, pollen grains, fixed cells (e.g., fixed avian RBCs), large colloids, or synthetic (i.e., polystyrene latex or styrene divinylbenzene latex) particles.

The reference particles are used at known concentration, and act as a cellular surrogate. In other words, the reference particles act as an intra-sample, internal standard for quality control purposes. This ensures that the instrument is performing properly, and that all dilutions have been made correctly. The particle size range is preferably from about 1 micron to about 10 microns, most preferably about 4 microns.

The key to selecting the proper reference particles for the system is that the reference particles must be distinguishable from the sample's target cells on at least one of the axes of optical measurements. The preferred embodiment of the reference particles is polystyrene latex particles. Polystyrene latex particles are commercially available through several manufacturers, such as Seradyn (Indianapolis, Ind., USA) and Duke Scientific (Palo Alto, Calif., USA). Many sizes of polystyrene latex particles are commercially available. The preferred size is 4.0 microns, which is easily distinguished from the cellular components of blood along several axes of data collection in the instrument. Choosing this size for the reference particles allow the reference particle concentration to be easily determined, because such particles have a different index of refraction than that of cellular components. The 4.0-micron particles are distinguishable from red blood cells and platelets on extinction (EXT), low angle forward light scatter (FSL), and right angle scatter (RAS) channels, but overlap with red blood cells on the high angle forward light scatter (FSH) and time-of-flight (TOF) channels. Functionally, it does not matter which axis has the best separation of the reference particle(s). As long as at least one of the five light scatter channels (EXT, FSL, FSH, RAS, or TOF) shows separation between the signals for the reference particles and the signals for the cells, the entire population of particles can be gated and analyzed completely separately from any of the sample cellular components. The reference particles are distinguished from fluorescent standardizing particles, which are often used to standard fluorescent light detectors often used in flow cytometers.

Fixed red blood cells from a variety of different species (e.g., chicken) are also often employed as reference particles. These cells may be completely hidden on all channels during red blood cell analysis, and therefore may not be appropriate for use in detection and counting of red blood cells. However, they are still usable in the detection and counting of white blood cells, since they would be easily distinguished on all channels during white cell analysis in the sample containing lysed RBCs. Fixed red blood cells from avian species offer the added feature of having a nucleus, which helps distinguish them from mammalian red cells on the basis of right angle scatter.

The reagent systems within the consumable are sensitive to a percent solids measurement (volume of particle times concentration of particles); thus, the lower the volume chosen, the higher the concentration of particles, and the broader the range of dilutions that may be practiced. Furthermore, the measured distribution of reference particles forms a Poisson distribution, such that the coefficient of variation (CV) may be calculated by $CV=100\times\sqrt{x}/x$, where CV is expressed as a percent, and x is the number of particles per µl. The final concentration of particles in the consumable tube should be in a range between about 500 per µl and about 100,000 per µl. The preferred embodiment is to have the final concentration of particles in the consumable at about 10,000 per µl, which gives a CV of 1%. More particularly, it is preferred to have a particle count of about 15,000 per µl for RBC counts, and about 10,000 per µl for WBC counts. At this level, the number of reference particle events counted will be within about the same range as the number of white blood cells counted.

Figure 18:
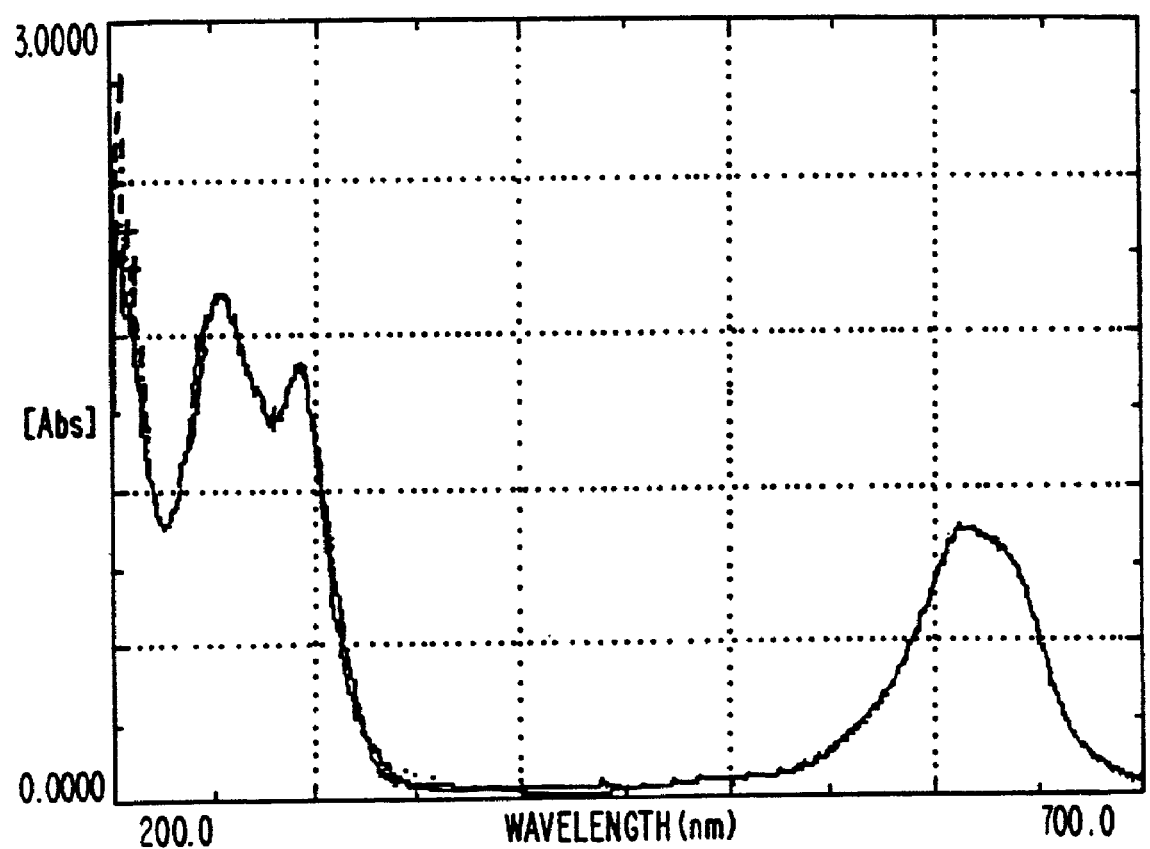
FIG. 18 is a spectrophotometer scan of a new methylene blue reticulocyte dye solution.
Figure 19A:
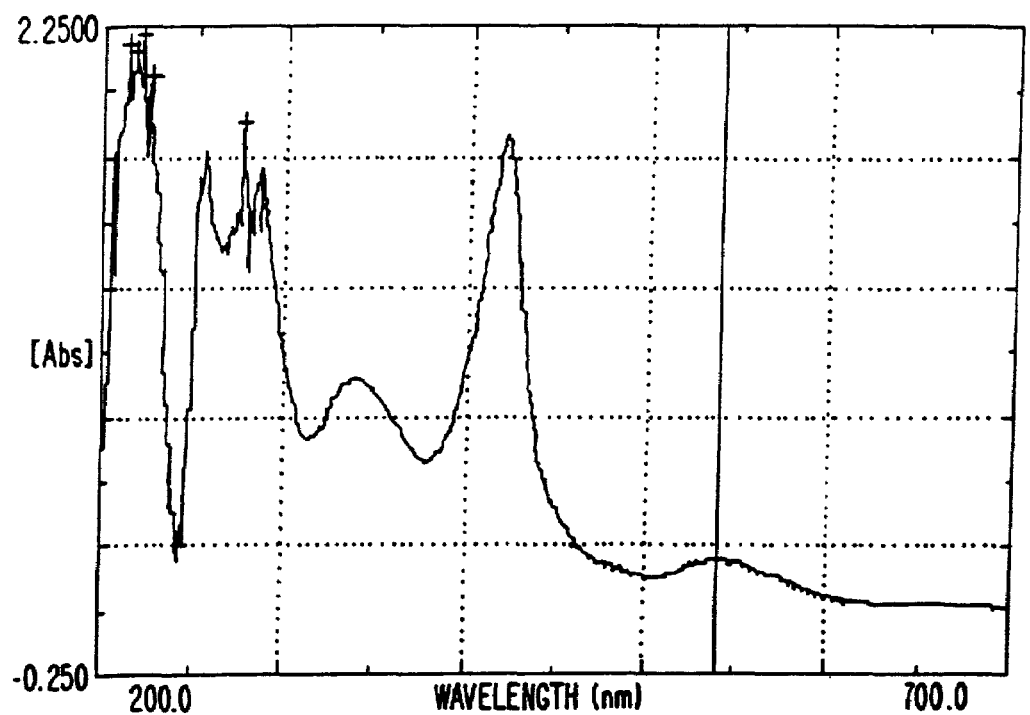
FIG. 19A is a spectrophotometer scan of a whole blood solution lysed in a cyanide solution to measure HGB concentration. The absorbance at 540 nm is read to detect cyanohemoglobin.
Figure 19B:
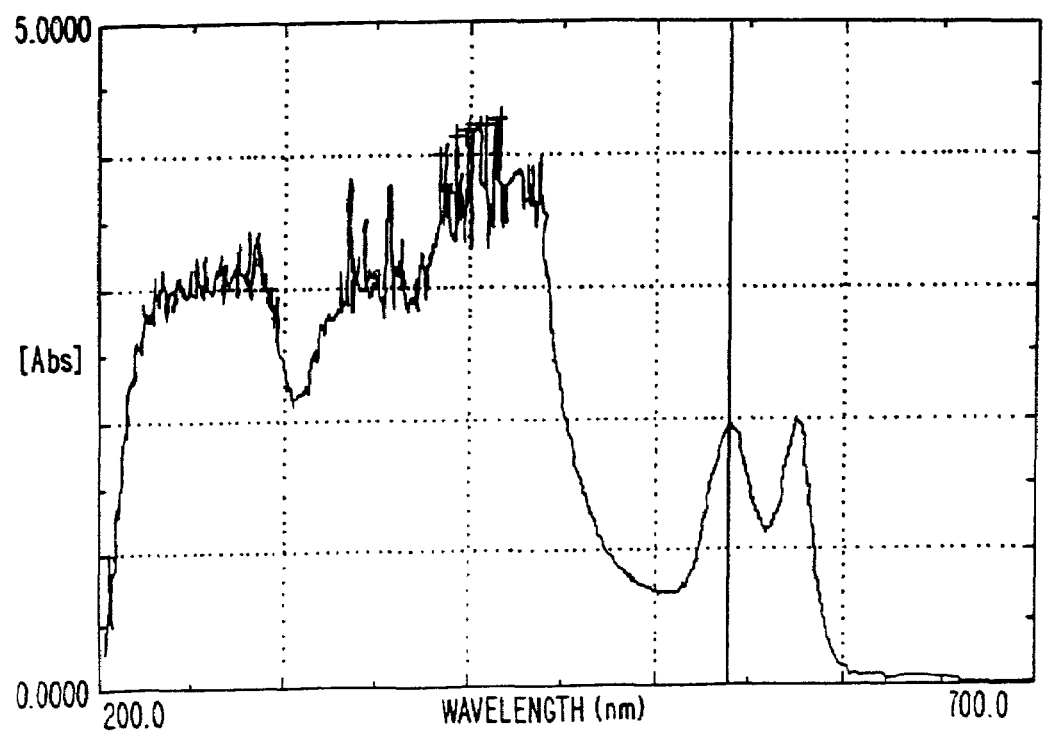
FIG. 19B is a spectrophotometer scan of a whole blood solution in the absence of cyanide. Absorbance at 540 nm indicates the oxyhemoglobin concentration, and absorbance at 580 nm represents the deoxyhemoglobin concentration.
Figure 20:
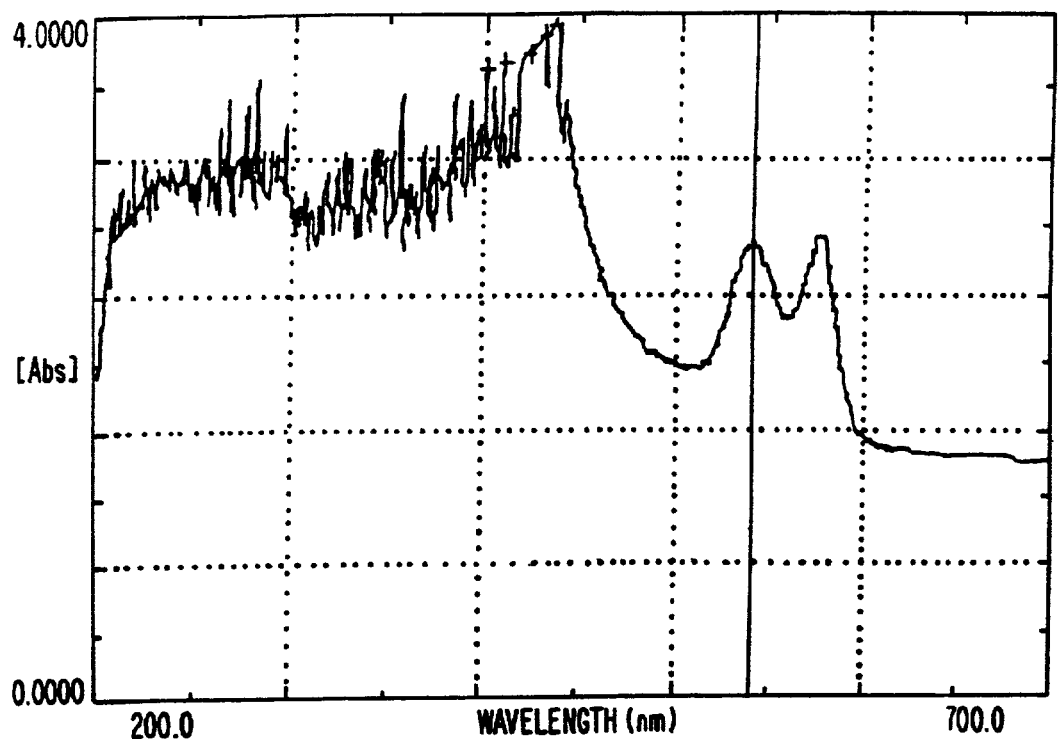
FIG. 20 is a spectrophotometer scan of a diluted, unlysed whole blood solution. The absorbance reading at 540 nm indicates the concentration of oxyhemoglobin, and the absorbance reading at 580 nm indicates the concentration of deoxyhemoglobin.
Figure 21:
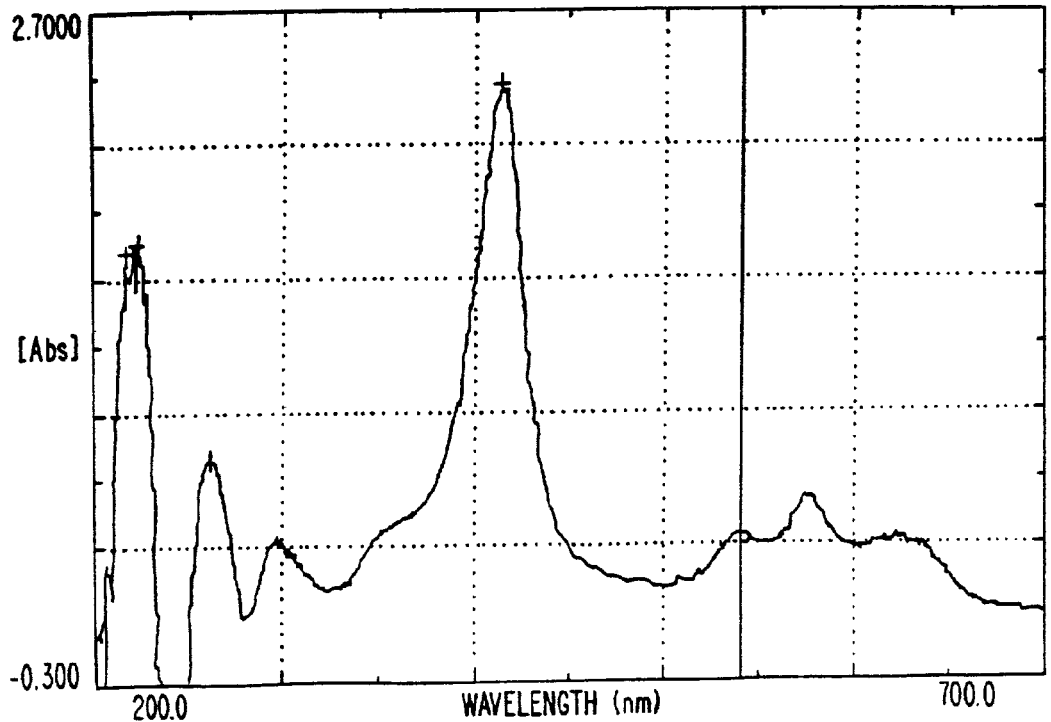
FIG. 21 is a spectrophotometer scan of a solution containing lysed whole blood and new methylene blue reticulocyte dye. This solution is representative of a solution present in consumable tube 63.
Figure 22:
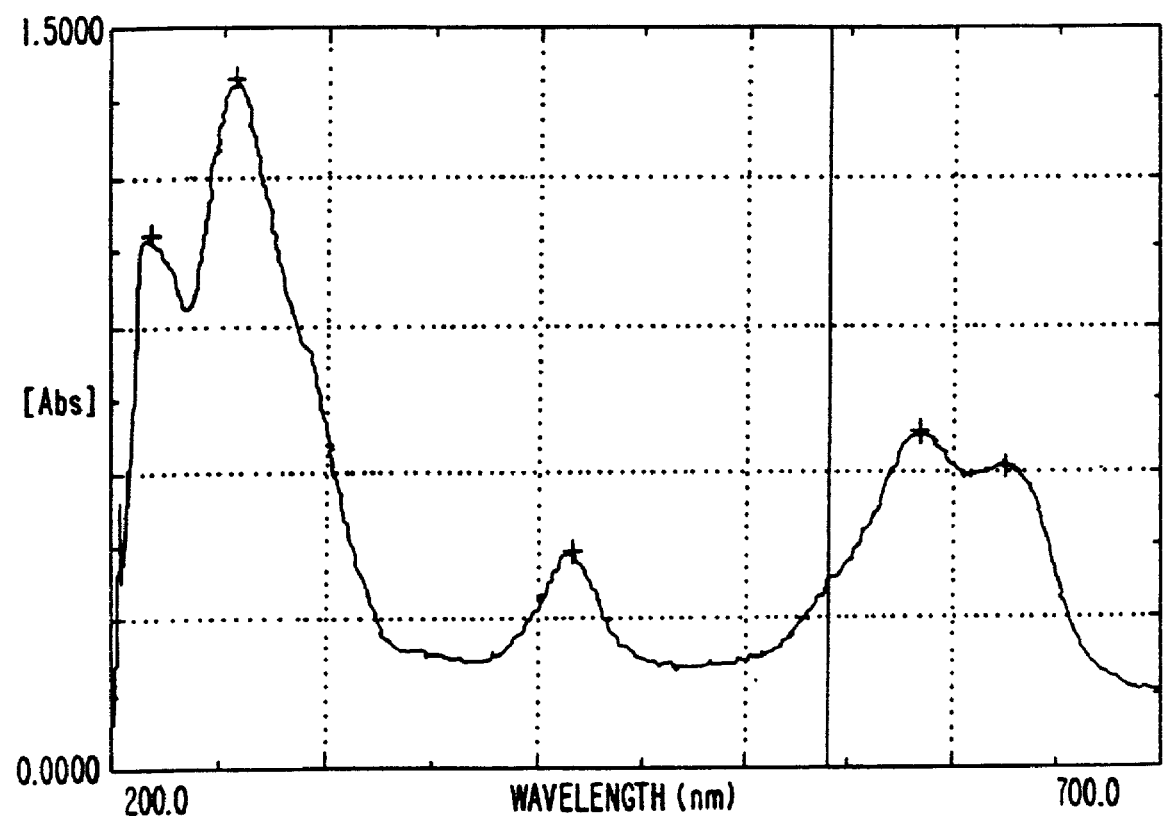
FIG. 22 is a spectrophotometer scan of a solution containing diluted unlysed whole blood and new methylene blue reticulocyte dye. This solution is representative of a solution present in consumable tube 61.
Figure 25:
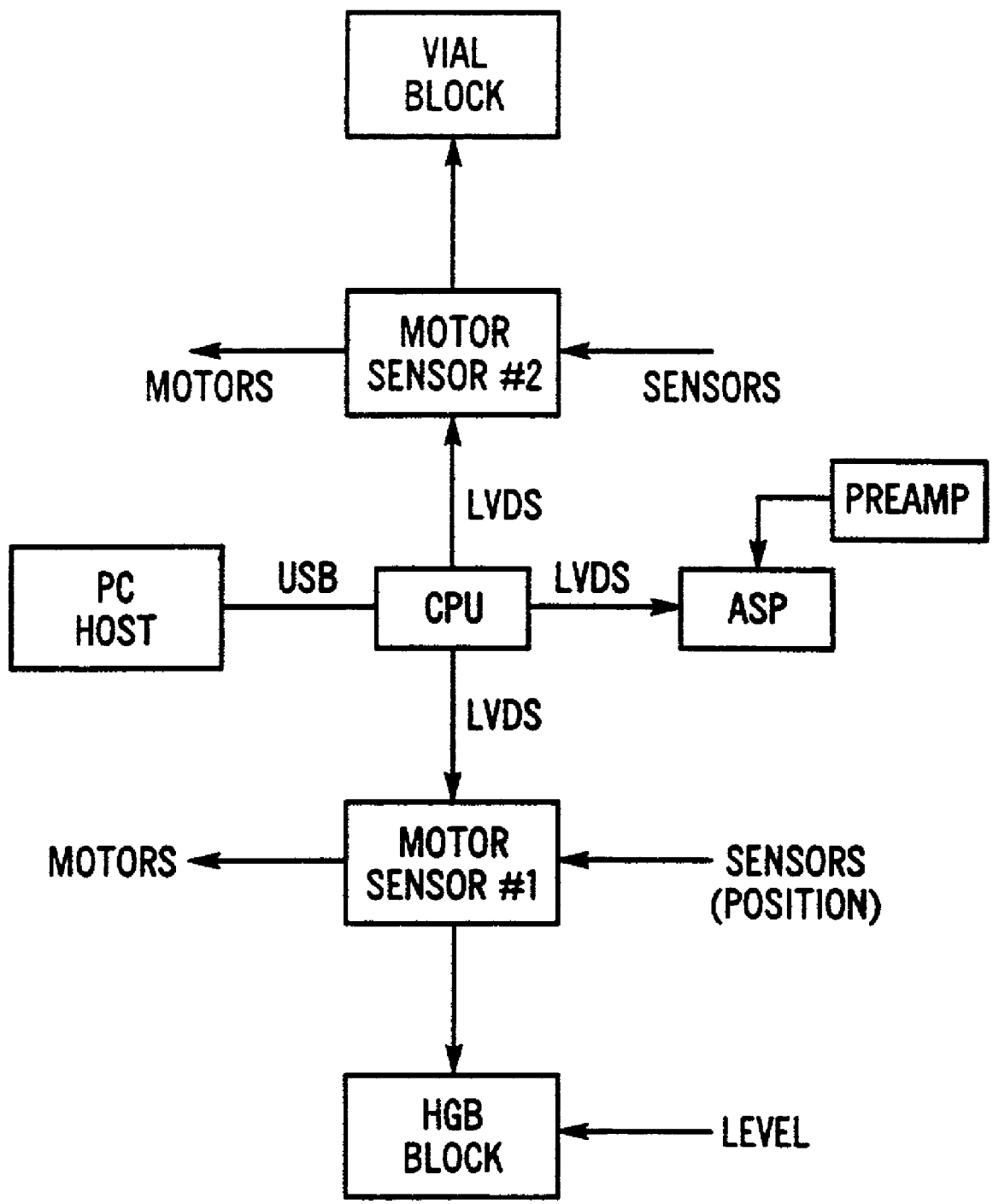
FIG. 25 is a block diagram of the system electronics of an embodiment of the device of the present invention.

The concentration of the reference particles in the sample tube and their optical characteristics are determined by a reference method. Characteristics of the particles, such as number of particles per microliter for each particle type, mean signal for an optical measurement for each particle type, and coefficient of variation for an optical measurement for each particle type, are obtained. From this information, an encrypted bar code label is generated that references any one of or any combination of at least the following parameters:

1. Type of test
2. Lot number
3. Expiration date
4. Serial number
5. Particle concentration (expressed in terms of number of particles/µl)
6. Particle EXT mean
7. Particle FSL mean 8. Particle FSH mean
9. Particle RAS mean
10. Particle TOF mean
11. Particle EXT CV
12. Particle FSL CV
13. Particle FSH CV
14. Particle RAS CV
15. Particle TOF CV
16. Optical density of sample at 488 nm
17. Optical density of sample at 540 nm
18. Optical density of sample at 580 nm
19. Optical density of sample at 635 nm The bar code label is preferably encrypted to match the consumable tube to the instrument. In this fashion, a high level of consumable tube quality can be assured, which is important for the sample analysis and dilution check procedures employed by the system. For each particle type used on the system a table of reference values is generated and stored on the instrument or, more preferably, on a PC host that is linked to the instrument, as shown in FIG. 25. The table of reference values may contain, as parameters, one or more of the following:

1. Particle Number (i.e. numerical code for type and size of particle)
2. EXT Mean
3. FSL Mean
4. FSH Mean
5. RAS Mean
6. TOF Mean
7. EXT CV
8. FSL CV
9. FSH CV
10. RAS CV
11. TOF CV Additionally, for each dye that is used on the system, there is an associated characteristic light absorption spectrum that is also stored in a table on the instrument or PC host that is linked to the system. For each lot, the dye fluid will be tested for absorption at one or more wavelengths characteristic of these spectra, i.e., a wavelength at which absorption of the dye is at a maximal or minimal point, or which is uniquely identified with the dye. FIG. 18 is an example of spectrophotometer wavelength scan data for the reticulocyte dye methylene blue. As an example, a reagent containing a blue dye, such as new methylene blue, may be tested for absorbance at 488 nm, at 540 nm, at 580 nm, and at 635 nm. Measurements at 635 nm are useful to detect blue dyes, which absorb light at this wavelength. FIG. 18 shows an absorption peak near 635 nm from the spectrophotometer wavelength scan of new methylene blue dye. FIG. 21 shows a lysed blood sample containing new methylene blue as a reticulocyte dye, and FIG. 22 shows a diluted unlysed whole blood sample containing new methylene blue. Hemoglobin absorbs green light strongly, so measurements at 540 nm are useful to measure hemoglobin concentration. This is shown in FIG. 19A by a spectrophotometer wavelength scan of cyanohemoglobin. Measurements at 580 nm are useful to detect the products of some clinical chemistry assays, which absorb yellow light, and are also helpful to measure peaks of deoxyhemoglobin. This is depicted in FIG. 19B, which shows the peaks for hemoglobin around 500 nm in a wavelength scan. Oxy-hemoglobin (around 540 nm), and deoxy hemoglobin (around 580 nm) peaks are evident in FIG. 19B. The sum of the areas of these peaks is indicative of the total hemoglobin concentration. FIG. 20 shows a spectrophotometer scan of a diluted whole blood solution, where the absorbances at 540 nm and 580 nm reflect the presence of oxyhemoglobin and deoxyhemoglobin, respectively. FIG. 21 is a similar scan of a lysed blood solution.

Finally, measurements at 488 nm are useful as a true background calibration determination. Neither any hemoglobin, deoxyhemoglobin, nor any of the commonly used reticulocyte dyes absorb at this wavelength, and thus these compounds minimally interfere with measurements at this wavelength. Other wavelengths may be used, so long as hemoglobin, deoxyhemoglobin, or any of the commonly used reticulocyte dyes doe not absorb light at this wavelength.

The use of bar codes on the consumable tubes provides the system with the information necessary to perform quality control determinations on individual samples to show dilutions were done properly, and that all of the optical measurements made were accurate. One of skill in the art would appreciate that other parameters associated with each reference particle type or cell type could also be measured and used advantageously in the system of the present invention, as desired, and the present invention is not intended to be limited in any way to the specific parameters listed above.

The information encoded on a bar code affixed to the consumable tube is compared to information loaded into the system electronic memory or a PC host linked to the system. The information encoded on the bar code label may identify, for example, the type of test and the type and concentration of particles in the tube. The type of test identified by the bar code information may determine various steps taken by the system, i.e., dilution amounts, sample amounts, and steps in the procedure. In this way, the consumable tube identifies itself to the system and directs the type of analysis to be performed.

As an example of the use of the bar code information in quality control determinations, assume that when a RBC dilution is made, the reagent volume of the consumable is diluted in half. If the initial reference particle count is 32,500 particles, the particle count during this RBC count portion should be 16,250 (32,500/2). If the reference particle count is not within a predetermined range centered around 16,250, a dilution error may have occurred, or the system may have malfunctioned in a different way. Whether an incorrect dilution occurred may be determined by incorporating and counting a second, different type of reference particle in the consumable tube, and comparing the results of the separate counts. The system can compare the value obtained for the first type of reference particles with that obtained for the second type of reference particles. If the relative deviation from the expected values are the same for each reference particle measurement, then a dilution error is suspected.

The system can also reference the expected optical values for one or more of EXT, FSL, FSH, RAS, and TOF for the reference particles. These values are independent of dilution, and thus no correction factor is needed for these measurements. The values may be stored on the PC and referenced by identification of the test type in the bar code affixed to the consumable tube. Alternatively, the values may be encoded on the bar code itself. Comparisons of the measured means and coefficient of variation of the optical values of the reference particles, as they compare to the reference values, provides information about the optical alignment of the optical detection system, laser power stability, and flow stream characteristics. As with the dilution example, if the measured light scatter data do not match expected data within a preset tolerance, some or all of the cell classification analysis will not be reported. At the same time, an error message may be displayed to the operator that will assist in the proper remedial measures. Furthermore, the system may record its performance over time, and maintain a database of the system performance over time to record trends in the system. Based on the data obtained, recommendations for service, recalibration, or troubleshooting techniques may be automatically generated.

Laser Optical System

In a flow cytometry-based hematology system, cells or particles pass individually through the sensing zone of a flow cell. This requires diluting the sample to the point where cells in the sample are sufficiently separated to pass singly through the flow cell. In conventional impedance cell counters, whole blood is usually diluted on the order of 1:10,000, because the large volume of the sensing zone of the flow cell aperture (i.e., 60 microns wide by 100 microns long) increases the possibility of coincidence events (i.e., two or more cells in the cell sensing zone at the same time). A flow cytometry-based hematology system, however, can run at higher concentrations (i.e., lower dilutions) of whole blood samples because the sensing zone on such instruments is usually much smaller, around 10 microns wide (core stream width) by 20 microns long (laser beam height). Consequently, whole blood dilutions on the order of 1:500 to 1:1,000 may be used.

For the consumable tube described above, the ideal whole blood dilution is 1:100 for analysis of RBCs. The whole blood sample may be diluted in a range between 1:20 to 1:20,000. At dilutions below 1:20, evaluation of the samples may be hindered due to coincidence, where the cells pass through the flow cell sensing zone as cell clusters rather than individually. This can lead to miscounting and mischaracterization of the cells. At dilutions greater than 1:20,000, the cells may be diluted to the point where too few events occur per unit time for suitable assessment of the sample.

For a consumable tube which dilutes sample at 1:100, less than 20% of the volume of the total consumable tube is used in this initial dilution. This leaves about 80% of the tube volume to perform a second dilution for a WBC count and a final rinse out of the system. However, this means that the sample may only be diluted about another 5- to 10-fold dilution before the consumable tube is filled, which means that the cells would be too concentrated for a conventional flow cytometry optic system. Conventionally, flow cytometry-based hematology systems either employ separate chambers for the dilutions, or rinse out the chamber after the first dilution before the second dilution is made.

The present invention, however, employs a unique approach to overcome this obstacle to use of a single tube for multiple dilutions. In this approach, the sensing zone is compressed to permit higher concentrations of cells to be counted. This may be accomplished in at least two ways. The first is to control the mass flow rate to very low but consistent rates (on the order of 0.05 microliters per second), to keep the core stream on the order of about 5 to about 7 microns wide. The second is to limit the laser beam height to around 3 microns. Either or both of these procedures may be used; however, it is preferable to use both, to minimize the degree of sample dilution.

The mass flow rate preferably is controlled by syringes to promote hydrodynamic focusing. No vacuum or pressure pumps are needed, as is the case in conventional instruments. The sheath solution is introduced to the flow cell at a much higher flow rate than the sample solution. In this manner, the sheath-confines the sample solution to a core stream. The sheath stream acts to extrude the sample stream, by accelerating it, while preserving mass flow rate. This produces a very thin (focused) stream where cells in suspension can form a single line.

The laser beam height is limited through the use of a diode laser line-emitting system, as described in copending U.S. patent application Ser. No. 09/488,211, filed on Jan. 19, 2000. In a preferred embodiment, the system comprises a diode laser which produces a light output that is oriented in first and second mutually perpendicular axes that are both perpendicular to the direction of light propagation. The system also comprises an optical system that is arranged to focus the output of a laser in a first axis and a second axis perpendicular to the first axis, at two distinct focal points that are spaced a certain distance apart in the direction of the laser light propagation. At a plane intersecting each of the focal points, the light is focused to a point in one axis and a length in the other axis. Since the light output is oriented in two mutually perpendicular axes, at each focal point, the line length is perpendicular to the direction of the line width at the other focal point. The first focal point is the plane in which the laser light intersects the cores stream of cells or particles. This plane is perpendicular to the plane of travel of the cells, and light scatters due to passage of the cells orthogonally through the thin center (focal plane) of the beam. The features of the light beam at this second focal point are described in detail below.

The laser light source is preferably a semiconductor laser (diode laser) having at least 10 mW of power at a wavelength of 650 nm or less, and which is employed in a multimode configuration. The laser beam is focused onto a flow cell, creating a spot that has a height of less than 10 μm and a width of less than 200 μm. This thin beam configuration reduces coincidence and permits high-resolution, time-of-flight determinations of cell diameter.

As a result of having a beam with a minimal height (i.e., a minimal dimension in the direction of particle flow through the flow cell), large numbers of cells, at high concentrations, can be analyzed without interference from coincidence events, since the sensing zone is minimized. This minimizes required sample volumes and reagent volumes. Furthermore, this arrangement produces a high light power distribution incident on the cells at the first focal point, so that right angle light scatter (RAS) can be measured using a much less expensive detector than that which is employed on conventional systems, which is required to measure the lower right angle scattered light levels in such systems. In particular, a photodiode can replace the use of a photomultiplier tube. The power distribution in the direction of flow allows for flow stream wander in that axis without appreciable signal drift, and further minimizes light scatter disruption caused by the edges of the flow cell by maintaining the light power distribution parallel to the flow cell channel.

Optical Detector System

Conventional flow cytometers and flow cytometry-based hematology systems collect light that is scattered from cells at a variety of angles. These systems conventionally utilize a collection lens or lens set which images the core stream, collects all the scattered light from a cellular component of a sample, and then passes it through an aperture that determines the angle of collection. This filtered light is then focused down to a photodetector, which collects the entire cone of scattered light at the desired angles. If more than one forward angle of light collection is desired, beam splitters and mirrors are used to separate distinct cones of light. For right angle scatter collection, conventionally a lens is used to image the flow stream, in order to keep background light levels low.

In the lensless design approach used in the present invention, detectors are fixed in space to collect the light signals produced by the cell passing through the laser beam, without the need for optical elements. These light signals include extinction (EXT) (0°–~0.5°); low angle forward scattered light (FSL) (~1°–~3°); high angle forward scattered light (FSH) (~4°–~9°); and right angle scattered light (RAS) (~50°–~130°). In addition, time-of-flight (TOF) measurements may also be made. No lenses or other optical elements are required in the light detector. EXT measurements are useful in quantifying the amount of incident light lost to absorption and scatter. FSL and TOF measurements may be used to measure particle sizes. FSH measurements provide information about index of refraction and internal complexity of particles. RAS measurements permit discrimination among different types of WBCs and other cells, based on the granular content of the cell. Additionally, other types of detectors (e.g., fluorescent light detectors) may also be used as desired.

The detectors are preferably placed at a second focal point of the laser beam. Here, the light that has passed through a first focal point expands in one axis, forming a long line of light having a certain height. Within this long line of light, a light detector is placed at the point where the light level in the second axis is greatest, i.e., has focused. This light detector includes an extinction (EXT) detector, which measures all of the axial light that is when the cell crosses the laser beam lost as the sum of absorbed light and scattered light. This detector is also referred to herein as an axial light loss detector. This measurement from the EXT detector hold a great deal of information, but this information can only be extracted when there is a high signal-to-noise (S/N) ratio.

Since the laser beam converges to a second focal point at the detector plane, deviation from the beam of low angle scattered light (FSL) is minimized. As a consequence, FSL can be detected and measured at small linear distances from the axis of the converging beam without the need for lenses, as are required in conventional systems. In a preferred embodiment, FSL is measured by placing an FSL photodetector as close to the EXT photodetector as is physically possible. This can be done with discrete photodiodes, or with a photodiode array that is appropriately sized for the two independent measurements (EXT & FSL).

Information concerning index of refraction and internal complexity of particles is obtained by using higher angles of forward light scatter (FSH). This light scatter measurement is generally made in the region of about 4°–9°, measured from the axis of the laser beam line of travel. This measurement may also be made without the use of lenses by either positioning a discrete photodiode to collect light scatter in the region defined by the selected angles, or by using a photodiode array having photoactive components that correspond to each desired region of measurement. In a preferred embodiment, a photodiode array that is effective to measure EXT, FSL, and FSH, all in the same array, is used. In a different embodiment, separate photodetectors may be used for each light scatter measurement. However, the photodetectors should be electrically distinct from each other, to avoid measurement errors due to electrical short circuits. It will be appreciated by one of skill in the art that many other combinations of photodetectors and photodetector arrays can be produced as desired.

Figure 4:
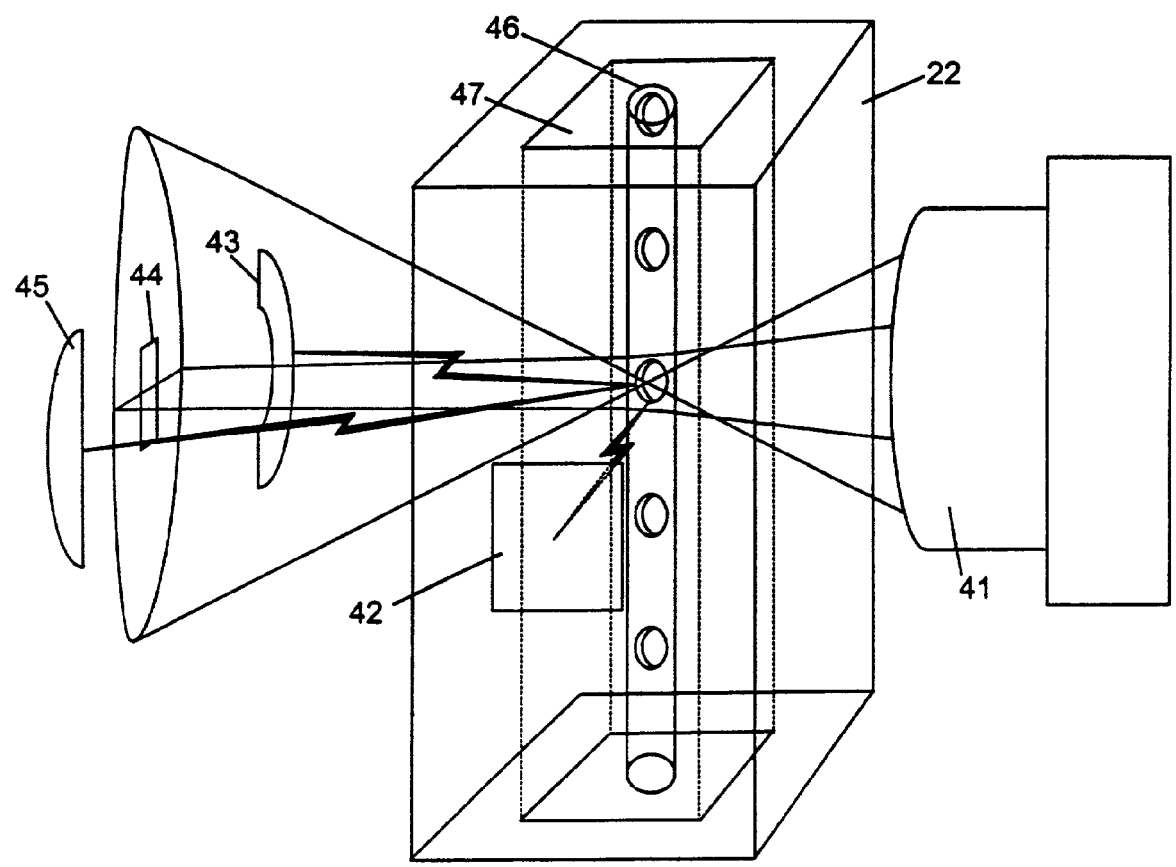
FIG. 4 is an illustration of an optic system of a preferred embodiment of the present invention, showing a light source, a flow cell, a photodetector array, and a right-angle scatter detector.

A photoarray is preferably formed on a single chip, with the detectors spaced and oriented to collect the scattered light at the appropriate angles. In a preferred embodiment, the EXT, FSL and FSH detectors are manufactured or placed in a line that is substantially orthogonal, or perpendicular, to both the direction of cell flow through the flow cell, and to the line of travel of the incident light (FIG. 4). It is also possible that the detectors could be arranged in any line that is not orthogonal to the direction of cell flow through the flow cell, but which remains orthogonal to the direction of the incident light. By "substantially orthogonal", it is meant that deviations from a perfectly perpendicular relation are permissible to the extent that they do not interfere with measurement of EXT, FSL, or FSH. This configuration allows for three or more independent measurements to be made, without the requirement of any collection or imaging lenses. Other geometries of the photodetector array are possible, such as, for example, a configuration wherein the FSL and FSH detectors are symmetrical about the EXT detector. Where multiple detectors are used to collect light of the same scattered light type, the detectors may be electrically connected, or if separate, the signals may be summed to measure the true captured scattered light signal.

While the photodetector array has been described for the collection of EXT, FSL and FSH, such an array could be extended to angles of collection as high as ~45°. At angles around 45°, the corners of a square flow cell begin to interfere with the direction of transmission of scattered light. At angles above 45°, the scattered light may overlap between FSH and RAS, and produce inaccurate measurements for one or both of the measurements.

Figure 5:
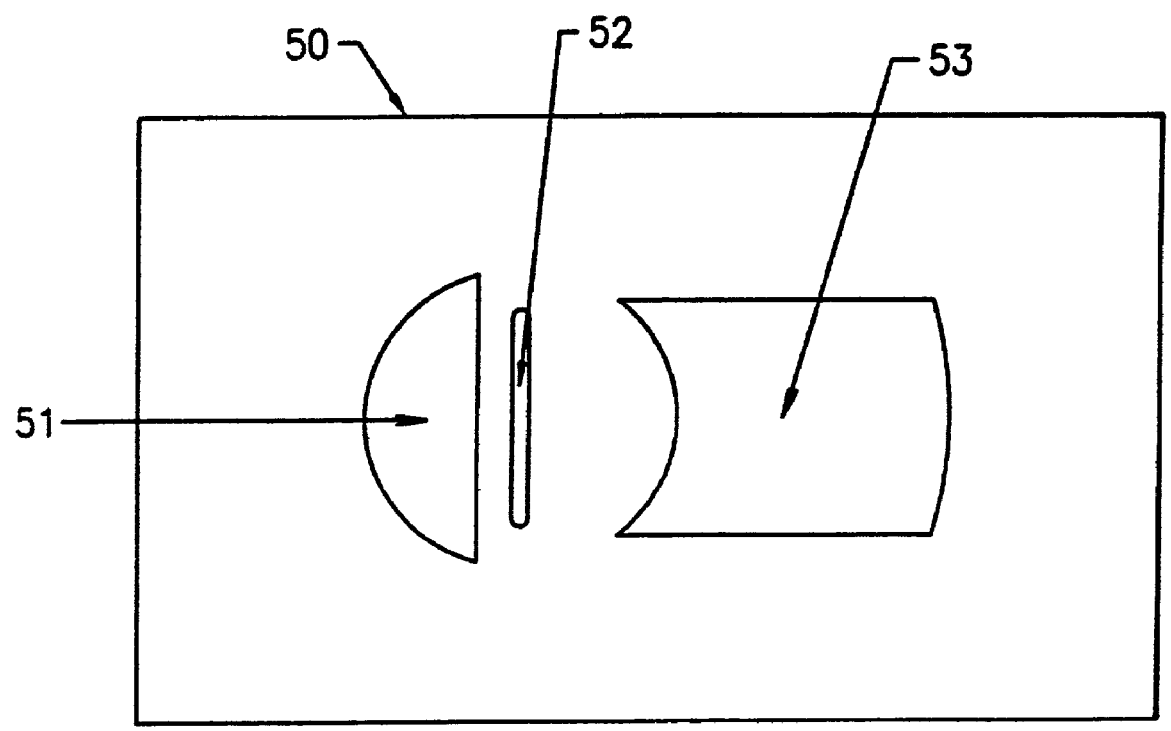
FIG. 5 is a schematic illustration of a Mie mask used in a photodetector of a preferred embodiment of the present invention.

To ensure alignment of all diode to the proper angles, and to collect only pure angles of interest, a Mie mask, which acts as a light filter, may be placed over the discrete diodes or the photodiode array. The Mie mask preferably has openings with curved shapes, to preserve the true angles of light scatter from the cells (FIG. 5). A precisely made Mie mask of the proper geometry, which may be affixed onto the photodiodes, eliminates the requirement for optical alignment of each member of the set of photodiodes, so that only the EXT detector diode must be aligned. As a consequence, construction and calibration of the instrument are simplified. The masked set of photodiodes is preferably positioned such that the EXT detector is exposed to the maximum level of incident light, i.e., at the second focal point.

The position of the right angle scatter photodiode (RAS) is essential to preserve a high numerical aperture, which can only be achieved without the use of a lens. Therefore, the photodiode is affixed near the flow cell, parallel to the plane of the laser. All or a substantial portion of the light that is scattered orthogonally by the cell or particle toward one side of the flow cell intersects the RAS photodiode. This gives orthogonal acceptance angles of ~50°–130°, or a numerical aperture of (NA) of 0.9.

It is possible that the high numerical aperture RAS photodiode may take up an entire side face of the flow cell, so no other measurements could be made on this side of the flow cell. However, the face opposite the RAS detector is still available, and can be used to obtain other measurements. For example, this side of the flow cell may be used to generate standard fluorescent flow cytometer data, by employing detectors capable of detecting emitted fluorescent light. This side may also contain one or more of the following: a collection lens (low numerical aperture) that will image the flow stream in the center of the flow cell; beam splitters and interference filters, to separate several axes of fluorescent information; imaging lenses to focus the light to a detector; and photomultiplier tubes to detect low levels of florescent emissions. Where the RAS photodetector does not occupy the entire side face of a flow cell, one or more of these additional detectors may also be placed on this same side face.

The use of a lensless light detection system eliminates the need for associated optical elements, such as lenses, beam splitters, apertures, and mirrors. The resulting light detection system is significantly smaller, lighter, less expensive, and more reliable than conventional light detection systems which rely on such optical elements to direct light beams within the instrument.

A disadvantage of using a lensless light collection system is that stray light may easily get into the detectors and create a high background signal, termed dark current noise. Sources of such stray light may include, for example, incident laser light, reflected scattered light, and the like. Lenses are conventionally used to direct the light that images the core stream, so that only light that emanates from the core stream gets to a detector. Lenses are also use to focus light collected from full cone angles down to a point where a small photodetector is placed. The use of a relatively small photodetector minimizes dark current noise, which is proportional to the area of the photodiode. However, since a constant level of light of background light is maintained on all detectors in a lensless system, a dark current noise baseline cannot be achieved. The constant background of light on the photodiodes generates a constant photo-current in the signal processing electronics. This constant photocurrent is electronically analogous to direct current, or DC, thus the lensless system generates a DC light level on each photodiode. It is desirable to minimize or eliminate the influence of the DC light signal, so that it does not interfere with the signals generated by cells or particles.

In a preferred embodiment, DC light levels may be reduced or eliminated by use of a servo feedback circuit. A local servo loop for each of the preamp circuits associated with the optical channels (EXT, FSL, FSH, RAS) is used to keep the outputs at a baseline value when no signal is present. In the absence of a signal, photodiode dark currents, input bias currents, or offset voltages may cause offsets or drift in the outputs of the preamp circuits. At least two preamp feedback methods may be used. The first method consists of a P-Channel FET with its gate connected to the output of the second stage. Due to the larger photo-current of the EXT detector, a FET feedback-voltage-to-current converter is used to maintain high impedance at the summing junction of the first stage op-amp. The feedback resistor produces a current proportional to the voltage at the output of the second stage. The second method of feedback uses an op-amp configured as an integrator to return a portion of the signal back to the first stage op-amp to reduce the offset levels through the first and second stage op-amps. The local servo loops reduce low frequency signals. Equation (1) may be used to determine the corner frequency at which the servo loop will provide (−3 dB) attenuation.

$$f_{-3dB} = R_{diode} * G2/(2\pi R_t R_f C_f)$$ Equation (1)

where $R_{diode}$=Feedback resistor across first stage op-amp
$G2$=Gain of second stage
$R_t$=Current to Voltage conversion resistor
$R_f$=Servo input resistor
$C_f$=Servo integrating capacitor By employing these or similar methods known to those of skill in the art, the desired signal portions (alternating current or AC component) can be measured accurately and reproducibly, regardless of temperature changes, laser power changes, or other environmental or electronic changes that can affect the DC light level.

Reagents

The reagents useful in the present invention are described herein in reference to counting and classification of RBCs, reticulocytes, and WBCs. It is intended that this description be illustrative and not limiting to the scope of the reagent useful in the present invention in any way. In determining the cellular composition of a blood sample, a preferred embodiment of the present invention uses at least two primary method reagents and a third system reagent. These three reagents work together to first count and classify platelets and red cells, and then, after further reagent manipulation, to count and classify white blood cells. The counting and classification take place in two discrete phases, and in each of the two discrete phases the blood-reagent mixtures are passed through a single flow cytometer and cells in the samples are identified and counted.

One method reagent, designated the RBC/Retic method reagent, is placed in a standard, capped, test tube, referred to herein as the "consumable tube". When other tests are used, the appropriate reagents are placed in the consumable tube. A separate consumable tube is used for each test run. For a CBC test, the consumable tube containing the RBC/Retic method reagent may comprise the following:

A reticulocyte dye. The dye may be any that is conventionally used to selectively stain reticulocytes, such as, for example, new methylene blue, coriphosphine O, brilliant cresyl blue, acridine orange, pyronin Y, or thiazole orange. In the present invention, the preferred dye is new methylene blue. This component serves to stain the residual RNA in reticulocytes a blue color. The dye is preferably used in a concentration range of between about 0.1 to about 0.5 grams per liter, most preferably about 0.3 grams per liter.

A red cell sphering agent. The red cell sphering agent may be any effective to cause RBCs to adopt a spherical shape without causing lysis of the cell. In the present invention, the preferred sphering agent is Plurafac-A-39, in a preferred concentration range from about 0.1 to about 0.6 grams per liter. This component acts to modify the normal biconcave shape of red blood cells, by interacting with the cell membrane and the internal hemoglobin, to form spherical cells. The most preferred concentration is about 0.3 grams per liter.

Internal reference particles at a known concentration. The concentration is preferably about $10^4$ particles per µl, but the reference particles may be used in a range of about $10^3$ to about $10^5$ per µl. The reference particles include light scattering reference particles, but may be used in combination with reference particles labeled with fluorescent compounds.

Buffers and preservatives. In a preferred embodiment, the buffers and preservatives may comprise sodium bicarbonate (preferably about 8.0 grams per liter, but can range from about 6.0 to about 10.0 grams per liter); sodium chloride (preferably at about 3.1 grams per liter); Tricine (preferably at about 1.8 grams per liter, but ranging from about 1.0 to about 5.0 grams per liter); disodium EDTA (preferably at about 1.0 grams per liter, but ranging from about 0.5 to about 3.0 grams per liter); ethyl paraben (about 0.3 grams per liter), and methyl paraben (about 0.2 grams per liter). The pH of this solution should be in a slightly basic range between about 7.2 to about 8.9, with an osmolarity of between about 275 and about 294 milliosmoles, and a conductivity of between about 11.0 and about 13.0.

The second method reagent is designated the "lyse". The lyse acts to destroy red blood cells while leaving the white blood cells intact. In this fashion, the white blood cells can be analyzed, without interference from the vast numbers of red blood cells. The lyse is preferably provided in a tube separate from the consumable tube. This reagent may be packaged in a standard capped test tube, preferably in a form that allows it to be used with up to about fifty separate consumable tests.

The lyse preferably comprises:

Saponin, preferably at a concentration between about 6 and about 20 grams per liter. The most preferred concentration is about 18 grams per liter.

Buffers and preservatives, which may comprise, for example, sodium sulfate (preferably at about 12 grams per liter, but effective in a range of about 10 to about 16 grams per liter); disodium EDTA (preferably at about 1 gram per liter, but effective from about 0.5 to about 3 grams per liter); Proclin 300™ (preferably at about 0.5 ml per liter); and germabox II (preferably at about 1 ml per liter). This pH of this reagent is preferably in a range between about 4.2 and about 5.2, with an osmolarity of between about 235 and about 285 milliosmoles, and a conductivity of between about 14 and about 16.

The third reagent is designated the system reagent, or "sheath solution". The sheath solution performs several functions, such as whole blood dilution reagent, sheath reagent for flow cytometric analysis, washing reagent for the instrument's hydraulic path, and lytic aide to assist the lyse reagent in lysing red blood cells. The sheath is preferably packaged in a container that is separate from either the consumable tube or the lyse, and preferably holds enough solution to run about fifty separate consumable tests.

The sheath preferably comprises the following:

Phosphate-buffered saline solution (preferably having an osmolarity of about 25 milliosmoles, but may be used in a range from about 5 to about 50 milliosmoles).

Surfactant to aid in both cleaning of internal system components, and to keep internal wetted surfaces from having air bubbles adhere to them. The preferred surfactant is Plurafac-A-39, which may be used in a range of about 0.1 grams per liter to about 0.3 grams per liter, and preferably at a concentration of about 0.1 grams per liter. Besides Plurafac, other non-zwitterionic surfactants such as, for example, alkylphenol ethoxylates and alcohol ethoxylates, could be used.

Preservatives, to inhibit the growth of microorganisms in the solution. Preservatives useful in this solution include, for example, sodium azide, Proclin 150™, or Proclin 300™.

The consumable tube may additionally or in place of the above reagents contain other reagents directed to tests that are not associated with the standard hematological analyses outlined above. For example, the system may also be used in immunoassays, or in analyses of biological fluid samples other than whole blood. Examples of such biological fluids may include, without limitation, blood products, bone marrow, cerebrospinal fluid, synovial fluid, urine, or any other fluid containing or suspected to be containing cells. In such cases, reagents useful for the desired analyses may be included in the consumable tube. Examples of such reagents include various forms of antibodies, such as monoclonal antibodies, polyclonal antibodies, and antibody derivatives, such as F(ab), F(ab')$_2$, scFv, and Fv fragments. Other reagents could be, for example, enzymes or enzyme substrates or inhibitors, or receptor or receptor ligands, as well as receptor bodies. The bar coded labels on the consumable tube may reflect the type of test for which the tube is intended, and may also contain information relating to the contents of the consumable tube.

Other assays that do not require the optical detection system to count or classify cellular components or particles can also be analyzed in this invention. The consumable tube can be configured to run clottable assays, such as coagulation time assays. Prothrombin time (PT), activated partial thromboplastin time (aPTT) and thrombin time (TT) can be measured by using a consumable tube containing an agonist or, less preferably, placing an agonist in the consumable tube, and then adding whole blood containing an anticoagulant, such as sodium citrate or sodium EDTA. The whole blood and the agonist will form a clot in the presence of calcium. By spinning the tube, the clot collects at the center, and is detected as a decrease in light transmission through the consumable tube.

In a similar manner, platelet aggregation tests may be run on the system. In these assays, an agonist, such as ristoceitin, is either included in or added to the consumable tube. Platelet-rich plasma is added to the consumable tube, and the tube is again spun to collect the resulting aggregates in the center. The aggregates are detected as a decrease in light transmission through the consumable tube. Both the platelet aggregation test and the clottable assays require a stable temperature for performing these assays. Therefore, a heating element is preferably included in the slot in which the consumable tube is held for these tests, in order to enable accurate measurements.

In the particular case of a CBC test, the user presents to the instrument a barcode-labeled consumable tube, as well as a properly anti-coagulated whole blood sample in a sample tube. The instrument reads the necessary information from the barcode to identify the consumable tube, then automatically aliquots a small amount of whole blood from the sample tube into the consumable tube, along with a predetermined volume of sheath solution to act as a diluent. This ideally creates a total dilution of one part blood to 100 parts solution (RBC/Retic method reagent and sheath), but the dilution can range from 1:50 to 1:5,000.

A known volume of the diluted whole blood solution is then pulled into the instrument from the consumable tube through an HGB module a first light absorption measurement is made. This measurement detects principally the amount of reticulocyte dye in the solution, but also enables determination of the amount of hemoglobin in the sample (see below). Thereafter, the red cell solution is moved to a position near the entrance to an optical flow cell. The diluted whole blood solution is then passed through an optical detector system (described above), where light scatter and light absorption for individual red blood cells, platelets and reference particles may be measured, and the number of each cell type determined. Hydrodynamic focusing is used to maintain a slow mass flow rate of the diluted whole blood solution through the optical detector system. Preferably, the mass flow rate is less than about 0.25 microliters per second.

After red cell/platelet analysis is complete, a second, larger amount of whole blood is aliquoted into the consumable tube, along with an aliquot of lyse and appropriate amounts of sheath solution. This dilution can range from 1:10 to 1:100, but is preferably a 1:20 dilution. The intent is to provide a solution that can lyse the red blood cells, but keep intact the white cells of the whole blood sample for a period of at least one minute.

A known volume of this lysed blood solution then enters the instrument from the consumable tube and moves to a position near the entrance to the optical flow cell, passing through the HGB module, where a second, more accurate HGB determination is made (see below). The solution is then passed through the optical detector system, where light scatter and light absorption for individual white blood cells, reference particles, and dye may be measured. Hydrodynamic focusing is used to maintain a slow mass flow rate of the white cell solution through the optical detector system. Preferably, the mass flow rate is about one microliter a second.

High Frequency Modulation to Reduce Diode Laser Mode-Hopping

In a preferred embodiment of the present invention, high frequency modulation is employed to obtain accurate measurements when a laser diode is used. High-frequency modulation reduces or eliminates mode hopping by having the laser exist in a multi-mode state. When temperature or current changes occur in a laser running under high-frequency modulation conditions, the primary mode of the diode laser changes, but since the diode laser is running in many modes to begin with, these changes do not produce any noise spikes. Furthermore, the frequency of modulation preferably is chosen to be much higher than the frequencies of interest for cell events, so the modulation is invisible to the system.

The use of high frequency modulation eliminates the need for temperature and/or current control systems in addressing mode hopping, thus saving the costs and complexity associated with these systems. A high frequency modulation system stabilizes the laser diode within seconds, so there is no need to control for the temperature generated by the diode laser upon activation. Thus, the useful laser life is extended. Furthermore, unlike the temperature cooling systems, high frequency-modulated diode lasers are stable over a wide range of operating temperatures. With high frequency modulation, there is no need to find a quiet temperature/current area for the laser, and no need to reset the equipment as the laser ages. Thus, the labor cost incurred in finding and maintaining a quiet temperature/current area for the diode laser is avoided.

High-frequency modulation is imposed on a diode laser in the following manner. A diode laser running in continuous wavelength (CW) mode has a built-in photodiode that is used for power feedback, so that the power does not vary with temperature. This circuit changes the current input to the diode of the laser so that the light power is kept constant. In one embodiment, the CW set point of the laser driver is set so that it produces one-half of the rated power output of the laser. Next, a modulating circuit, which uses a crystal oscillator to produce an electric current with a sine wave output, is "summed" with the CW current. As a result, the laser power output takes on a sine wave shape, with a power maximum near the maximum rated power level of the laser at the peak of the sine wave and almost zero power at the minimum of the sine wave.

Figure 23A:
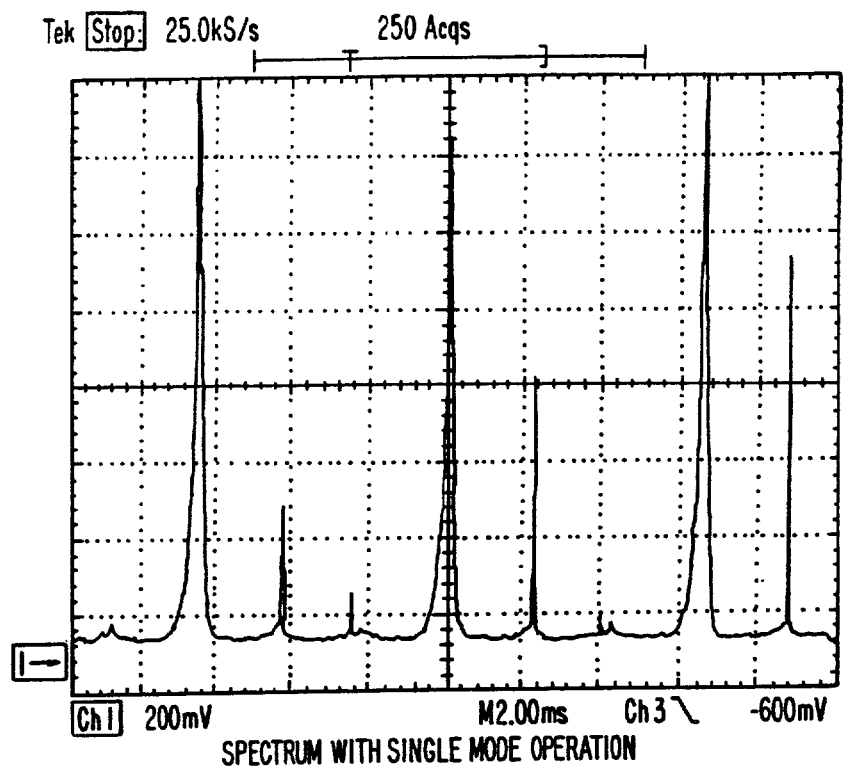
FIG. 23A displays the spectrum analyzer output of a diode laser operating in continuous wavelength mode, without high-frequency modulation.

FIG. 23A shows the noise level of a diode laser operating in continuous wavelength (CW) mode, in the absence of high-frequency modulation. The peaks in FIG. 23A illustrate the high levels of noise at many different frequencies found in such diode lasers. While the baseline for this diode laser is excellent, the high frequency noise peaks cause significant problems when trying to implement an extinction measurement and a lensless scatter collection system. The net effect is false event counting and improper quantification of pulse height or area.

Figure 23B:
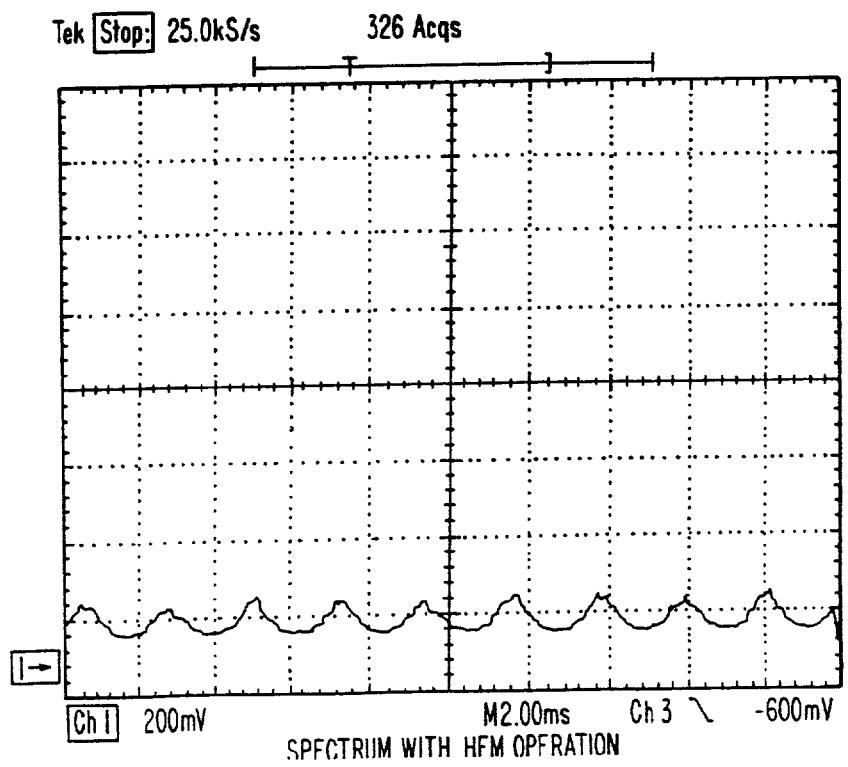
FIG. 23B displays the spectrum analyzer output of the same diode laser as in FIG. 23A, operating with high frequency modulation.

FIG. 23B shows the noise level of the same diode laser operating in CW mode, where high-frequency modulation has been imposed. The spectrum of the high frequency-modulated laser in FIG. 23B does not have as low a baseline level as in seen in the diode laser of FIG. 23A, but also has no high spikes. This helps enables accurate EXT measurements, and the implementation of a lensless collection system for the other channels.

Figure 24:
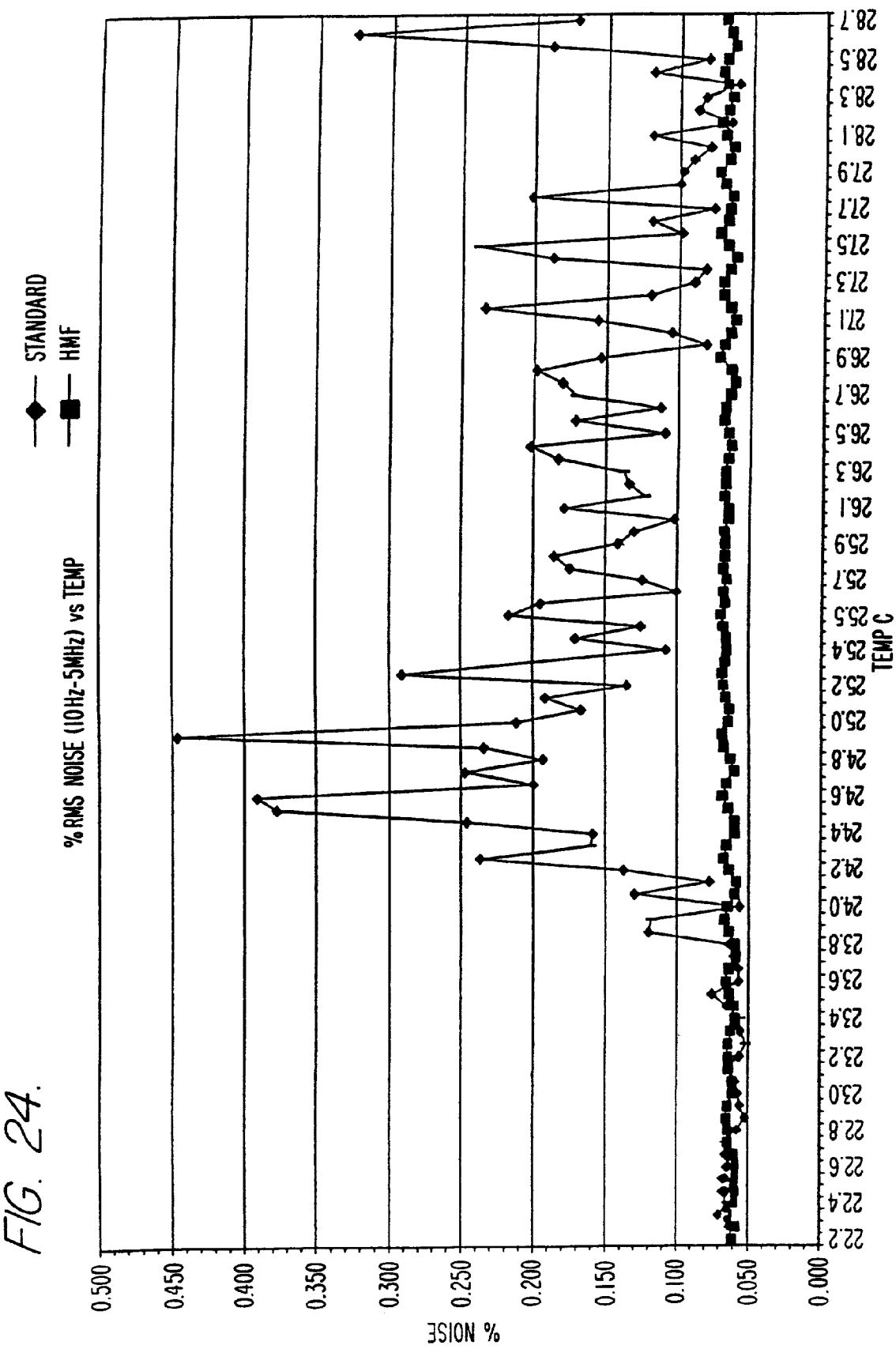
FIG. 24 is a plot of noise (root mean square) versus temperature for a diode laser operating in continuous wavelength mode in the absence (♦) and presence (■) of high frequency modulation.

FIG. 24 shows that a single-mode laser is driven at a constant power can achieve noise levels at or below that of high frequency-modulated lasers in some temperature ranges (i.e., between about 22° C. and about 23.7° C.). Thus, either high frequency modulation or a temperature-controlled system can produce a laser that is capable of enabling accurate EXT quantification, and the implementation of a lensless collection system for the other channels. However, because the cost of controlling temperature in a diode laser is much greater than the cost of imposing high-frequency modulation on a laser, it is preferable to employ high frequency modulation to minimize noise.

HGB Module

In a preferred embodiment of the present invention, hemoglobin (HGB) content is measured in a unique manner. The method involves two separate measurements, which not only combine to give an accurate HGB value, but also verify the accuracy of the dilutions that the system has made. The first HGB measurement occurs after the whole blood sample is diluted with a reticulocyte staining solution. Preferably, one part of the whole blood sample is diluted with 100 parts of the reticulocyte staining solution. The resulting diluted sample is referred to as the "red cell solution", and has a specific absorption spectra. The red cell solution is next aspirated into a manifold block. This block contains at least three light sources, configured to illuminate a cylindrical bore, where the red cell solution is held. Three light sources are used to provide a measurement of HGB concentration. The light sources are preferably LEDs, but may be any appropriate light source. Photodetectors are placed in line with the light source and the cylindrical bore containing the red cell solution. Optionally, interference filters may be employed as desired. Preferably, the three wavelengths used in measuring HGB concentration are 488 nm, 540 nm, and 580 nm. An additional light source, emitting light at a wavelength different from the other three, may be included to enable measurement of the amount of a reticulocyte dye in the red cell solution and/or the white cell solution, and thereby enable detection and quantitation of reticulocytes.

The initial absorption measurements of the red cell solution do not provide as accurate a measurement of HGB concentration as conventional techniques. However, the value of this measurement lies in its use for the determination of the accuracy of the whole blood sample dilution. As the instrument continues its cycle after making the initial "unlysed" hemoglobin measurement, total RBC and mean cell volume measurements are made in the cytometer portion of the instrument. This enables the calculation of the following:

Hematocrit (HCT)=RBC*MCV/10

Mean Corpuscular Hemoglobin Concentration (MCHC) =100*(HGB/HCT)

Mean Corpuscular Hemoglobin (MCH)=HGB/RBC

As the instrument cycle continues, more whole blood is added to the original solution, as well a lytic agent. The lytic agent destroys the red blood cell membranes (lysis), releasing HGB free in solution. This yields a solution containing approximately 1 part whole blood to between 15 and 50 parts solution, which is referred to as the "white cell dilution". The white cell solution contains all of the dye from the previously measured red cell solution. The dye in the red cell solution is diluted out with an optically clear fluid by a factor between 1:1 and 1:4.

The white cell solution is aspirated into the manifold block where the multiple absorption measurements are made, and a HGB value calculated. From this second HGB value, the HCT, MCHC and MCH values can be recalculated. In addition to the HGB value, dye concentration can be measured, and compared to values obtained from the red cell solution. If, within a defined tolerance, the two independent HGB (HCT, MCHC, MCH) measurements match, and the dye ratios between the two solutions match, the instrument has, by measurement, verified all of its dilutions were performed accurately.

The white cell solution HGB calculations yield an accurate measurement of the HGB concentration. The red cell solution HGB calculations are not as accurate as the white cell solution HGB calculations, because the red blood cells in the red cell solution are intact, and the intact red cell membranes scatter light. In contrast, in the white cell solution the red blood cells are lysed, and the total HGB content is released into the solution. However, the red cell solution HGB measurements permit comparison of the differences in the dye absorbances, which allow a check of the accuracy of the dilutions. In other words, the red cell solution has a certain level of light absorption which is based on the concentration of the dye in the consumable tube. Later in the cycle, the white cell solution is measured for light absorption due to the dye. Because the hydraulic pathways for the red cell solution HGB measurement and the white cell solution HGB measurement are common, the accuracy of the dilutions may be determined without the need for separate reference solutions to control for differences between pathways. The acceptable range of ratios of the HGB measurements is known, e.g., from being printed on a barcode label on the consumable tube or from a code on the consumable tube barcode label that references a value in a table of ratios stored in a linked PC. As a second check of the accuracy of the dilutions, the ratio of the HGB measurements should also be within a predetermined range. Otherwise, a dilution error should be suspected. The only case in which the dilution error might occur but be undetected is the highly unlikely situation in which identical percent dilution errors are made on both samples.

Preferably, the bar code on the consumable tube contains reference information on the expected values of dye absorption for undiluted samples (CAL). The instrument may verify this information for each lot number in use by evaluating the absorbance of the dye solution before the addition of whole blood to the solution. After the first dilution, the red cell solution should have a dye absorption value and an HGB concentration value that fall within a first set of expected ranges. These ranges should be the product of CAL and a first dilution factor D1 (i.e., CAL×D1). After the second dilution, the white cell solution should have a dye absorption value and an HGB concentration that fall within a second set of expected ranges. These ranges should be the product of CAL, D1, and a second dilution factor D2 (i.e., CAL×D1×D2). So long as both sets of measurement are within the acceptable ranges, the results of the measurements are reported without associated error messages.

System Electronics

Figure 26:
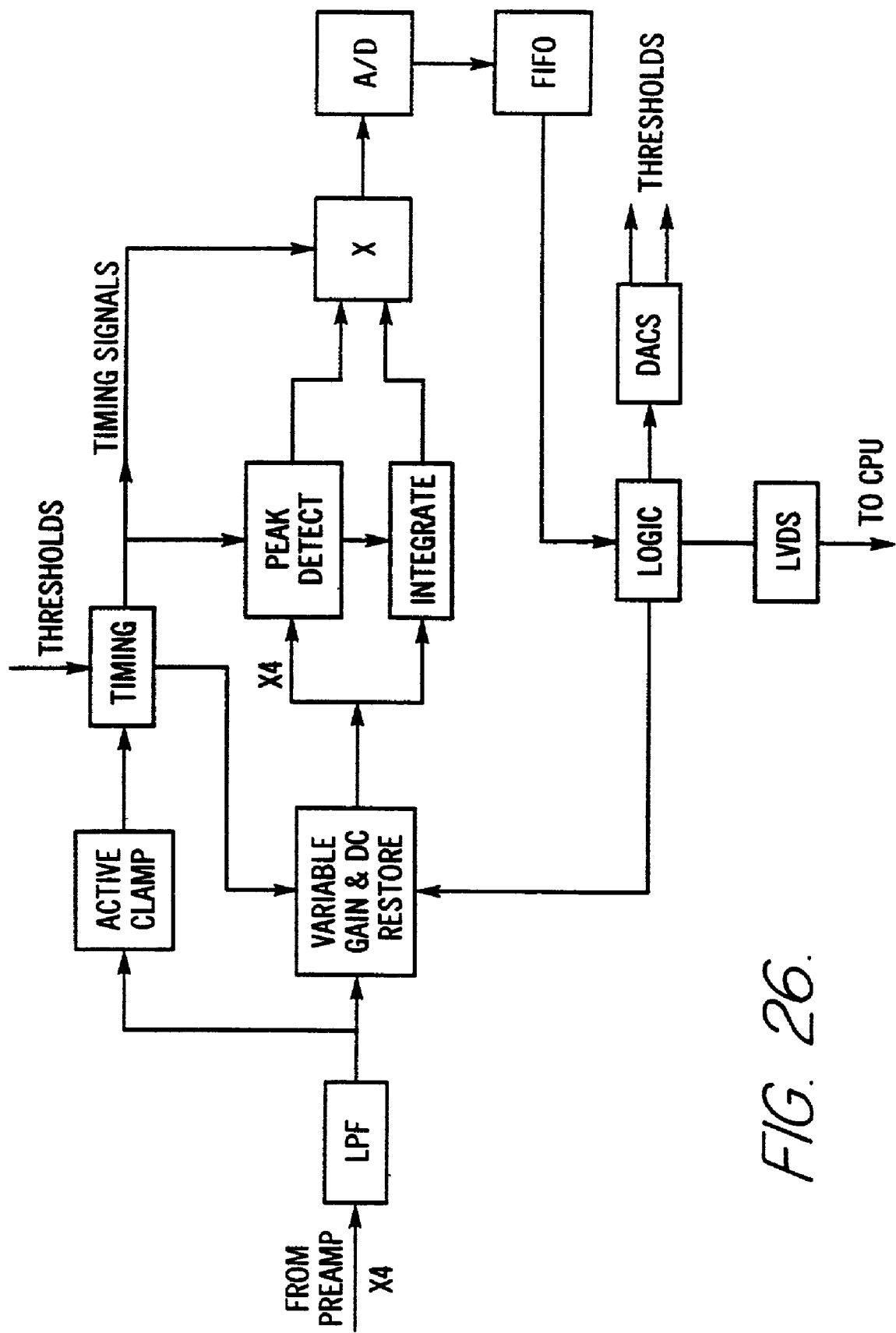
FIG. 26 is a block diagram of the signal processing electronics of an embodiment of the present invention, showing in greater detail the flow of data that occurs in the ASP module of FIG. 25.

In a preferred embodiment, the center of the system electronics is a central processing unit (CPU) that is responsible for handling communications between the different sub-systems. A personal computer (PC) preferably acts as the user interface and data processor. Alternatively, the user interface and data processor may be built into the body of the instrument. In either case, the input issues commands to and receives data from a CPU. Data may be transmitted via any appropriate and conventional means, such as, for example, across a universal serial bus (USB). The CPU in turn translates the PC commands, and issues commands to a set of two identical motor/sensor electronic boards. These motor/sensor boards receive input from the various sensors on the system, and move the appropriate motors such that particle events are passed through the laser optics. The light signals from the scattered light detectors are amplified by a pre-amplifier, which is in close proximity to the photodetectors, and then passed to a signal processor that analyzes the electrical signals from the detectors. In one embodiment, the signal processor is an analog signal processing module (ASP), as shown in FIG. 26. Processed data from the ASP is communicated to the CPU, and then to the PC host. Alternatively, as noted above, the user interface may be contained within the instrument, obviating the need for a linked PC. The rest of the system would work as described above. A person of ordinary skill in the art would recognize that variations in this scheme are possible to create the desired level and types of control over the system.

EXAMPLE

The following description describes the system of the present invention in relation to the accompanying figures, and its use in measurement of a whole blood sample for a CBC, a five-part WBC differential, and a reticulocyte count. It will be understood by those of skill in the art that certain modifications may be made in the invention as described below without departing from the scope or spirit of the attached claims. Throughout this specification, the term "inlet side" refers to the side where a fluid enters. "Outlet side" refers to a side where fluid exits. "Sample mixture" refers to a fluid sample, usually a blood sample or blood-derived sample, that is mixed with another solution.

Figure 6:
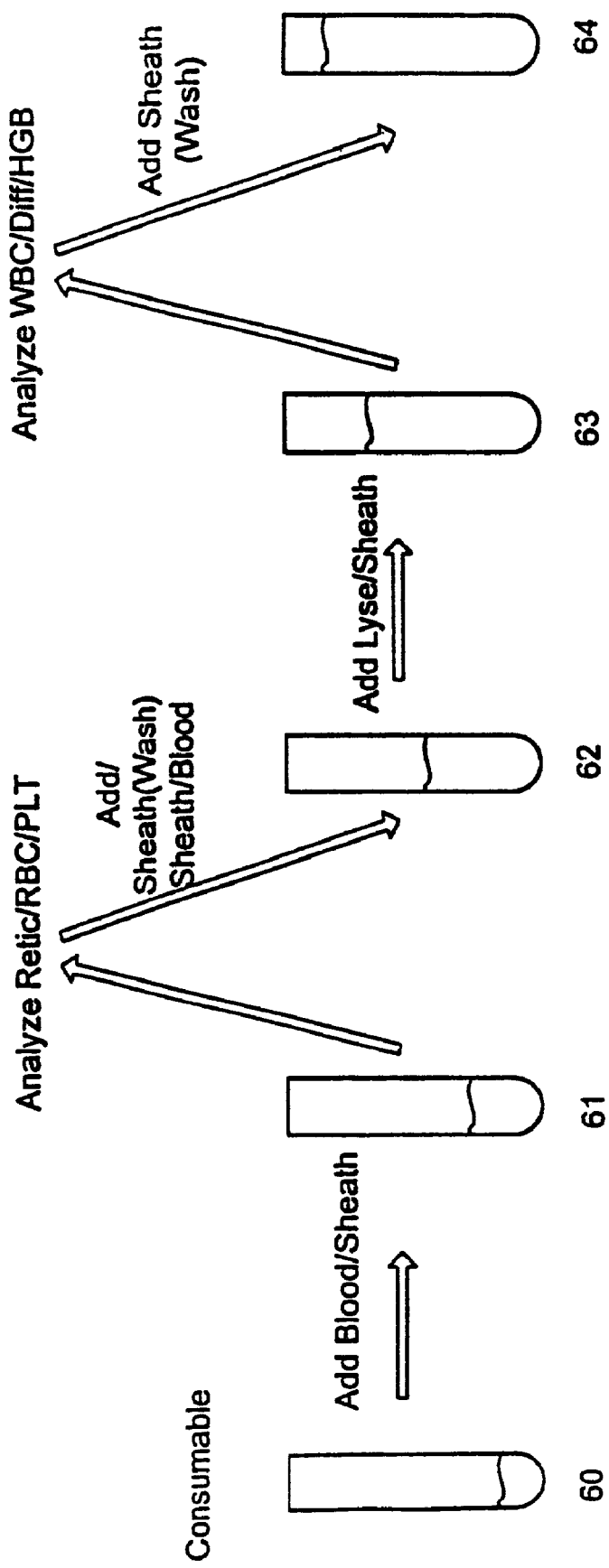
FIG. 6 is a schematic representation of the events that occur in a consumable tube during the system cycle of a preferred embodiment of the device of the present invention.
Figure 7:
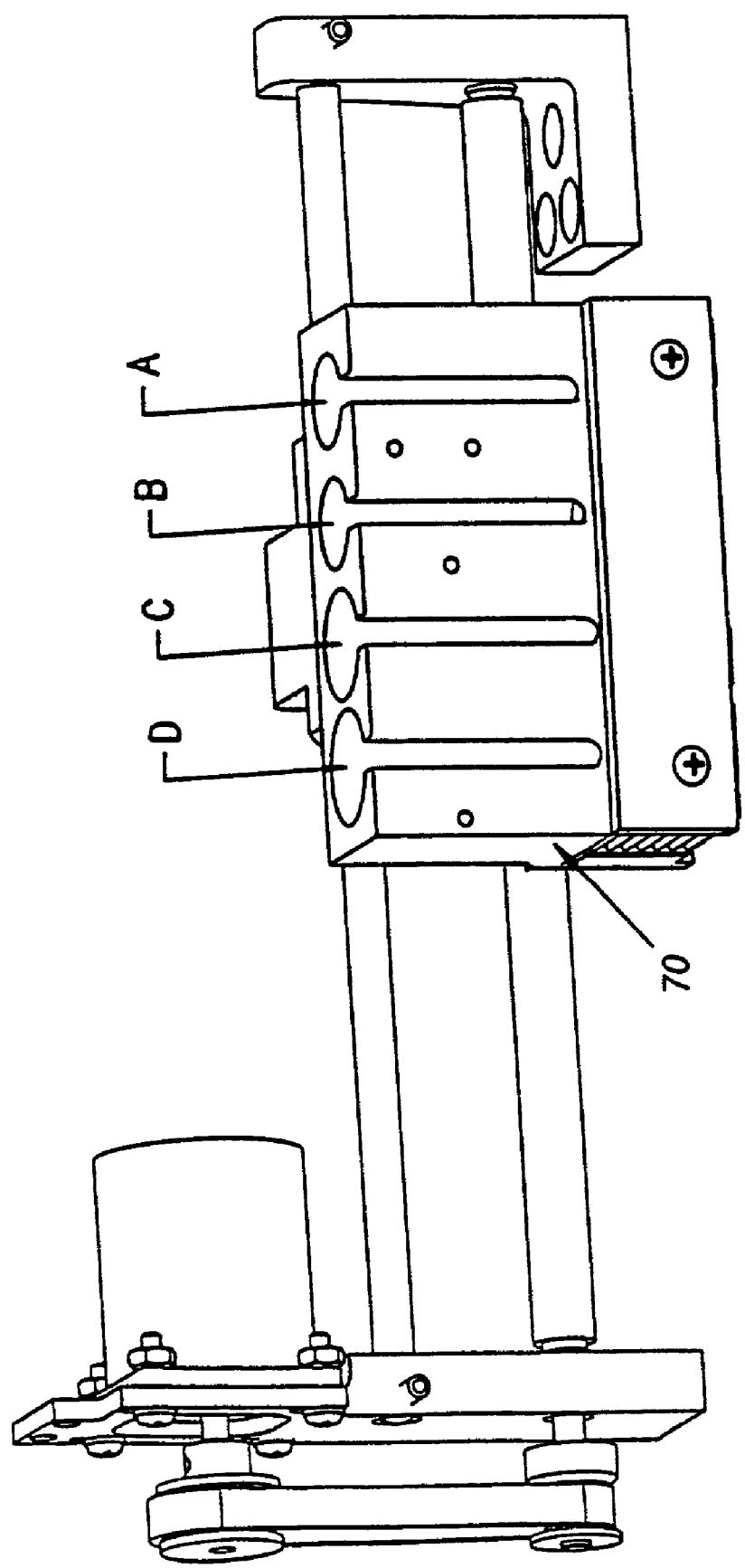
FIG. 7 is a schematic illustration of an embodiment of a tube positioning assembly used in a preferred embodiment of the present invention.

Referring now to FIGS. 1–9, the user initiates the process by opening a door of the system, to expose four open tube slots in a carriage 70 (slots A–D in FIG. 7). In one slot (i.e., slots A or B of FIG. 7), the user places a consumable tube 60, and in a second slot, a whole blood sample, which contains an anti-coagulant (i.e. EDTA, citrate, and heparin). A third slot holds a tube containing lyse reagent. The fourth slot may be kept open, or may be occupied by a second consumable tube. At least one slot intended for a consumable tube contains a heating element 74, for performing clottable assays, platelet aggregation assays, or any other assays which require heating or a constant temperature. Preferably, the lyse reagent tube contains a sufficient volume to run at least 20, and more preferably about 50, tests. The user then closes the door. The system verifies the presence and identity of the tubes. Carriage positioning assembly 76 acts to turn motor 71 which acts in concert with lead screw 72 and moves carriage 70 along guide rod 73, so that consumable tube 60 is positioned under a mixer assembly 80. Motor 82 positions mixer assembly 80 so that it is in contact with the top of consumable tube 60. Spinning in one direction, and then reversing the direction mixes the contents of consumable tube 60. During the spinning process, a bar code label affixed to consumable tube 60, which contains lot calibration information, is read by a bar code reader (not shown). After adequately mixing consumable tube 60 to homogenize the solution, carriage positioning assembly 76 moves carriage 70 to position the whole blood sample tube under mixer assembly 80, and the whole blood sample tube is mixed in a similar manner so as to ensure sample homogeneity.

Figure 8:
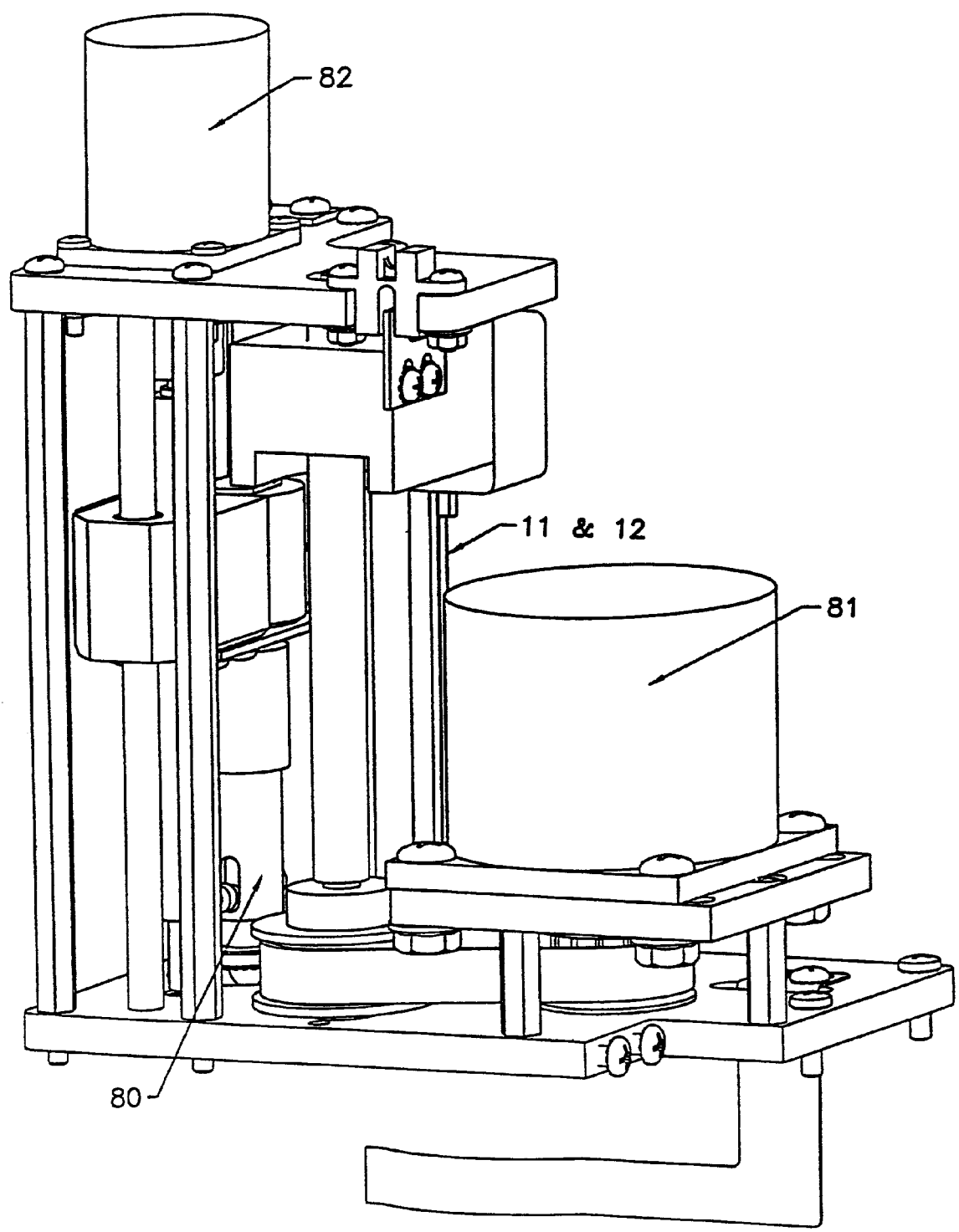
FIG. 8 is a schematic illustration of a mixing and piercing assembly of a preferred embodiment of the present invention.
Figure 9:
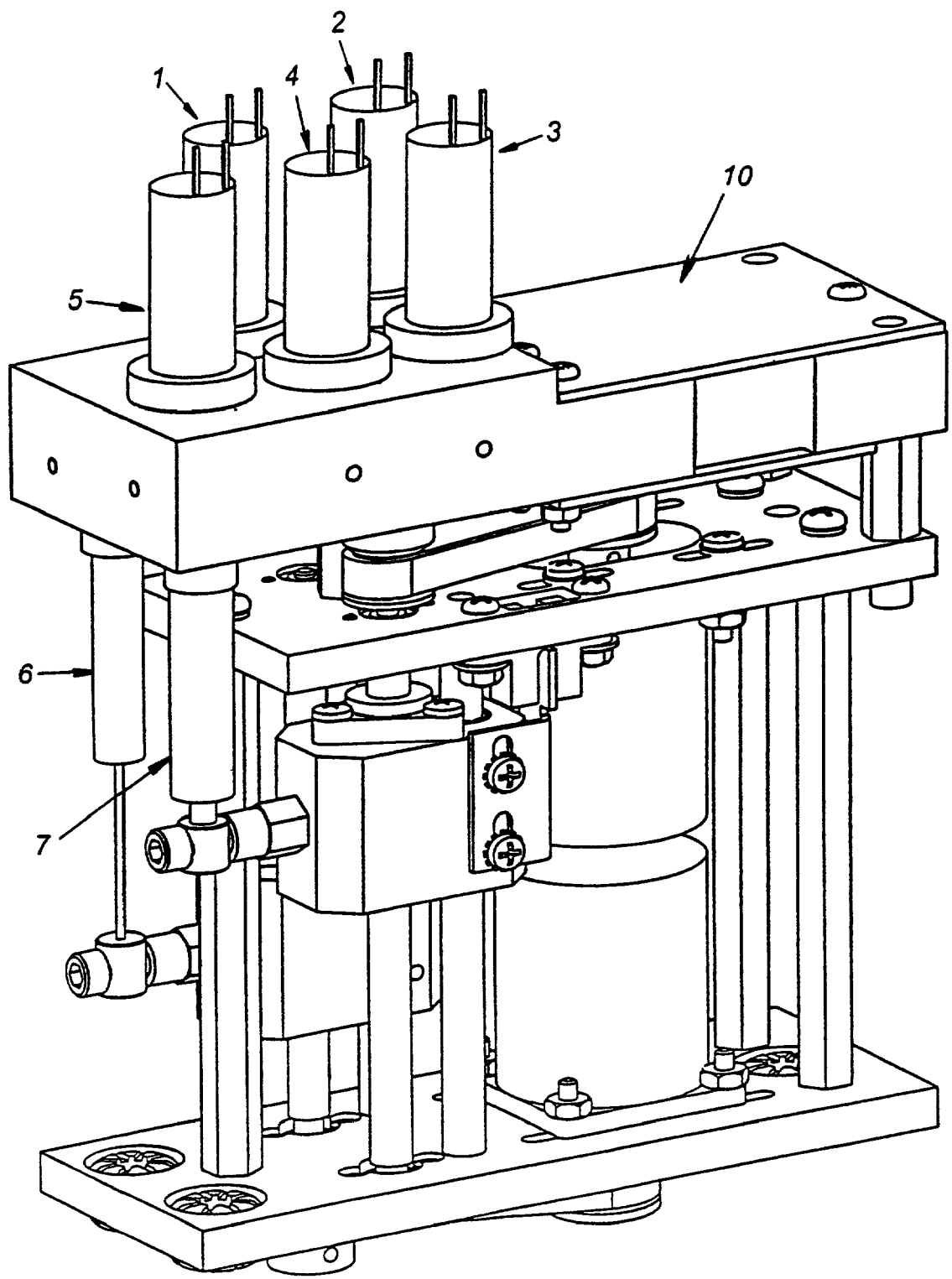
FIG. 9 is a schematic illustration of the system hydraulics of a preferred embodiment of the present invention.

Carriage positioning assembly 76 moves carriage 70 then positions the sample tube underneath a hydraulic needle 11 and a pneumatic needle 12 (FIGS. 1 and 8). Needle 11 pulls up samples and reagents at various points during the assay, and transfers the samples and reagents among the different tubes. Needle 12 is a vent needle, used to maintain atmospheric pressure in the tubes. By moving motor 81, needles 11 and 12 pierce the sample tube septum, and continue to penetrate the sample tube until both needles 11 and 12 come in contact with the surface of the blood sample. This ensures that the orifice of hydraulic needle 11 is completely immersed, but the orifice of pneumatic vent needle 12 is not.

Referring again to FIG. 1, opening valve 3 and moving syringe 6 pulls blood into the tip of needle 11. Ideally, five microliters of whole blood are aspirated for this portion. Valve 3 is then closed. Needles 11 and 12 are then retracted from the whole blood sample. Needles 11 and 12 are wiped almost completely clean as they are withdrawn through the septum. Carriage positioning assembly 76 now positions consumable tube 60 under needles 11 and 12. Motor 81 moves needles 11 and 12 to pierce the septum of consumable tube 60 and penetrate consumable tube 60 until both needles 11 and 12 come in contact with the surface of the reagent in consumable tube 60.

Valves 5 and 3 are then opened to allow syringe 7, which is filled with sheath solution, to begin to dispense sheath solution. The movement of sheath solution from syringe 7 pushes the sample blood from the tip of needle 11, along with a volume of sheath solution, into the consumable tube, which is now represented by 61 (FIG. 6). While dispensing, motor 81 moves needles 11 and 12 upward so as to prevent the orifice of needle 12 from coming into contact with the solution in consumable tube 61. This solution is now fairly homogeneous, but to ensure homogeneity, valves 3 and 5 are closed, and needles 11 and 12 are withdrawn from consumable tube 61. Consumable tube 61 then is moved to the mix position under mixer assembly 80, and mixed by spinning, as described above. During this process valves 3 and 5 open, and syringe 7 pulls back to create an air gap at the tip of needle 11.

Consumable tube 61 is next placed under needles 11 and 12 by moving carriage assembly 76. By moving motor 81, needles 11 and 12 pierce the septum of consumable tube 61, and penetrate the tube until both needles come in contact with the surface of the solution. Syringe 7 then aspirates a predetermined volume of solution into the tip of needle 11 behind the air gap. Needles 11 and 12 are then withdrawn from the solution by motor 81, but are not removed from consumable tube 61. Syringe 7 then pulls air into needle 11. This creates a slug of the diluted whole blood in needle 11, bordered by air gaps on each side. Syringe 7 then pulls this slug through HGB module 10 (FIGS. 1 and 9), where it is evaluated for light absorption at four separate wavelengths of light. Spectral data typical of such measurements are presented in FIG. 22. The volume of the sample slug can also be evaluated at this point by evaluating the change in absorption values in the detector channels as the air gaps on each side of the slug pass through the detector channels. By evaluating the time taken for the absorption values to change, and knowing the rate of sample movement through the detectors, the volume of the sample slug can be easily calculated. If the volume of the sample slug deviates by a predetermined amount from that expected, an error message can be displayed to the user, and the sample analysis halted until the problem is fixed.

Figure 2:
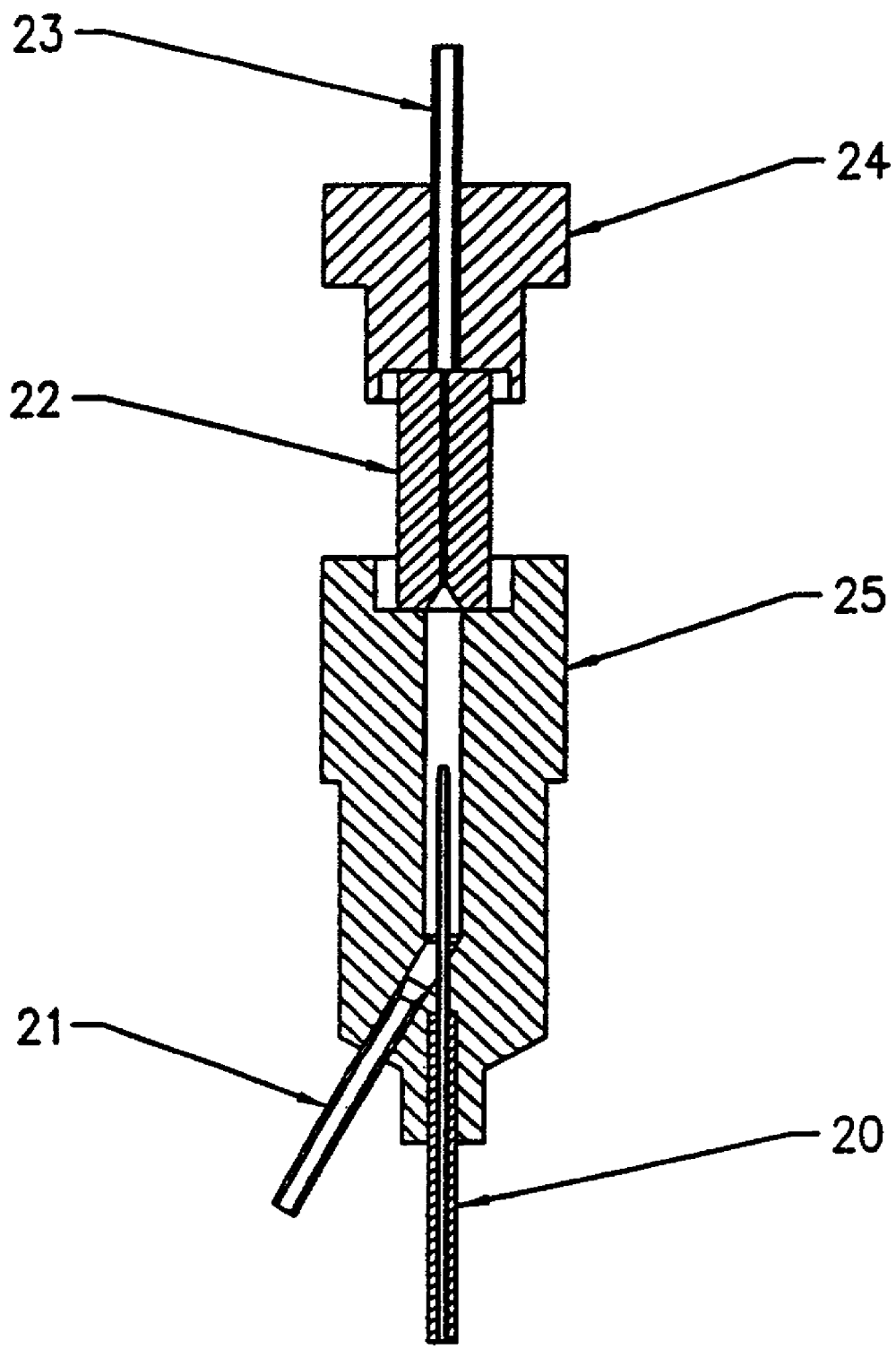
FIG. 2 is a drawing of a flow cell assembly used in an optical detection system of a preferred embodiment of the present invention.
Figure 3:
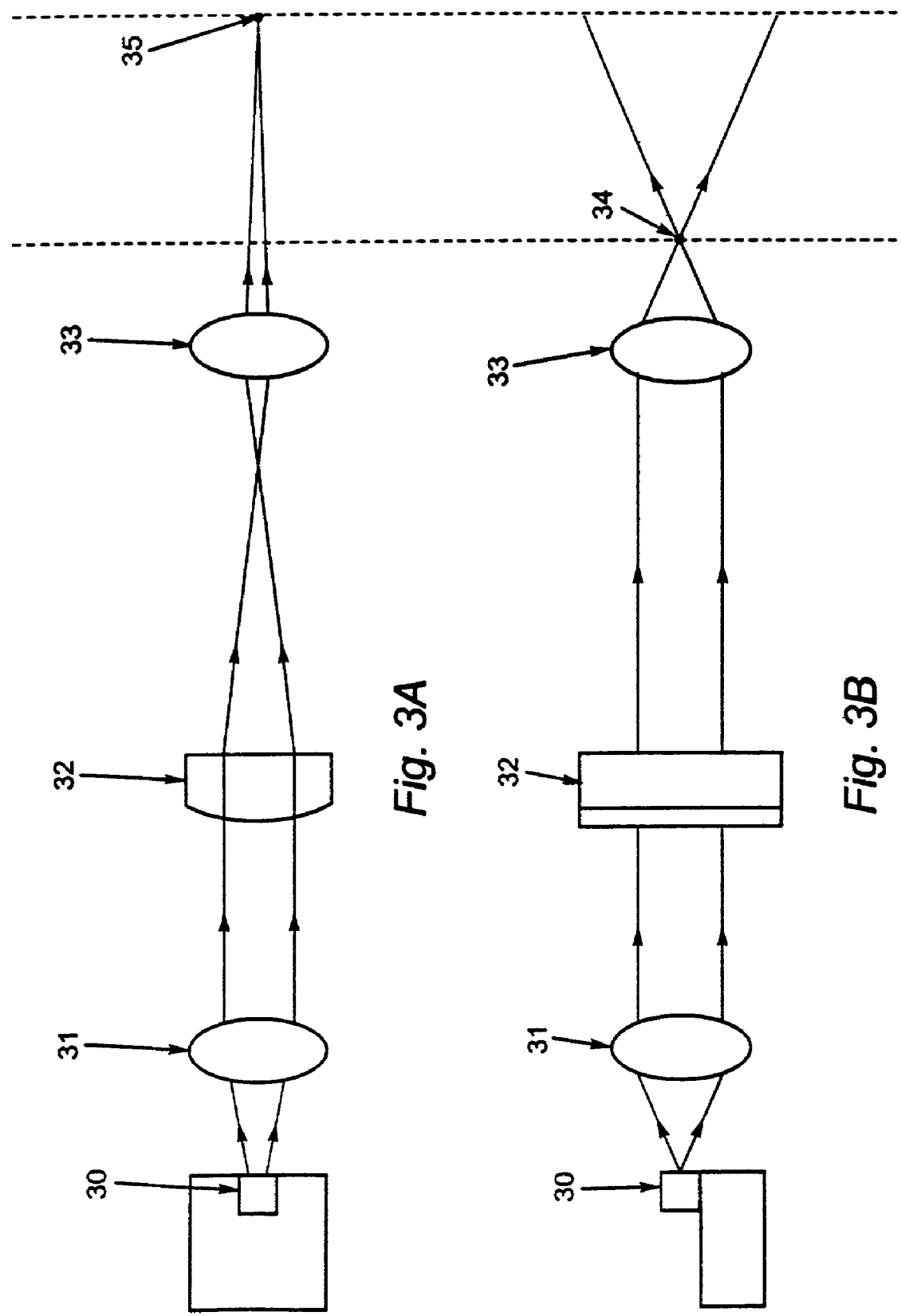
FIG. 3A is a top view schematic representation of a laser beam shaping optic system of a preferred embodiment of the present invention.
FIG. 3B is a side view schematic representation of a laser beam shaping optic system of a preferred embodiment of the present invention.

Syringe 7 continues to pull the sample slug past valve 3, and positions it close to valve 5. Valve 3 closes while valve 2 opens, at which point syringe 7 reverses its direction and pushes the slug through valve 2 to the tip of a flow cell 22 (FIG. 2).

Valve 2 then closes, and valve 4 opens, which allows syringes 6 and 7 to be filled from a system sheath solution reservoir 8. Valve 5 then closes, valve 1 opens, and syringes 6 and 7 dispense sheath solution. Syringe 6 dispenses in a range of about 0.01–0.5 µl/sec, and preferably on the order of about 0.05 µl/sec. Syringe 7 dispenses in a range of about 50–250 µl/sec, and preferably on the order of about 100 µl/sec. The sheath solution in syringe 7 is dispensed through a feed tube 21, and the slug of diluted whole blood is pushed by syringe 6 through flow cell 22, and more specifically through flow channel 47. This forms a sheath-confined core stream of diluted whole blood in the flow cell nozzle 25, which transports the stream to the funnel of flow cell 22, and into flow channel 47, where the cells are interrogated by light sources emitting from a beam shaping assembly 41. This stream of fluid passes completely through flow channel 47, and into the tubing of outlet 23, which is affixed to flow cell 22 by flow cell cap 24. This path leads to the system waste 9.

Referring now to FIGS. 3A, 3B, and 4, beam shaping assembly 41 includes a laser diode 30, which emits light that diverges in two perpendicular axes. A collimating lens 31 eliminates the divergence in both axes, and causes the light to illuminate a lens 32. Lens 32 acts to converge the laser beam in one axis, such that nearly all of the light from laser diode 30 passes through flow cell 22. A third lens 33 is introduced between lens 32 and the flow channel 47 of flow cell 22, such that focal point 34 in flow channel 47 is produced. Focal point 34 of lens 33 is thus in flow channel 47, and a second focal point 35 of lens 32 is the preferred location at which to place photodetector array 48 (FIG. 4).

Figure 27:
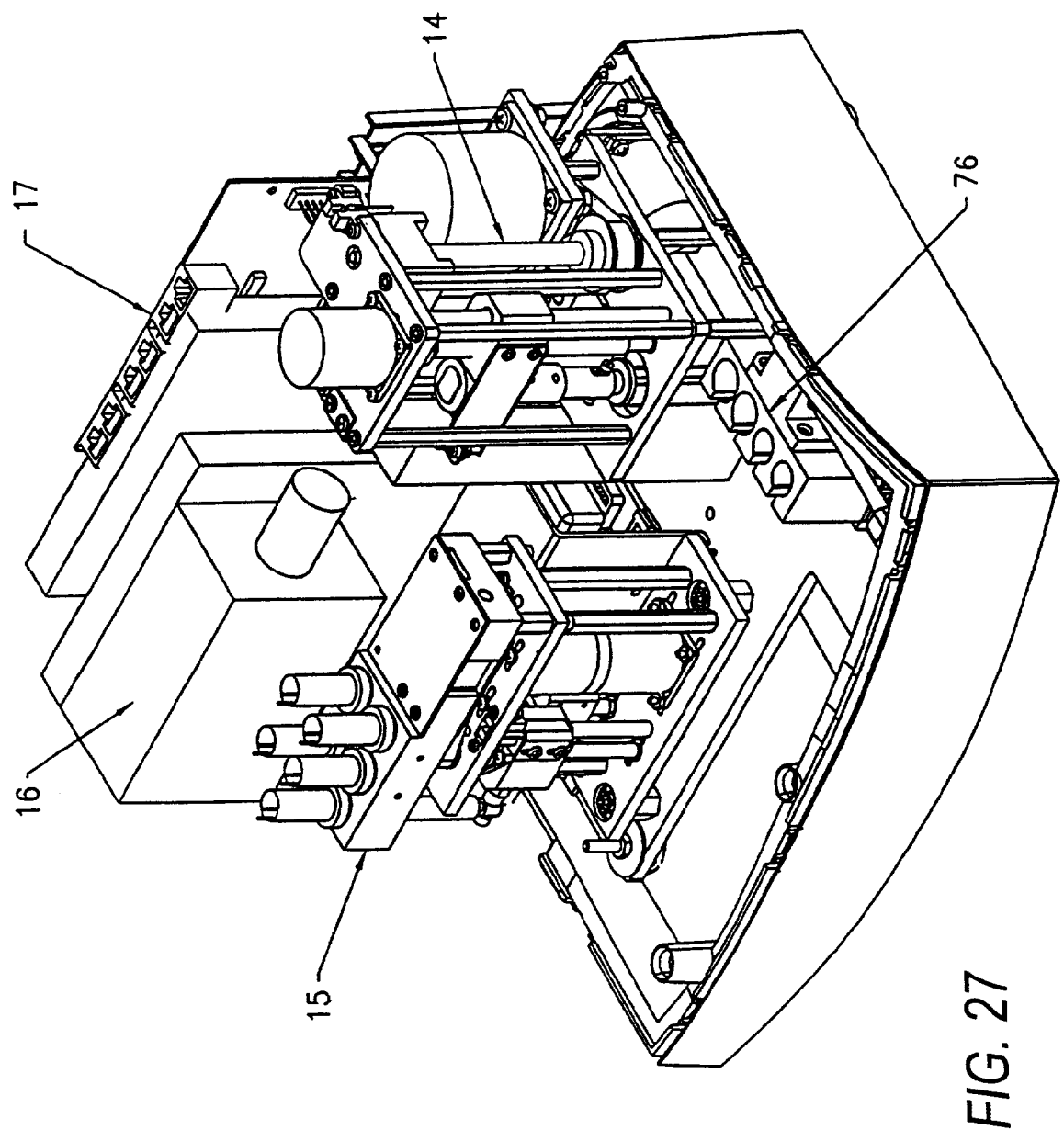
FIG. 27 is a system drawing showing the major sub-assemblies of the present invention.

As the fluid stream passes through flow channel 47, beam shaping assembly 41 illuminates the cells of the diluted whole blood sample individually. The cells pass through first focal point 34, where the light power incident upon the cells is maximized. As cells pass through the light beam of laser 30 at first focal point 34, the quantity and quality of light incident upon photodiodes 42, 43, 44 and 45 is altered. These changes are captured by the system signal processing electronics (FIG. 26), and stored via the system electronics (FIG. 25). These system electronics assemblies 17 are shown in their context in the entire system in FIG. 27.

Photodetector array 48 includes at least two, but most preferably four, photodiode detectors. No collection or imaging lenses are required. These photodiode detectors may include two or more of an axial light loss detector 44, a low-angle forward scattered light detector 45, and a high-angle forward scattered light detector 43. In addition, a right angle scattered light detector 42 (also referred to herein as a high numerical aperture detector) may be included in the instrument, but would be separate from the rest of the photodetectors and would not be mounted onto photodetector array 48. FIG. 5 is a drawing of a photodiode mask 50, which can be used to cover photodetector diodes 43, 44, and 45 to provide three independent light measurements in the direction forward of the laser beam. In this embodiment, low-angle forward scattered light passes through mask portion 51, axial light loss is measured through mask portion 52, and high-angle forward scattered light passes through mask portion 53. Photodiode mask 50 is useful to limit the amount of light from sources other than these that passes through each of detectors 43, 44, and 45. Preferably, mask portions 51, 52, and 53 are on a single fabricated piece of semiconductor material, where only the areas of the desired geometries of mask portions 51, 52, and 53 are active portions of the semiconductor material. Alternatively, photodiode mask 50 could comprise a metal mask that is positioned atop photodetector diodes 43, 44, and 45. The entire contents of the optical system depicted in FIGS. 2 through 5, is shown in its packaged form as optical assembly 16.

Figure 10A:
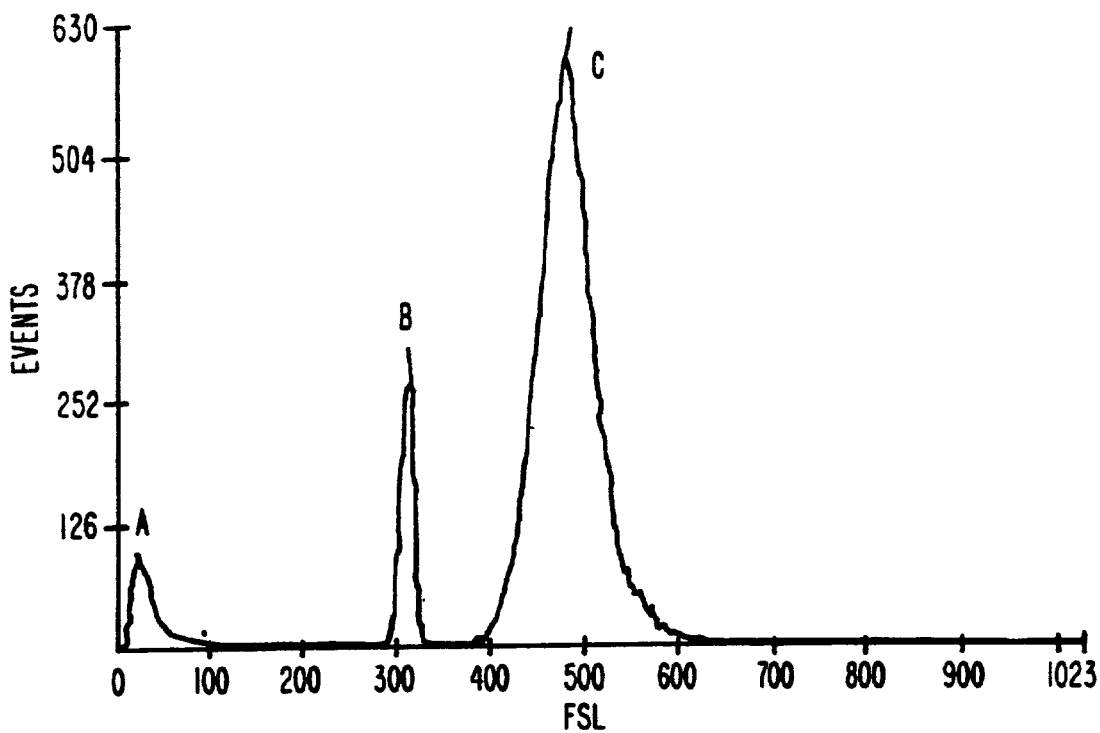
FIG. 10A is a histogram of digitized data collected from an unlysed whole blood sample, in the presence of added latex particles, by a preferred embodiment of the present invention. Low-angle forward scatter channel (FSL) data is shown on the x-axis, and the number of events (or occurrences) collected for each of the individual channels are shown on the y-axis. A=platelet events. B=latex particle events. C=red blood cell events.
Figure 10B:
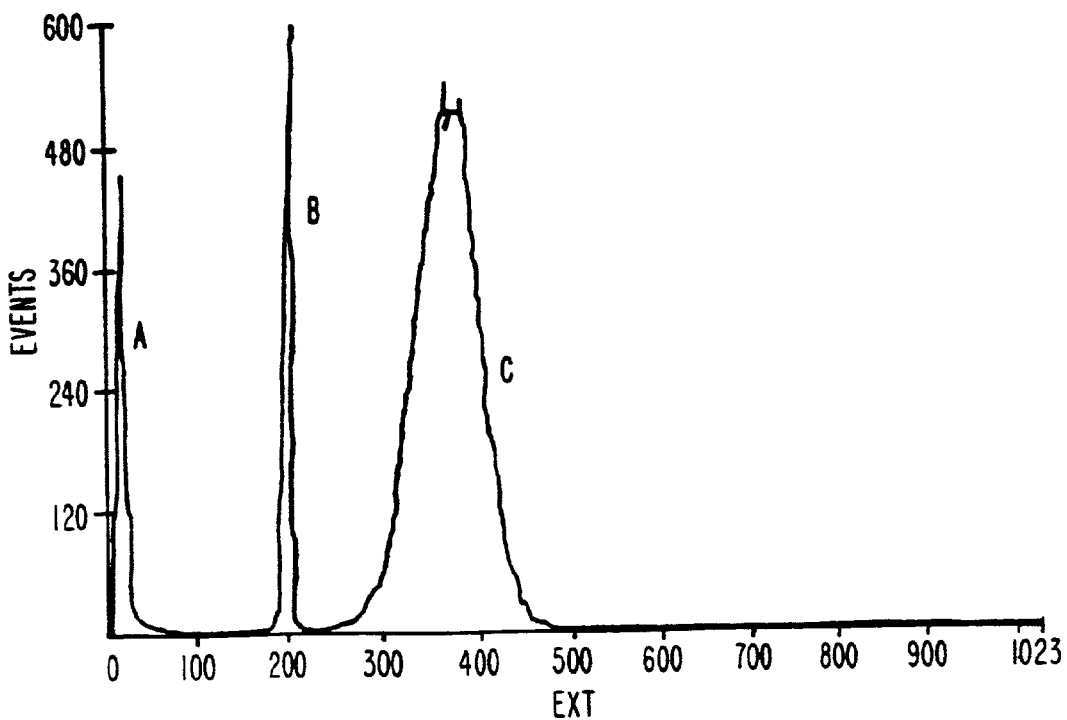
FIG. 10B shows data collected from the same sample as in FIG. 10A, except
Figure 10C:
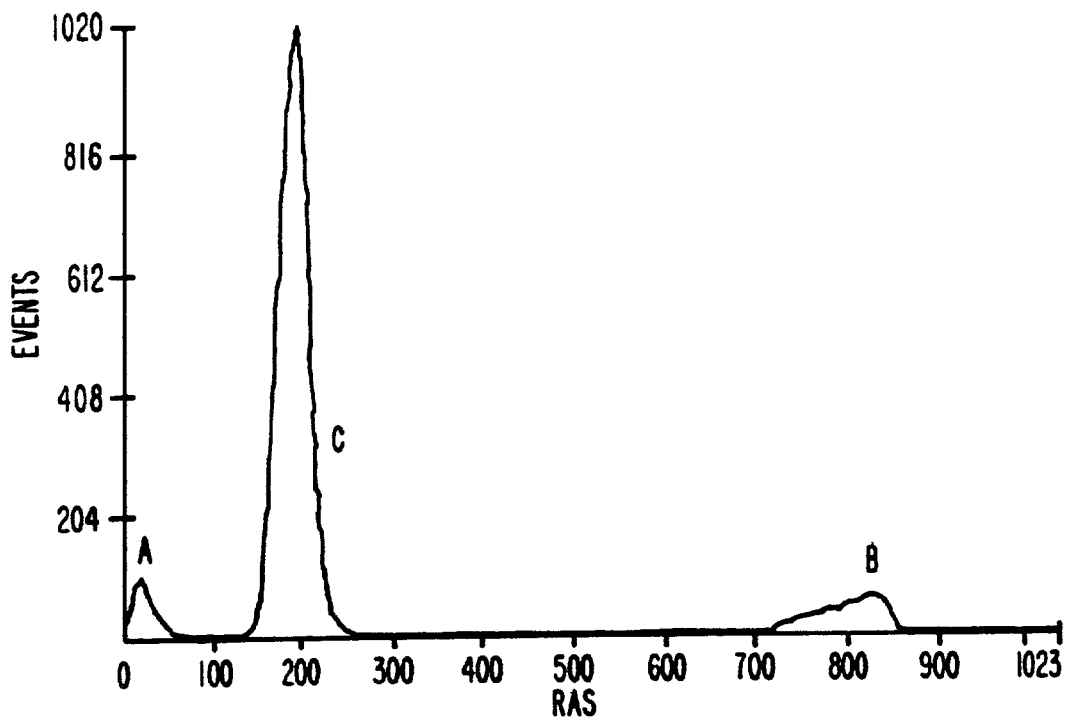
FIG. 10C shows data collected from the same sample as in FIG. 10A, except
Figure 10D:
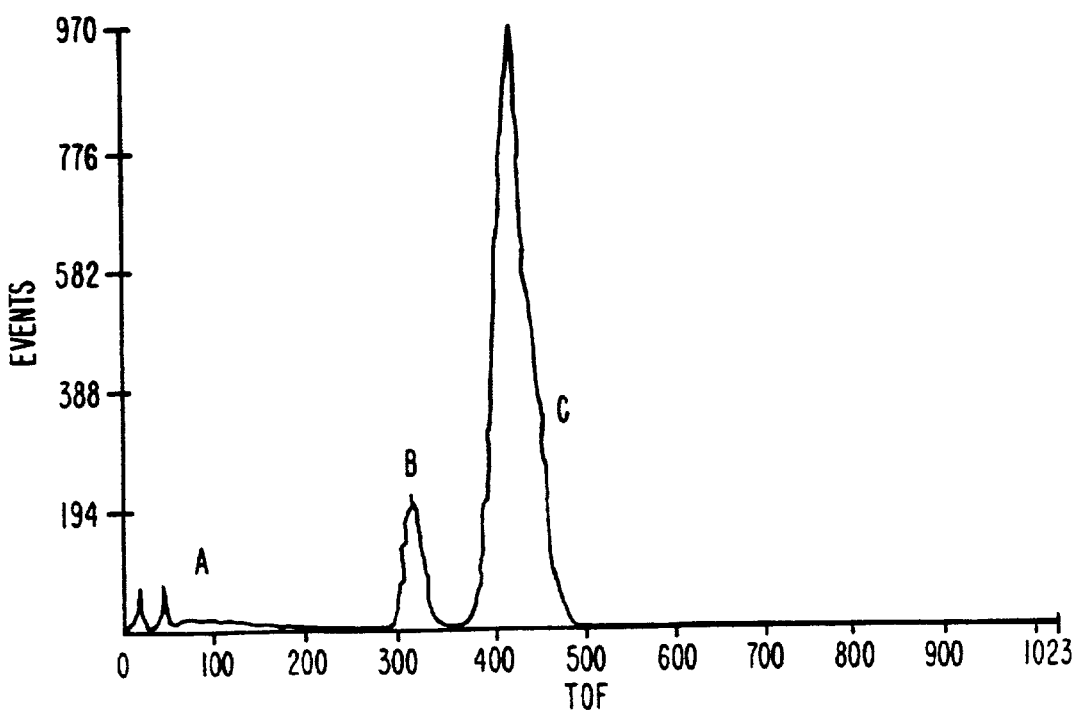
FIG. 10D shows data collected from the same sample as in FIG. 10A, except
Figure 11A:
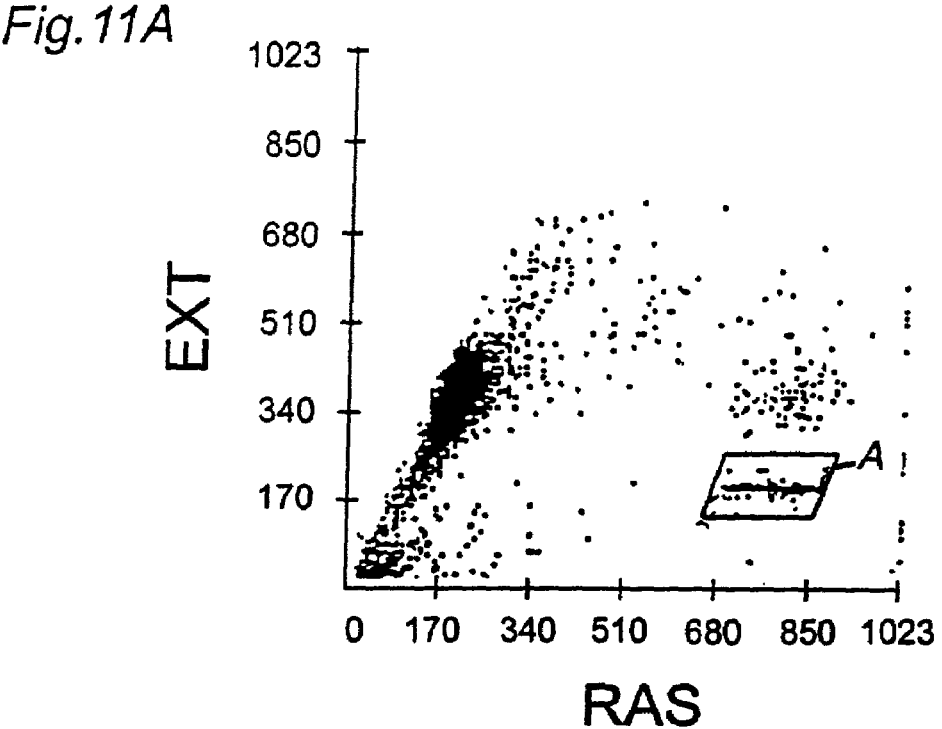
FIG. 11A displays the red cell, platelet and latex particle data from FIGS. 10B and 10C, in scatter-plot form. Scatter plots are a representation of different data collected simultaneously from a cell or particle. Data collected from one particle is plotted on the x-axis against data from another particle on the y-axis.
Figure 11B:
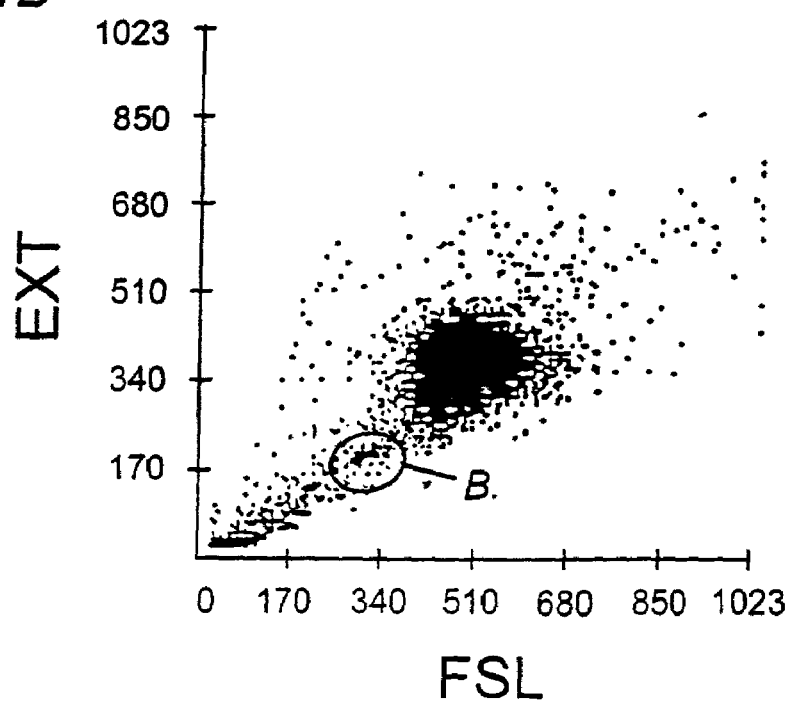
FIG. 11B displays the red cell, platelet and latex particle data from FIGS. 10A and 10C, in scatter-plot form.

FIG. 10A shows data which has been collected for the forward scatter low (FSL) signal from detector 45. FIG. 10B shows data which has been collected for the extinction or axial light loss (EXT) signal from detector 44. FIG. 10C shows data which has been collected for the right angle scatter (RAS) signal from detector 42. FIG. 10D shows pulse width data which has been collected from the forward scatter low (FSL) signal from detector 45, but measures the time of flight, or the time the cell is interrogated by the laser beam. These data are useful to determine cell size. For FIGS. 10A, 10B, 10C and 10D, the peaks shown represent platelet events (A), latex particle events (B), and red blood cell events (C). The same data is shown in a scatter plot form in FIGS. 11A and 11B. For FIG. 11A, the dots in box A represent the latex particle events, and in FIG. 11B, the dots in box B represent latex particle events. Scatter plot data may be represented by any pair derived from the set of EXT, FSL, FSH, RAS, and TOF measurements.

Figure 14A:
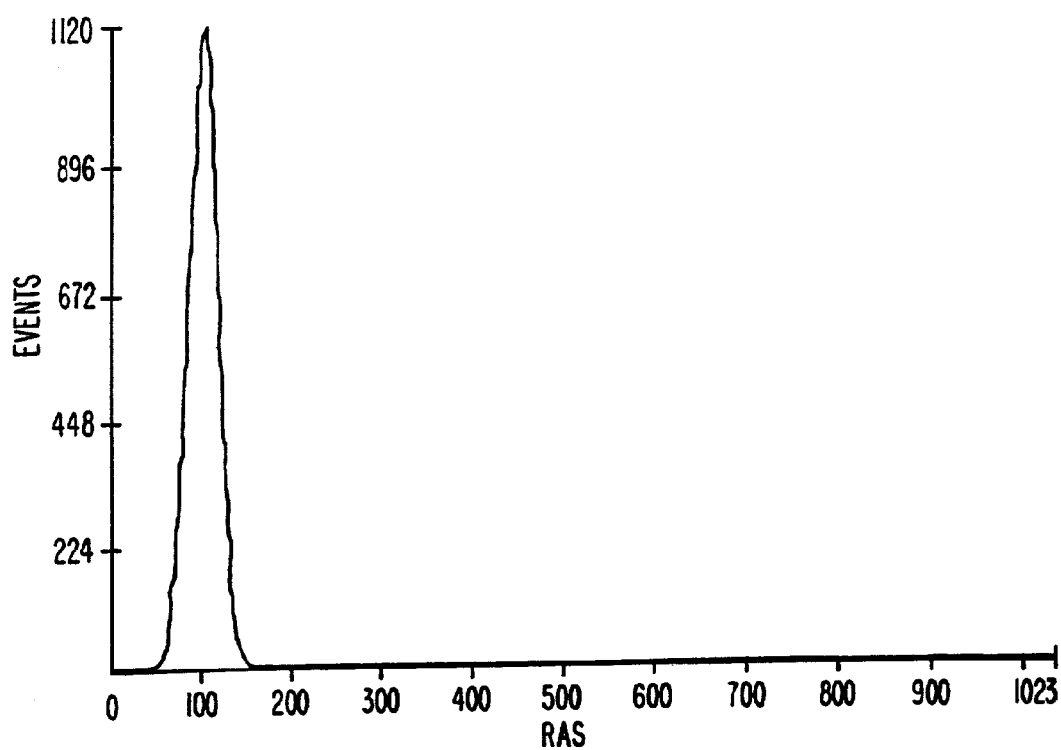
FIG. 14A displays red cell and reticulocyte histogram data for right angle scatter (RAS) from a human whole blood sample in the absence of added latex particles, as measured using the device of the present invention. No separation of the cell types is evident in the histogram, which shows a single peak.
Figure 14B:
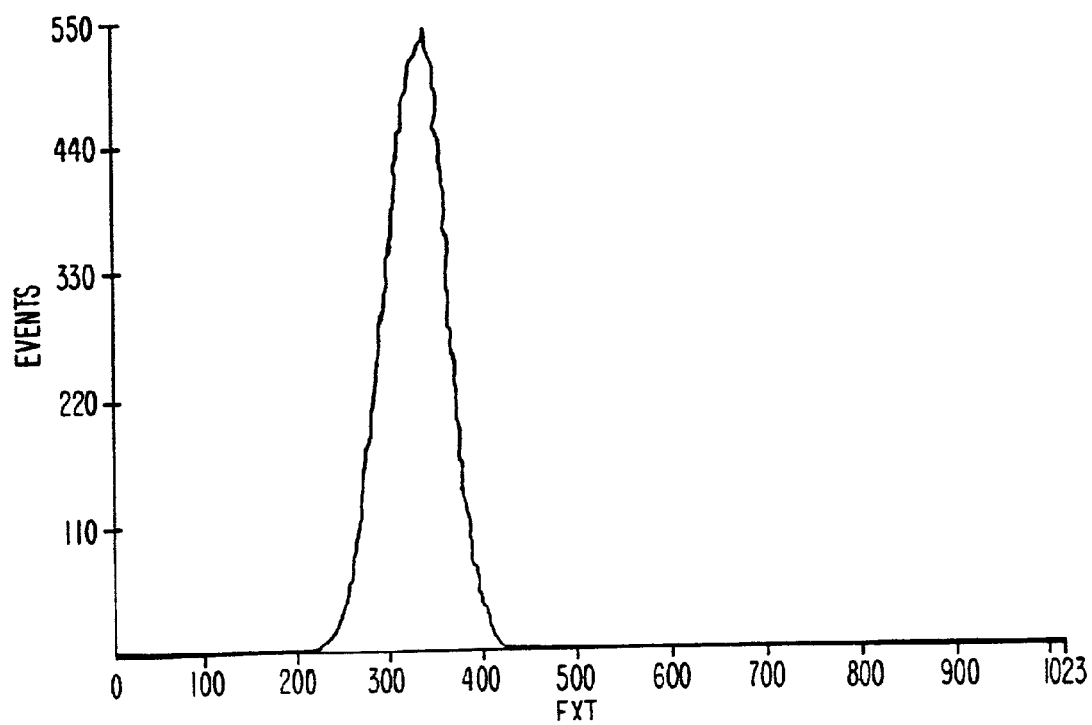
FIG. 14B displays red cell and reticulocyte histogram data for the extinction channel (EXT) from a human whole blood sample in the absence of added latex particles, as measured using the device of the present invention. No separation of the cell types is evident in the histogram, which shows a single peak.
Figure 15:
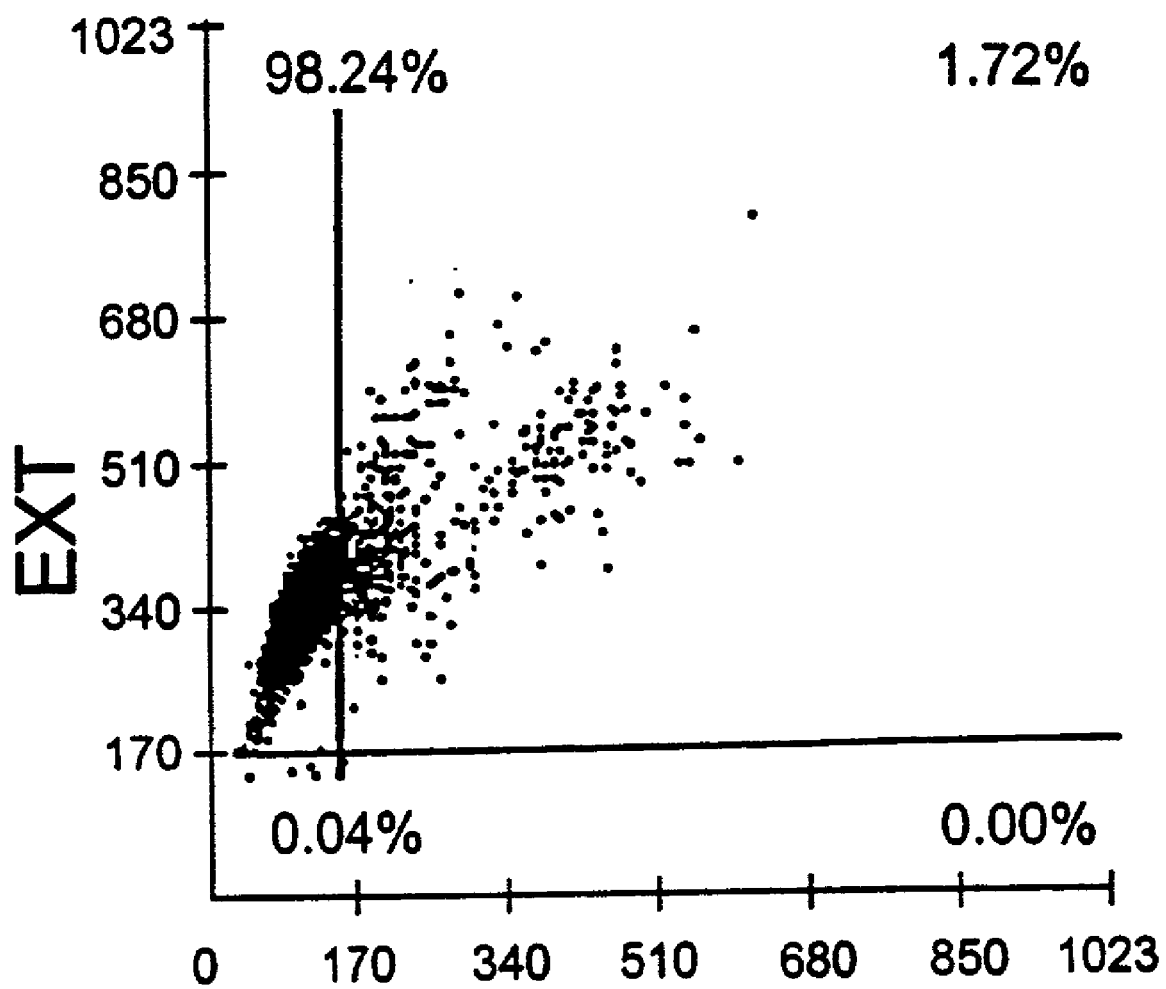
FIG. 15 displays red cell and reticulocyte scatter-plot data obtained from the human whole blood sample of FIGS. 14A and 14B. The extinction (EXT) data are plotted on the y-axis, and the right angle scatter (RAS) data on the x-axis.

Should the reagents used in creating this dilution use an RNA staining dye, such as new methylene blue, the data can be further analyzed by measuring the red blood portions (designated C) in FIGS. 10A–10D to evaluate reticulocyte counts. Histogram of such analysis are shown in FIGS. 14A and 14B, and a scatter plot is shown in FIG. 15. FIG. 15 shows a calculated reticulocyte population of 1.72%. This compares favorably with a 1.60% reticulocyte count, as determined from the same sample by a manual method.

After successfully counting and classifying the red blood cell, reticulocyte, platelet and latex particle populations, needles 11 and 12 are withdrawn from consumable tube 61. Carriage positioning assembly 76 moves the whole blood sample tube so it is again positioned under needles 11 and 12. Needles 11 and 12 are then moved by motor 81 to pierce the whole blood sample tube's septum, and continue to penetrate the tube until both needles 11 and 12 come in contact with the surface of the blood sample. This ensures that the orifice of hydraulic needle 11 is completely immersed in the blood sample, but the orifice of pneumatic vent needle 12 is not. Opening valve 3, and moving syringe 6, causes a portion of the blood sample to be pulled into the tip of needle 11. Ideally, 100 microliters will be aspirated for this portion. Valve 3 is then closed. Needles 11 and 12 are then retracted from the whole blood sample tube. Needles 11 and 12 are wiped almost completely clean as they are withdrawn through the septum. Carriage positioning assembly 76 now positions consumable tube 61 under needles 11 and 12. By moving motor 81, needles 11 and 12 pierce the septum of consumable tube 61, and penetrate the tube until both needles 11 and 12 come in contact with the surface of the solution.

Valves 5 and 3 are opened, while syringe 7, which is filled with the sheath solution, begins to dispense sheath solution. This pushes the 100 microliters of blood sample solution through the tip of needle 11. A volume of sheath fluid follows the whole blood into the consumable tube, which is now represented by 62 in FIG. 6. As the sheath fluid is dispensed into consumable tube 62, motor 81 moves needles 11 and 12 upward, to prevent the orifice of needle 12 from coming into contact with the solution in consumable tube 62. Needles 11 and 12 are next removed from consumable tube 62, and carriage positioning assembly 76 moves a tube of lyse reagent under needles 11 and 12. Motor 81 moves needles 11 and 12 downward to pierce the lyse tube's septum and continues until needles 11 and 12 come in contact with the surface of the lyse. Opening valve 3 and moving syringe 6 pulls lyse into the tip of needle 11. Ideally, 100 microliters of lyse will be aspirated for this portion, which is followed by an air gap created by removing needle 11 from the solution, then moving syringe 6 to pull air into needle 11. Valve 3 is then closed. Needles 11 and 12 are then retracted from the lyse tube. Needles 11 and 12 are wiped almost completely clean as they are withdrawn through the septum. Carriage positioning assembly 76 positions the consumable tube 62 under needles 11 and 12. Valve 5 and 3 are then opened, while syringe 7, which is filled with the system diluent, begins to dispense diluent. This pushes the 100 microliters of lyse through the tip of needle 11. A volume of sheath fluid follows this into the consumable tube, now represented by 63 in FIG. 6. As the sheath fluid is dispensed, motor 81 moves needles 11 and 12 upward, so as to prevent the orifice of needle 12 from coming into contact with the solution.

The solution in consumable tube 63 is fairly homogeneous, but to ensure homogeneity, valves 3 and 5 are closed, and the needles are withdrawn from consumable tube 63. Consumable tube 63 is then moved to the mix position under mixer assembly 80, and mixed by spinning, as describe above. During this process, valves 3 and 5 are opened, and syringe 7 creates an air gap at the tip of needle 11.

Carriage positioning assembly 76 moves consumable tube 63 under needles 11 and 12. Motor 81 moves needles 11 and 12 downward to pierce the septum of consumable tube 63 until needles 11 and 12 come in contact with the surface of the solution. Syringe 7 then aspirates a predetermined volume of solution into the tip of needle 11. Needles 11 and 12 are withdrawn by motor 81 from the solution, but not completely from consumable tube 63. This creates a slug of the lysed whole blood in needle 11. Syringe 7 pulls this slug of lysed whole blood through HGB module 10, where absorption at four separate wavelengths of light is measured. Red blood cells have been lysed in this slug, freeing hemoglobin from the cells. FIG. 19A shows absorption data, where cyanide was used in the lysing agent to label the HGB. FIG. 19B shows absorption data where only a lytic agent was used. FIG. 21 shows absorption data where cell lysis occurred in the presence of a reticulocyte dye. The volume of the lysed sample slug can also be evaluated at this point by evaluating the change in absorption values in the detector channels as the air gaps on each side of the slug pass through the detector channels. By evaluating the time taken for the absorption values to change, and knowing the rate of sample movement through the detectors, the volume of the lysed sample slug can be easily calculated. If the volume of the lysed sample slug deviates by a predetermined amount from that expected, an error message can be displayed to the user, and the sample analysis halted until the problem is fixed.

Syringe 7 continues to pull the lysed sample slug past valve 3 and close to valve 5. Valve 3 closes and valve 2 opens, at which point syringe 7 reverses its direction and pushes the slug through valve 2 to the tip of flow cell assembly 20.

Valve 2 then closes, and valve 4 opens, which allows syringes 6 and 7 to be filled from a system diluent reservoir 8. Valve 5 then closes, valve 1 opens, and syringes 6 and 7 dispense sheath solution. Syringe 6 dispenses in a range of about 0.1–1.0 μl/sec, and preferably on the order of about 0.5 μl/sec. Syringe 7 dispenses in a range of about 50–250 μl/sec, and preferably on the order of about 100 μl/sec. The sheath solution in syringe 7 is dispensed through feed tube 21, and the slug of lysed whole blood is pushed by syringe 6 through flow cell 22. This forms a sheath-confined core stream of lysed whole blood in flow cell nozzle 25, which transports the stream to the funnel of flow cell 22, where the cells are interrogated by light sources emitting from optical assembly 41. This stream of fluid passes completely through flow cell 22, and into the tubing of outlet 23, which is affixed to flow cell 22 by flow cell cap 24. This path leads to the system waste 9.

As the fluid stream passes through flow cell 22, optical assembly 41 illuminates the cells of the lysed whole blood individually. The cells pass through first focal point 34 of laser 30. At first focal point 34, the light power incident upon the cells is maximized. This narrow focus at first focal point 34 is generated by lens 33. As cells pass through the light beam of laser 30 at first focal point 34, the quantity and quality of light incident upon photodiodes 42, 43, 44 and 45 is altered. These changes are captured by the system signal processing electronics (FIG. 26), and stored via the system electronics (FIG. 25). Examples of data collected in this manner are shown FIGS. 12A through 12F.

Figure 12A:
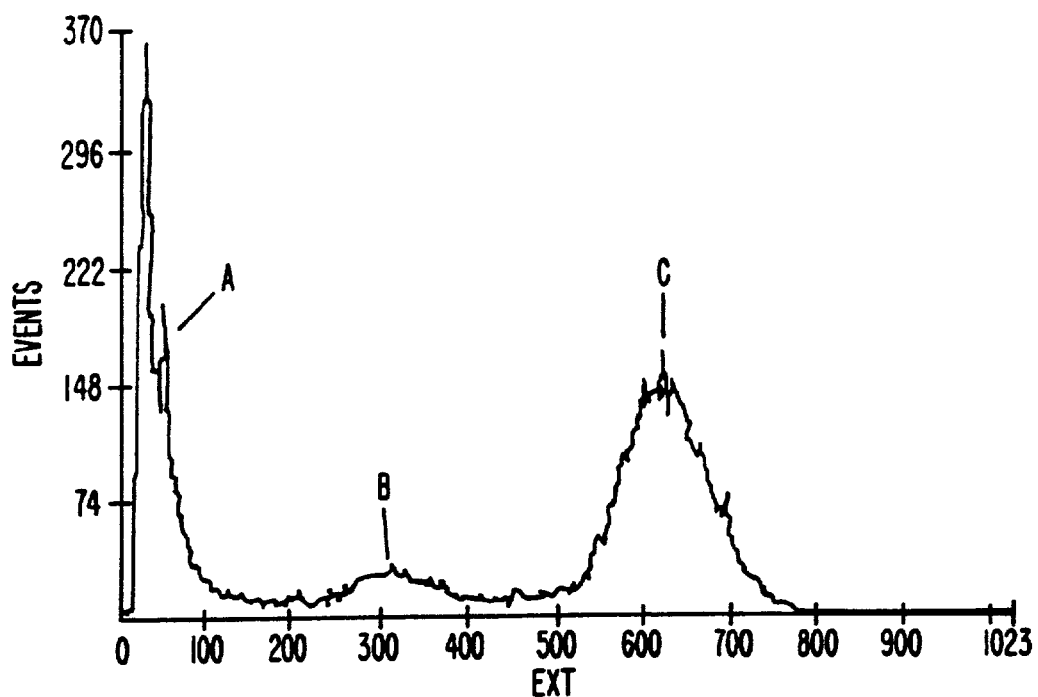
FIG. 12A is a histogram of digitized data collected from a lysed whole blood sample, in the absence of added latex particles, by a preferred embodiment of the present invention. The extinction (EXT) channel data are shown on the x-axis, and the number of events (or occurrences) collected for each of the individual channels are shown on the y-axis. A=lymphocytes; B=monocytes; and C=granulocytes.
Figure 12B:
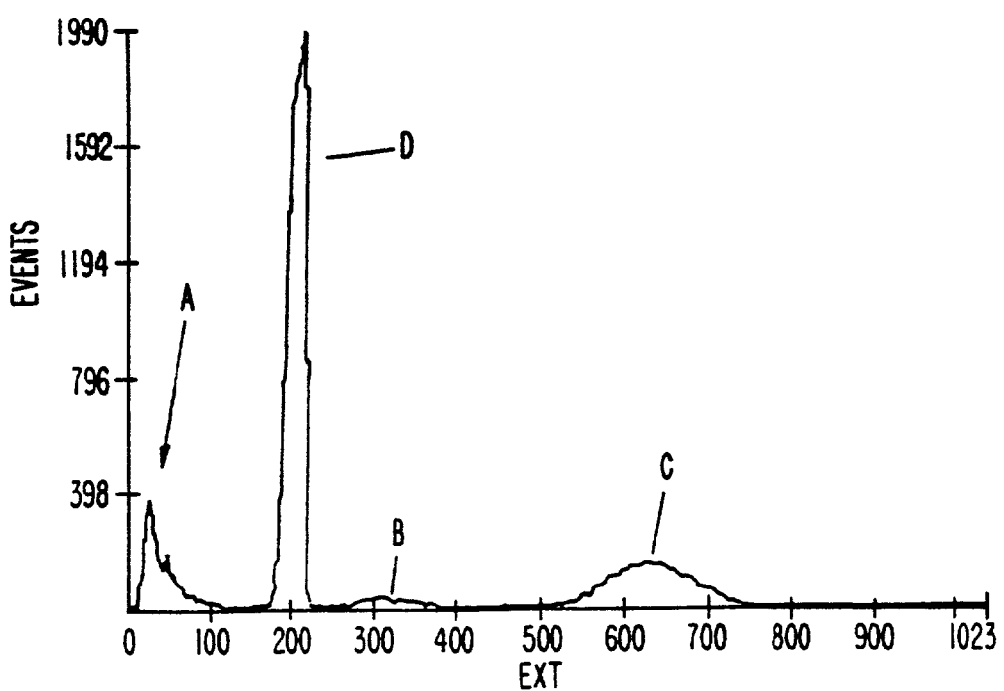
FIG. 12B is a histogram of digitized data collected from a lysed whole blood sample, in the presence of added latex particles, by a preferred embodiment of the present invention. The extinction (EXT) channel data are shown on the x-axis, and the number of events (or occurrences) collected for each of the individual channels are shown on the y-axis. A=lymphocytes; B=monocytes; C=granulocytes; and D=latex particles.
Figure 12C:
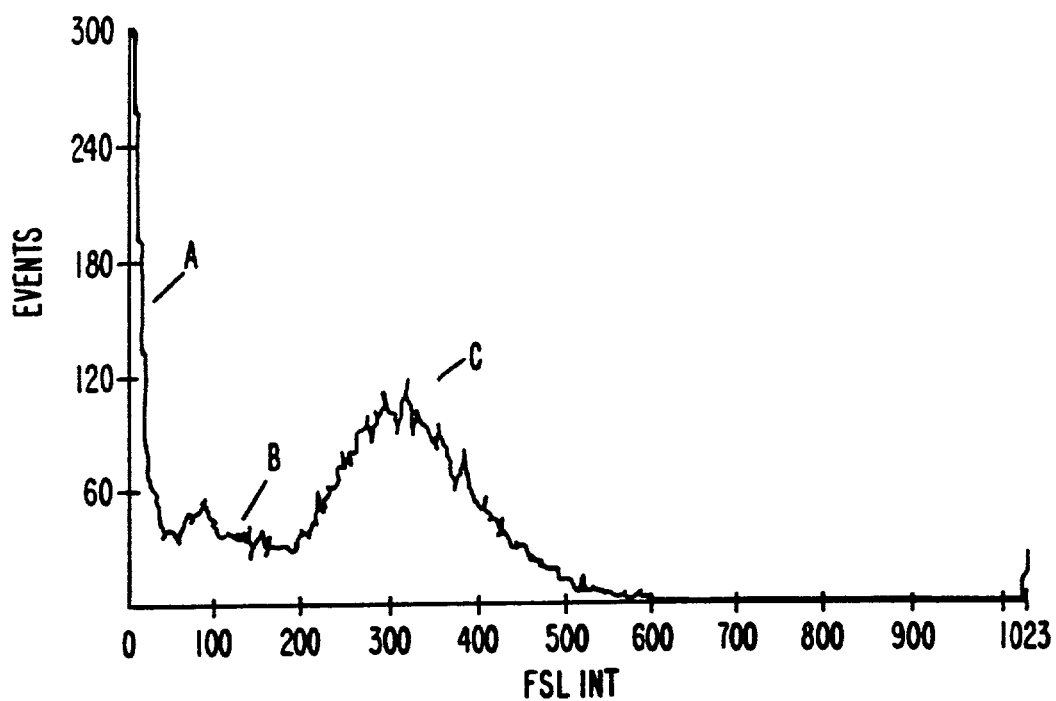
FIG. 12C is a histogram of digitized data collected from a lysed whole blood sample, in the absence of added latex particles, by a preferred embodiment of the present invention. The forward low scattered light (FSL) channel data are shown on the x-axis, and the number of events (or occurrences) collected for each of the individual channels are shown on the y-axis. A=lymphocytes; B=monocytes; and C=granulocytes.
Figure 12D:
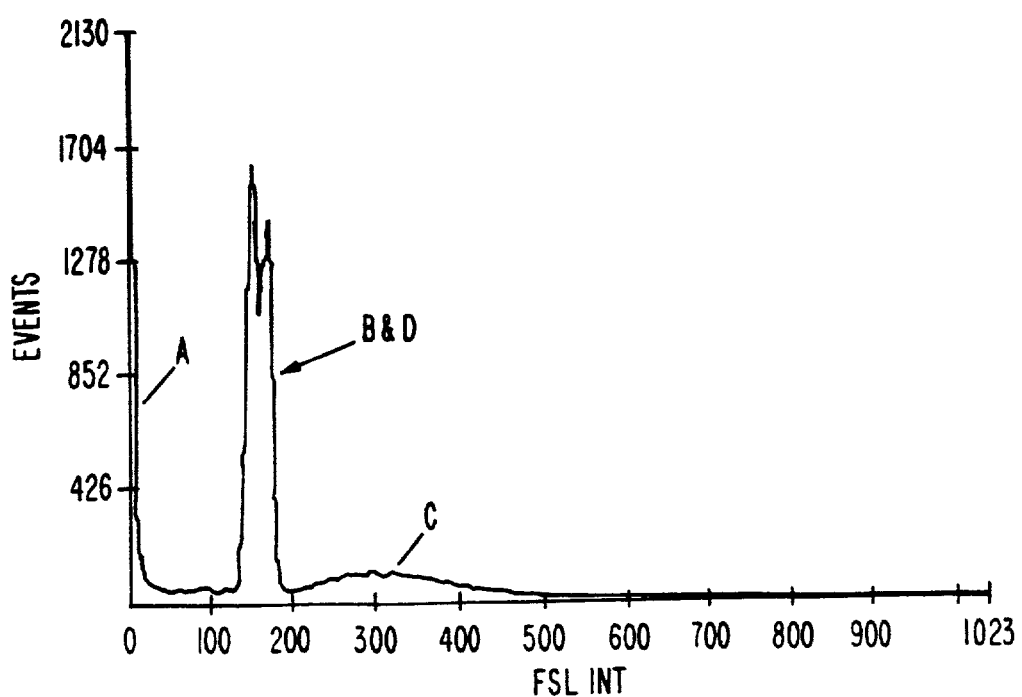
FIG. 12D is a histogram of digitized data collected from a lysed whole blood sample, in the presence of added latex particles, by a preferred embodiment of the present invention. The forward low scattered light (FSL) channel data are shown on the x-axis, and the number of events (or occurrences) collected for each of the individual channels are shown on the y-axis. A=lymphocytes; B=monocytes; C=granulocytes; and D=latex particles.
Figure 12E:
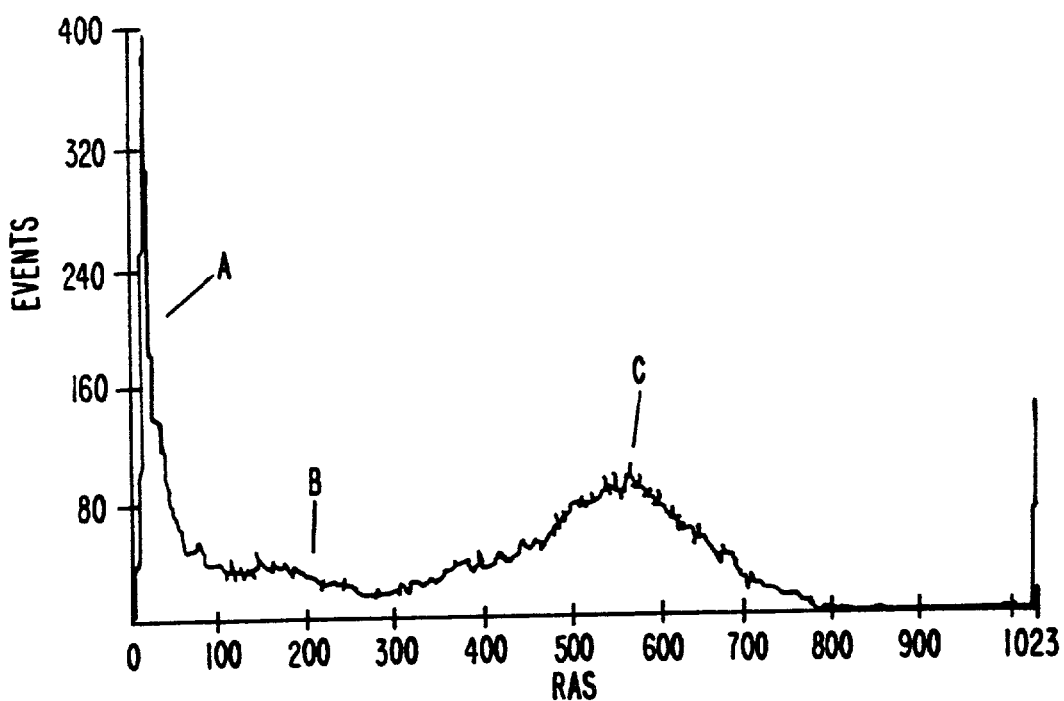
FIG. 12E is a histogram of digitized data collected from a lysed whole blood sample, in the absence of added latex particles, by a preferred embodiment of the present invention. The right angle scattered light (RAS) channel data are shown on the x-axis, and the number of events (or occurrences) collected for each of the individual channels are shown on the y-axis. A=lymphocytes; B=monocytes; and C=granulocytes.
Figure 12F:
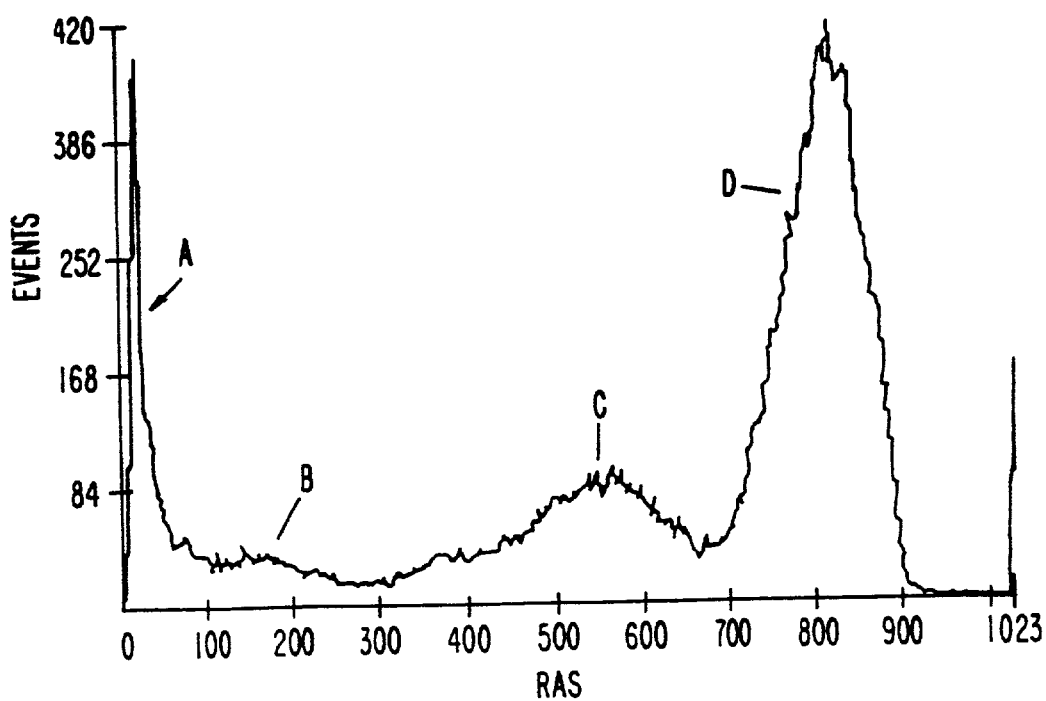
FIG. 12F is a histogram of digitized data collected from a lysed whole blood sample, in the presence of added latex particles, by a preferred embodiment of the present invention. The right angle scattered light (RAS) channel data are shown on the x-axis, and the number of events (or occurrences) collected for each of the individual channels are shown on the y-axis. A=lymphocytes; B=monocytes; C=granulocytes; and D=latex particles.

FIG. 12A presents data which has been collected for the extinction or axial light loss (EXT) signal from detector 44 in the absence of latex particles. FIG. 12B shows the same sample with latex present. FIG. 12C presents data collected for the forward scatter low signal (FSL) from detector 45 in the absence of latex particles. FIG. 12D shows the same sample in the presence of latex particles. FIG. 12E presents data collected for the right angle scatter (RAS) signal from detector 42 in the absence of latex particles, and FIG. 12F shows the same sample with latex particles present.

Figure 13A:
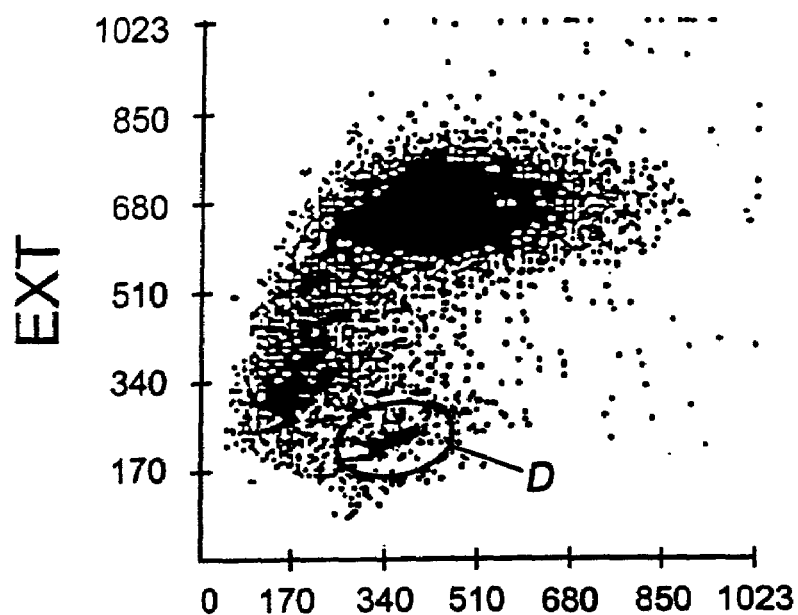
FIG. 13A is a scatter plot of the FSL channel data for white cells from the human whole blood sample of FIGS. 12B (EXT) and 12D (FSL), in the presence of added latex particles, as measured using a preferred embodiment of the present invention. D=latex particles.
Figure 13B:
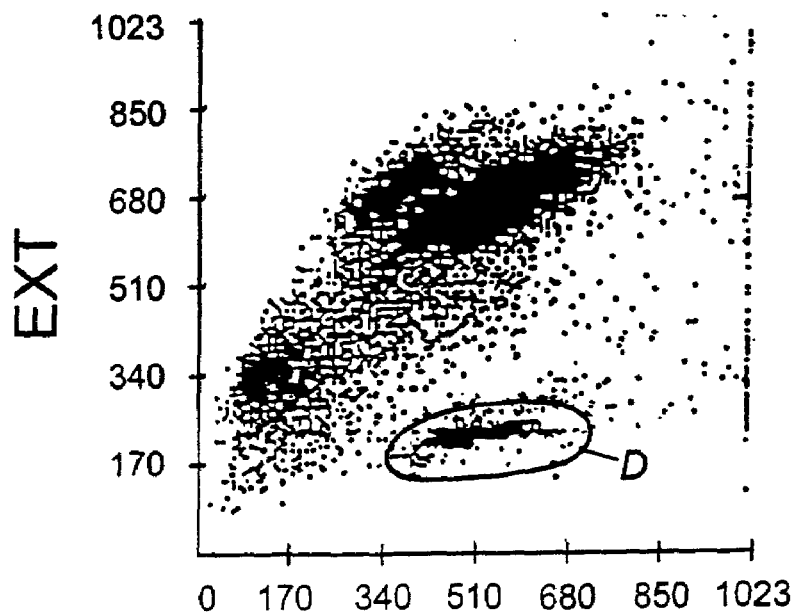
FIG. 13B is a scatter plot of the RAS channel data for white cells from the human whole blood sample of FIGS. 12B (EXT) and 12F (RAS), in the presence of added latex particles, as measured using the device of the present invention. D=latex particles.

For FIGS. 12A through 12F, the peaks shown represent lymphocyte events (A), monocyte events (B), granulocyte events (C), and latex particle events (D). This same data is shown in a scatter plot form in FIGS. 13A and 13B. For FIGS. 11A and 11B, the dots in circle D represent the latex particle events. Scatter plot data may be represented by any pair derived from the set of EXT, FSL, FSH, RAS, and TOF measurements.

Figure 16A:
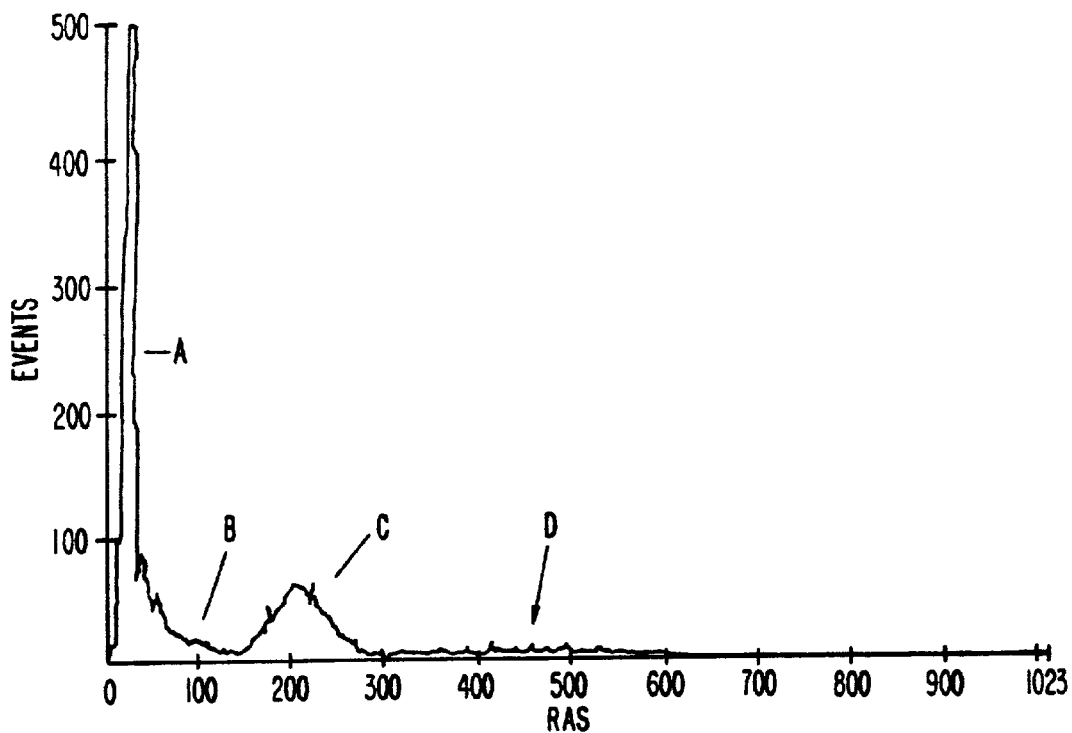
FIG. 16A displays white cell differential histogram right angle scattered light (RAS) data obtained from a human whole blood sample using the device of the present invention. A=lymphocytes; B=monocytes; C=neutrophils; and D=eosinophils.
Figure 16B:
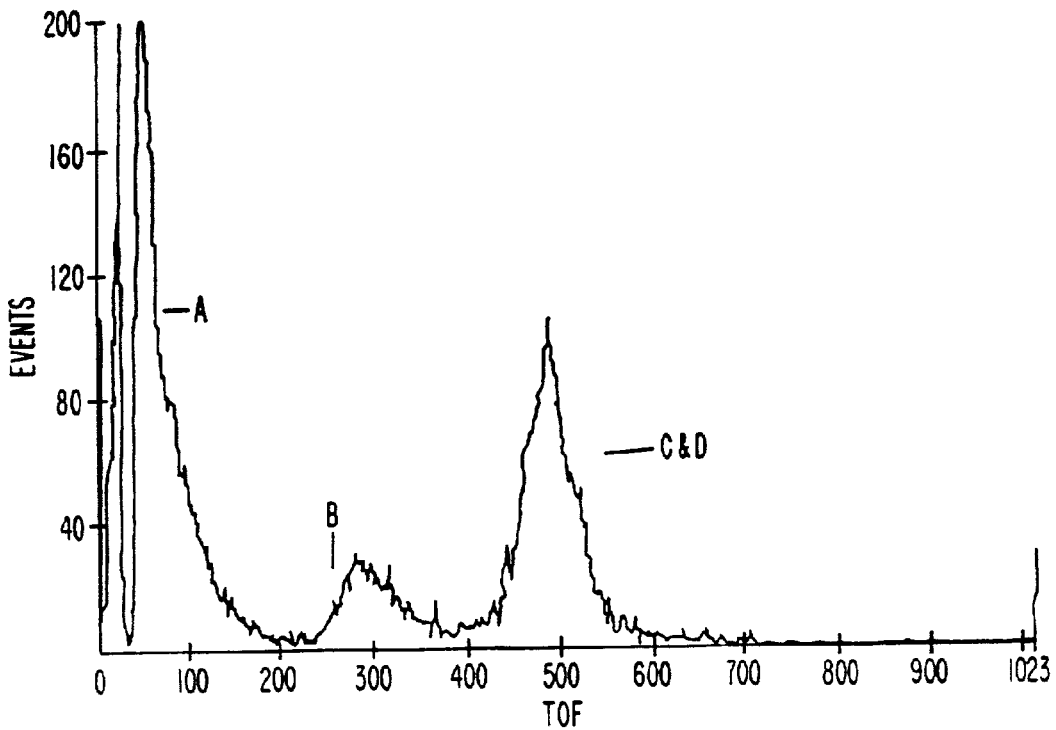
FIG. 16B displays white cell differential histogram time-of-flight (TOF) data obtained from a human whole blood sample using the device of the present invention. A=lymphocytes; B=monocytes; C=neutrophils; and D=eosinophils.
Figure 17:
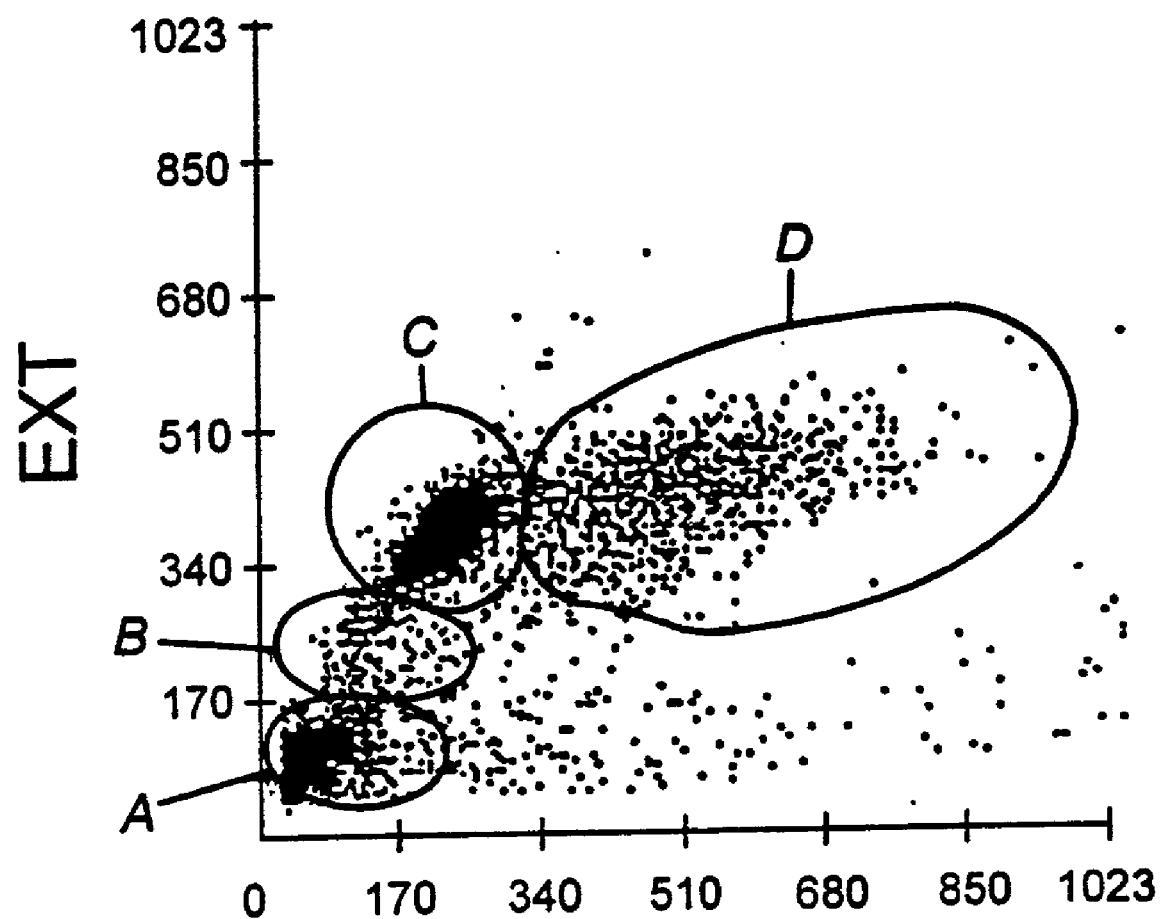
FIG. 17 displays white cell differential scatter-plot data obtained from the same sample as depicted in FIGS. 16A and 16B. Here, when plotted against each other, the extinction (EXT) (y-axis) and the right angle scatter (RAS) (x-axis) show the separation of several elements of the white cell differential. A=lymphocytes; B=monocytes; C=neutrophils; and D=eosinophils. The value calculated for the concentration of eosinophil cells present in D is 20.63% of the total, which is in excellent agreement with a value of 21.70% eosinophils obtained by a manual reference method.

For samples which contain eosinophils in the granulocyte population, eosinophil detection is achieved in the right angle scatter channel of detector 42. FIG. 16A shows the histogram of data derived from a lysed whole blood sample, where A represents lymphocytes, B monocytes, C neutrophils, and D eosinophils. FIG. 17 shows the same data as FIG. 16, but in scatter plot form. The encircled populations represent lymphocytes (A), monocytes (B), neutrophils (C), and eosinophils (D). Any pair of up to four detectors and time of flight measurements could be represented by scatter plot data, but to distinguish eosinophils, right angle scatter is necessary.

After the white blood cells have been counted and classified, syringe 7 is charged with fluid from reagent reservoir 8, by opening valve 4. Valve 4 closes and valves 3 and 5 open, which allows syringe 7 to clean the sample lines by back-flushing fluid into consumable tube 63 through needle 11. Needle 12 acts to vent the tube through filter 13, to atmosphere. This yields a consumable tube of the configuration shown in 64 in FIG. 6. Carriage positioning assembly 76 now moves to its home position, where the user can open the system door, and remove the tubes from the carriage slots. Consumable tube 64 is now a waste tube, and is discarded. The lyse solution tube remains in the instrument until its contents are depleted.

Other modes of operation, along the same lines as described above would allow for immunoassay to be performed by latex agglutination techniques. Here the consumable would contain latex particles that are coated with an antibody, such that the particles would clump together in the presence of the proper analyte. This latex particle mixture would be run through the optical channel described in FIG. 4, and the data would be evaluated for doublets or triplet particle clumps. The higher the concentration of these particle clumps, the higher the concentration of the analyte of interest.

Various patents and publications are cited herein, and their disclosures are hereby incorporated by reference in their entireties. The present invention is not intended to be limited in scope by the specific embodiments described herein. Although the present invention has been described in detail for the purpose of illustration, various modifications of the invention as disclosed, in addition to those described herein, will become apparent to those of skill in the art from the foregoing description. Such modifications are intended to be encompassed within the scope of the present claims.

What is claimed is:

1. A disposable vessel for use in a flow cytometry-based hematology system, comprising:
   a disposable tube having two closed ends;
   a known number of reference particles in said disposable tube, each of said reference particles having a predetermined diameter such that, when said reference particles are illuminated by light, said light is scattered by said reference particles such that said scattered light falls into at least one of a plurality of predetermined light scatter channels; and
   at least one reagent in said disposable tube.

2. A disposable vessel for use in a flow cytometry-based hematology system, comprising:
   a disposable tube having two closed ends;
   a known number of reference particles in said disposable tube, each of said reference particles having one of a plurality of predetermined diameters such that when said reference particles are illuminated by light from a laser, said light is scattered by said reference particles such that said scattered light falls into one of a plurality of predetermined light scatter channels; and
   at least one reagent in said disposable tube.

3. The disposable vessel of either of claim 1 or 2, wherein said diameter of each of said reference particles is between 1 micron and 10 microns.

4. The disposable vessel of either of claim 1 or 2, wherein said diameter of each of said reference particles is 4.0±0.5 microns.

5. The disposable vessel of either of claim 1 or 2, wherein said known number of reference particles is between about $10^3$ and about $10^5$ per μl of a sample solution.

6. The disposable vessel of either of claim 1 or 2, wherein said know number of reference particles is present at a concentration of 10,000±1,000 per μl of a sample solution.

7. The disposable vessel of either of claim 1 or 2, wherein said reference particles are selected from the group consisting of polystyrene latex particles, fixed cells, pollen, glass, and large colloids.

8. The disposable vessel of either of claim 1 or 2, wherein said reference particles are polystyrene latex particles.

9. The disposable vessel of either of claim 1 or 2, wherein said reference particles are styrene divinylbenzene latex particles.

10. The disposable vessel of claim 4, wherein said known number of reference particles is present at a concentration of 10,000±1,000 per µl of a sample solution.

11. The disposable vessel of either of claim 1 or 2, wherein said reagent is effective to enable said flow cytometry-based hematology system to count at least one of red blood cells and reticulocytes in a blood sample or blood-derived sample.

12. The disposable vessel of either of claim 1 or 2, wherein said reagent is effective to stain one or more cells in a blood sample or blood-derived sample.

13. The disposable vessel of either of claim 1 or 2, wherein said reagent includes a reactant capable of staining ribonucleic acid in reticulocytes.

14. The disposable vessel of claim 13, wherein said reactant capable of staining ribonucleic acid in reticulocytes is new methylene blue.

15. The disposable vessel of claim 14, wherein said new methylene blue is present at a concentration between about 0.1 and about 0.5 grams per liter of a sample solution.

16. The disposable vessel of either of claim 1 or 2, wherein said reagent includes a reactant capable of modifying the shape of red blood cells but otherwise leaving said red blood cells substantially intact for a period of at least one minute.

17. The disposable vessel of claim 16, wherein said reactant capable of modifying the shape of red blood cells but otherwise leaving said red blood cells substantially intact is a nonzwitterionic surfactant.

18. The disposable vessel of claim 17, wherein said nonzwitterionic surfactant is selected from the group consisting of an alkylphenol ethoxylate and an alcohol ethoxylate.

19. The disposable vessel of claim 16, wherein said reactant capable of modifying the shape of red blood cells but otherwise leaving said red blood cells substantially intact is Plurafac-A-39-Prill.

20. The disposable vessel of either of claim 1 or 2, wherein said reagent includes new methylene blue and a nonzwitterionic surfactant.

21. The disposable vessel of either of claim 1 or 2, wherein said reagent includes:
   a) new methylene blue, at a concentration between about 0.1 and about 0.5 grams per liter of a sample solution;
   b) Plurafac-A-39-Prill, at a concentration between about 0.1 and about 0.6 grams per liter of a sample solution;
   c) sodium bicarbonate, at a concentration between about 6.0 and about 10.0 grams per liter of a sample solution;
   d) sodium chloride, at a concentration between about 1.0 and about 5.0 grams per liter of a sample solution;
   e) Tricine, at a concentration between about 1.0 and about 5.0 grams per liter of a sample solution;
   f) disodium EDTA, at a concentration between about 0.5 and about 3.0 grams per liter of a sample solution;
   g) ethyl paraben at a concentration between about 0.1 and about 0.5 grams per liter of a sample solution; and
   h) methyl paraben at a concentration between about 0.1 and about 0.3 grams per liter of sample solution.

22. The disposable vessel of either of claim 1 or 2, wherein said reagent is effective to enable said flow cytometry-based hematology system to measure at least one of a red blood cell count, a reticulocyte count, a platelet count, a two-part white blood cell differential, a five-part white blood cell differential, and hemoglobin concentration.

23. The disposable vessel of either of claim 1 or 2, wherein said reagent is effective to enable said flow cytometry-based hematology system to measure a complete blood count, a five-part white blood cell differential, and a reticulocyte count.

24. The disposable vessel of either of claim 1 or 2, wherein said reagent is effective to enable said flow cytometry-based hematology system to measure platelet aggregation.

25. The disposable vessel of either of claim 1 or 2, wherein said reagent is effective to enable said flow cytometry-based hematology system to utilize one of a clottable assay and an aggregation assay.

26. The disposable vessel of either of claim 1 or 2, wherein said reagent is effective to enable said flow cytometry-based hematology system to utilize a member selected from the group consisting of a prothrombin time assay, an activated partial thromboplastin time assay, and a thrombin time assay.

27. The disposable vessel of either of claim 1 or 2, wherein said reagent comprises a fluorescent compound.

28. The disposable vessel of either of claim 1 or 2, wherein said reagent comprises an antibody or antibody derivative.

29. The disposable vessel of either of claim 1 or 2, wherein said reagent comprises a member selected from the group consisting of an enzyme, an enzyme substrate, and an enzyme inhibitor.

30. The disposable vessel of either of claim 1 or 2, wherein said reagent comprises a member selected from the group consisting of a receptor, a receptor body, a receptor agonist, and a receptor antagonist.

31. The disposable vessel of either of claim 1 or 2, wherein said disposable vessel is a closed tube.

32. The disposable vessel of either of claim 1 or 2, wherein said known number of reference particles is between about $10^3$ and about $10^5$ per µl of sample solution.

33. The disposable vessel of either of claim 1 or 2, further comprising a label fixable onto an exterior surface of said vessel, said label containing information relating to the contents of said vessel.

34. The disposable vessel of claim 33, wherein said information is machine-readable.

35. The disposable vessel of claim 34, wherein said information is in the form of a bar code.

36. The disposable vessel of claim 34, wherein said information is in the form of an encrypted bar code.

37. The disposable vessel of claim 33, wherein said information includes at least one member selected from the group consisting of type of test, the type of reagent in said tube, particle number, lot number, expiration date, serial number, particle concentration, particle extinction mean value, particle low-angle forward scatter mean value, particle high-angle forward scatter mean value, particle right-angle scatter mean value, particle extinction coefficient of variation, particle low-angle forward scatter coefficient of variation, particle high-angle forward scatter coefficient of variation, particle right-angle scatter coefficient of variation, optical density of sample at 488 nm, optical density of sample at 540 nm, optical density of sample at 580 nm, and optical density of sample at 635 nm.

38. The disposable vessel of claim 33, wherein said information includes the type of test.

39. The disposable vessel of claim 33, wherein said information includes the type of reagent in said tube.

40. The disposable vessel of claim 33, wherein said information includes particle number.

41. The disposable vessel of claim 33, wherein said information includes lot number.

42. The disposable vessel of claim 33, wherein said information includes expiration date.

43. The disposable vessel of claim 33, wherein said information includes serial number.

44. The disposable vessel of claim 33, wherein said information includes particle concentration.

45. The disposable vessel of claim 33, wherein said information includes particle extinction mean value.

46. The disposable vessel of claim 33, wherein said information includes particle low-angle forward scatter mean value.

47. The disposable vessel of claim 33, wherein said information includes particle high-angle forward scatter mean value.

48. The disposable vessel of claim 33, wherein said information includes particle right-angle scatter mean value.

49. The disposable vessel of claim 33, wherein said information includes particle extinction coefficient of variation.

50. The disposable vessel of claim 33, wherein said information includes particle low-angle forward scatter coefficient of variation.

51. The disposable vessel of claim 33, wherein said information includes particle high-angle forward scatter coefficient of variation.

52. The disposable vessel of claim 33, wherein said information includes particle right-angle scatter coefficient of variation.

53. The disposable vessel of claim 33, wherein said information includes optical density of sample at 488 nm.

54. The disposable vessel of claim 33, wherein said information includes optical density of sample at 540 nm.

55. The disposable vessel of claim 33, wherein said information includes optical density of sample at 580 nm.

56. The disposable vessel of claim 33, wherein said information includes optical density of sample at 635 nm.

57. The disposable vessel of claim 33, wherein said information includes a memory address, said memory address having information about at least one member selected from the group consisting of particle number, mean extinction value, mean low-angle forward scatter value, mean high-angle forward scatter value, mean right-angle scatter value, mean time-of-flight value, extinction coefficient of variation, low-angle forward scatter coefficient of variation, high-angle forward scatter coefficient of variation, right-angle scatter coefficient of variation, and time-of-flight coefficient of variation.

58. The disposable vessel of claim 57, wherein said memory address is stored in said flow cytometry-based hematology system.

59. The disposable vessel of claim 57, wherein said memory address is stored in a computer linked to said flow cytometry-based hematology system.

60. A disposable vessel for use in a flow cytometry-based hematology system, comprising:

a closed disposable tube having two closed ends;

a known number of reference particles in said disposable tube, each of said reference particles having a diameter of 4.0±0.5 microns;

a label fixable onto a surface of said closed disposable tube, said label containing information relating to the contents of said disposable tube; and at least one reagent in said closed tube, said reagent being effective to enable said flow cytometry-based hematology system to measure at least one of a red blood cell count, a reticulocyte count, a platelet count, a two-part white blood cell differential, a five-part white blood cell differential, and hemoglobin concentration.

61. The disposable vessel of claim 60, wherein said known number of reference particles in said tube is between about $10^3$ and about $10^5$ per μl of a sample solution.

62. The disposable vessel of claim 60, wherein said reference particles in said tube are polystyrene latex particles or divinylbenzene latex particles.

63. The disposable vessel of claim 60, wherein said reagent includes a reactant capable of staining ribonucleic acid in reticulocytes.

64. The disposable vessel of claim 63, wherein said reactant is new methylene blue.

65. The disposable vessel of claim 60, wherein said information is machine readable.

66. The disposable vessel of claim 65, wherein said information is in the form of a bar code.

67. The disposable vessel of claim 65, wherein said information is in the form of an encrypted bar code.

68. A consumable tube comprising:

a disposable tube member having two closed ends;

one or more reference particles disposed within the disposable tube member;

a reticulocyte dye disposed within the disposable tube member;

a surfactant disposed within the disposable tube member; and a label affixed to an outer surface of the disposable tube member, said label having information relating to at least the reference particles and the reticulocyte dye.

69. The disposable vessel of claim 1, wherein one closed end is defined by a portion of the disposable tube and the other closed end is defined by a rubber septum.

70. The disposable vessel of claim 2, wherein one closed end is defined by a portion of the disposable tube and the other closed end is defined by a rubber septum.

71. The disposable vessel of claim 60, wherein one closed end is defined by a portion of the disposable tube and the other closed end is defined by a rubber septum.

72. The disposable vessel of claim 68, wherein one closed end is defined by a portion of the disposable tube and the other closed end is defined by a rubber septum.

\* \* \* \* \*